US008188117B2

(12) United States Patent
Plettenburg et al.

(10) Patent No.: US 8,188,117 B2
(45) Date of Patent: May 29, 2012

(54) PIPERIDINYL-SUBSTITUTED ISOQUINOLONE DERIVATIVES

(75) Inventors: Oliver Plettenburg, Frankfurt (DE); Armin Hofmeister, Frankfurt (DE); Dieter Kadereit, Frankfurt (DE); Joachim Brendel, Frankfurt (DE); Matthias Loehn, Frankfurt (DE)

(73) Assignee: Sanofi-Aventis, Paris (FR)

( * ) Notice: Subject to any disclaimer, the term of this patent is extended or adjusted under 35 U.S.C. 154(b) by 1009 days.

(21) Appl. No.: 12/019,866

(22) Filed: Jan. 25, 2008

(65) Prior Publication Data

US 2009/0093518 A1 Apr. 9, 2009

Related U.S. Application Data

(63) Continuation of application No. PCT/EP2006/007139, filed on Jul. 20, 2006.

(30) Foreign Application Priority Data

Jul. 26, 2005 (EP) .................................... 05016154

(51) Int. Cl.
C07D 401/12 (2006.01)
A61K 31/4725 (2006.01)
(52) U.S. Cl. ........................................ 514/309; 546/141
(58) Field of Classification Search ........................ None
See application file for complete search history.

(56) References Cited

U.S. PATENT DOCUMENTS

| 5,480,883 | A | 1/1996 | Spada et al. |
| 6,903,107 | B1 | 6/2005 | Timmers et al. |
| 7,217,722 | B2 | 5/2007 | Takami et al. |
| 7,618,985 | B2 | 11/2009 | Ray et al. |
| 2003/0220368 | A1 | 11/2003 | Ozaki et al. |
| 2004/0138286 | A1 | 7/2004 | Imazaki et al. |
| 2006/0079556 | A1 | 4/2006 | Sher et al. |
| 2007/0060595 | A1 | 3/2007 | Yoshizawa et al. |
| 2008/0045566 | A1 | 2/2008 | Ray et al. |

FOREIGN PATENT DOCUMENTS

| EP | 1403255 | 3/2004 |
| EP | 1541559 | 6/2005 |
| EP | 1550660 | 7/2005 |
| FR | 2485537 | 6/1980 |
| JP | 10-87629 | 4/1998 |
| WO | 9202476 | 2/1992 |
| WO | WO97/06802 | 2/1997 |
| WO | WO97/23214 | 7/1997 |
| WO | 9806433 | 2/1998 |
| WO | WO99/11642 | 3/1999 |
| WO | 0024718 | 5/2000 |
| WO | WO00/73299 | 12/2000 |
| WO | WO01/39726 | 6/2001 |
| WO | WO01/53288 | 7/2001 |
| WO | WO01/56988 | 8/2001 |
| WO | WO01/64238 | 9/2001 |
| WO | WO01/64656 | 9/2001 |
| WO | WO01/77101 | 10/2001 |
| WO | WO01/92227 | 12/2001 |
| WO | WO02/34712 | 5/2002 |
| WO | WO02/055496 | 7/2002 |
| WO | WO02/076457 | 10/2002 |
| WO | WO02/088101 | 11/2002 |
| WO | WO03/018556 | 3/2003 |
| WO | WO03/024450 | 3/2003 |
| WO | WO03/053330 | 7/2003 |
| WO | WO2004/106325 | 12/2004 |
| WO | WO2004/113297 | 12/2004 |
| WO | WO2005/035933 | 2/2005 |
| WO | WO2005/030130 | 4/2005 |
| WO | WO2005/030791 | 4/2005 |
| WO | WO2005/035516 | 4/2005 |
| WO | 2005054202 | 6/2005 |
| WO | WO2005/074535 | 8/2005 |
| WO | WO2005/087226 | 9/2005 |
| WO | WO2005/095362 | 10/2005 |
| WO | 2007012422 A1 | 2/2007 |
| WO | 2007039563 A1 | 4/2007 |
| WO | WO 2007/065916 | 6/2007 |
| WO | 2008020081 A1 | 2/2008 |
| WO | WO 2008/020081 | 2/2008 |
| WO | 2008077555 A2 | 7/2008 |

(Continued)

OTHER PUBLICATIONS

Certified Priority Document, EPO 05016154.6, filed Jul. 26, 2005.*

(Continued)

*Primary Examiner* — Zinna Northington Davis
(74) *Attorney, Agent, or Firm* — Scully, Scott, Murphy & Presser, P.C.

(57) ABSTRACT

The invention relates to 6-piperidinyl-substituted isoquinolone derivatives of the formula (I)

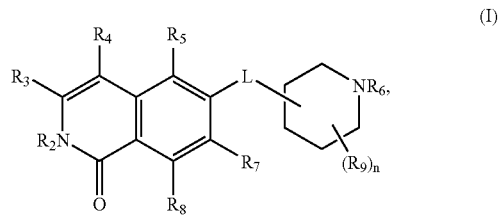

or isoquinoline derivatives of the formula (I')

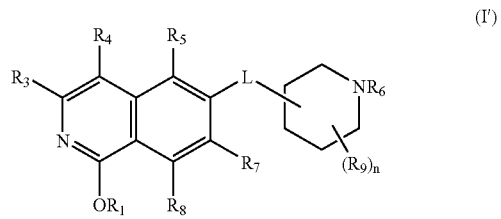

useful for the treatment and/or prevention of diseases associated with Rho-kinase and/or Rho-kinase mediated phosphorylation of myosin light chain phosphatase, and compositions containing such compounds.

69 Claims, No Drawings

FOREIGN PATENT DOCUMENTS

WO 2008077556 A1 7/2008

OTHER PUBLICATIONS

Yoshida et al., Studies on Anti-Helicobacter pylori Agents. Part 1: Benzyloxyisoquinoline Derivatives, Bioorg. & Med. Chem., vol. 7 (1999), pp. 2647-2666.
Alvarez, M. et al., "Product Class 5: Isoquinolines" Science of Synthesis (2005) pp. 661-838, vol. 15.
Alvarez, M. et al., "Product Class 6: Isoquinolines" Science of Synthesis (2005) pp. 839-890, vol. 15.
Remington's Pharmaceutical Sciences 17th Edition (1985), p. 1418.
Forzato, C. et al., "Baker's yeast reduction of 4-hetero-2-(2-nitroethyl)cyclohexanones" Tetrahedron: Asymmetry (1997) pp. 1811-1820, vol. 8.
U.S. Appl. No. 12/970,376, filed Dec. 16, 2010, Inventor: Plettenburg, et al, entitled: "6-Substituted Isoquinolines and Isoquinolinones".
U.S. Appl. No. 13/000,754, filed Apr. 20, 2011, Inventor: Plettenburg et al., entitled: "Substituted Isoquinolines and Isoquinolinones as Rho Kinase Inhibitors".
U.S. Appl. No. 13/000,202, filed Dec. 20, 2010, Inventor: Plettenburg et al., entitled: "Bi- and Polycyclic Substituted Isoquinoline and Isoquinolinone Derivatives".
Bonjoch, J. et al., "A New Synthetic Entry to the Tricyclic Skeleton of FR901483 by Palladium-Catalyzed Cyclization of Vinyl Bromides with Ketone Enolates" Tetrahedron Letters (2003) pp. 8387-8390, vol. 44.
Takami, A. et al., "Design and Synthesis of Rho Kinase Inhibitors (I)" Bioorganic & Medicinal Chemistry (2004) pp. 2115-2137, vol. 12.
Iwakubo, M. et al., "Design and Synthesis of Rho Kinase Inhibitors (III)" Bioorganic & Medicinal Chemistry (2007) pp. 1022-1033, vol. 15.
Iwakubo, M. et al., "Design and Synthesis of Rho Kinase Inhibitors (II)" Bioorganic & Medicinal Chemistry (2007) pp. 350-364, vol. 15.
Tamura, M. et al., "Development of Specific Rho-Kinase Inhibitors and Their Clinical Application" Biochimica et Biophysica Acta (2005) pp. 245-252, vol. 1754.
Becker, D.P. et al., "A Short Synthesis of 1-Azaadamantan-4-one and the 4r and 4s Isomers of 4-Amino-1-azaadamantane" Synthesis (1992) pp. 1080-1082, vol. 11.
Degraffenreid, M.R. et al., "An Efficient and Scalable One-Pot Double Michael Addition-Dieckmann Condensation for the Synthesis of 4,4-Disubstituted Cyclohexane β-Keto Esters" Journal of Organic Chemistry (2007) pp. 7455-7458, vol. 72.
Lednicer, D. et al., "4-Amino-4-arylcyclohexanones and Their Derivatives, a Novel Class of Analgesics. 1. Modification of the Aryl Ring" Journal of Medicinal Chemistry (1980) pp. 424-430, vol. 23.
Caron, S. et al., "The Synthesis of a Selective PDE4/TNFα Inhibitor" Organic Process Research and Development (2001) pp. 587-592, vol. 5.
Ai, S. et al., "Rho-Rho Kinase is Involved in Smooth Muscle Cell Migration Through Myosin Light Chain Phosphorylation-dependent and Independent Pathways" Atherosclerosis (2001) pp. 321-327, vol. 155.
Bauer, M. et al., "Dichotomous Regulation of Myosin Phosphorylation and Shape Change by Rho-Kinase and Calcium in Intact Human Platelets" Blood (1999) pp. 1665-1672, vol. 94.
Chellaiah, M. et al., "Rho-dependent Rho Kinase Activation Increases CD44 Surface Expression and Bone Resorption in Osteoclasts" The Journal of Biological Chemistry (2003) pp. 29086-29097, vol. 278.
Chitaley, K. et al., "Antagonism of Rho-kinase Stimulates Rat Penile Erection Via a Nitric Oxide-independent Pathway" Nature Medicine (2001) pp. 119-122, vol. 7.
Maruoka, S. et al., "Elastase Anti-elastase Imbalance in the Pathogens of COPD" Nippon Rinsho (1999) pp. 1982-1987, vol. 57.
Demiryürek, Ş. et al., "Effects of Fasudil, a Rho-kinase Inhibitor, on Myocardial Preconditioning in Anesthetized Rats" European Journal of Pharmacology (2005) pp. 129-140, vol. 527.
Retzer, M. et al., "Mildly Oxidised Low Density Lipoprotein Induces Platelet Shape Change Via Rho-kinase-dependent Phosphorylation of Myosin Light Chain and Moesin" FEBS Letters (2000) pp. 70-74, vol. 466.
Kimura, K. et al., "Regulation of the Association of Adducin with Actin Filaments by Rho-associated Kinase (Rho-kinase) and Myosin Phosphatase" The Journal of Biological Chemistry (1998) pp. 5542-5548, vol. 273.
Fukumoto, Y. et al., "Acute Vasodilator Effects of a Rho-kinase Inhibitor, Fasudil, in Patients with Severe Pulmonary Hypertension" Heart (2005) pp. 391-392, vol. 91.
Gingras, D. et al., "Tyrosine Phosphorylation of the Vascular Endothelial-Growth-Factor Receptor-2 (VEGFR-2) is Modulated by Rho Proteins" Biochemical Journal (2000) pp. 273-280, vol. 348.
Gokina, N.I. et al., "Effects of Rho Kinase Inhibition on Cerebral Artery Myogenic Tone and Reactivity" Journal of Applied Physiology (2005) pp. 1940-1948, vol. 98.
Sandu, O.A. et al., "Diabetes in the Goto-Kakizaki Rat is Accompanied by Impaired Insulin-Mediated Myosin-Bound Phosphatase Activation and Vascular Smooth Muscle Cell Relaxation" Diabetes (2000) pp. 2178-2189, vol. 49.
Hara, M. et al., "Protein Kinase Inhibition by Fasudil Hydrochloride Promotes Neurological Recovery After Spinal Cord Injury in Rats" Journal of Neurosurgery: Spine 1 (2000) pp. 94-101, vol. 93.
Hattori, T. et al., "Long-Term Inhibition of Rho-Kinase Suppresses Left Ventricular Remodeling After Myocardial Infarction in Mice" Circulation (2004) pp. 2234-2239, vol. 109.
Hitomi, A. et al., "Hemorheological Abnormalities in Experimental cerebral Ischemia and Effects of Protein Kinase Inhibitor on Blood Fluidity" Life Sciences (2000) pp. 1929-1939, vol. 67.
Honjo, M. et al., "Effects of Rho-Associated Protein Kinase Inhibitor Y-27632 on Intraocular Pressure and Outflow Facility" Investigative Ophthalmology and Visual Science (2001) pp. 137-144, vol. 42.
Inoue, M. et al., "Initiation of Neuropathic Pain Requires Lysophosphatidic Acid Receptor Signaling" Nature Medicine (2004) pp. 712-718, vol. 10.
Itoh, K. et al., "An Essential Part for Rho-associated Kinase in the Transcellular Invasion of Tumor Cells" Nature Medicine (1999) pp. 221-225, vol. 5.
Kawaguchi, A. et al., "The effect of a Rho kinase Inhibitor Y-27632 on Superoxide Production, Aggregation and Adhesion in Human Polymorphonuclear Leukocytes" European Journal of Pharmacology (2000) pp. 203-208, vol. 403.
Kim, I. et al., "Thin and Thick Filament Regulation of Contractility in Experimental Cerebral Vasospasm" Neurosurgery (2000) pp. 440-447, vol. 46.
Amano, M. et al., "Formation of Actin Stress Fibers and Focal Adhesions Enhanced by Rho-Kinase" Science (1997) pp. 1308-1311, vol. 275.
Kishi, T. et al., "Rho-Kinase Inhibitor Improves Increased Vascular Resistance and Impaired Vasodilation of the Forearm in Patients with Heart Failure" Circulation (2005) pp. 2741-2747, vol. 111.
Klages, B. et al., "Activation of G12/G13 Results in Shape Change and Rho/Rho-Kinase-mediated Myosin Light Chain Phosphorylation in Mouse Platelets" The Journal of Cell Biology (1999) pp. 745-754, vol. 144.
Noma, K. et al., "Physiological Role of ROCKs in the Cardiovascular Systems" American Journal of Physiology: Cell Physiology (2006) pp. C661-668, vol. 290.
Lin, T. et al., "Rho-ROCK-LIMK-Cofilin Pathway Regulates Shear Stress Activation of Sterol Regulatory Element Binding Proteins" Circulation Research (2003) pp. 1296-1304, vol. 92.
Furukawa, N. et al., "Role of Rho-kinase in Regulation of Insulin Action and Glucose Homeostasis" Cell Metabolism (2005) pp. 119-129, vol. 2.
Masumoto, A. et al., "Suppression of Coronary Artery Spasm by the Rho-Kinase Inhibitor Fasudil in Patients With Vasospastic Angina" Circulation (2002) pp. 1545-1547, vol. 105.
Nakahara, T. et al., "Y-27632 Potentiates Relaxant Effects of β2-adrenoceptor Agonists in Bovine Tracheal Smooth Muscle" European Journal of Pharmacology (2000) pp. 103-106, vol. 389.
Pacaud, P. et al., "Rho proteins and vascular diseases" Archives des Maladies du Coeur et des Vaisseaux (2005) pp. 249-254, vol. 98.

Pommereau, A. et al., "Two Simple and Generic Antibody-Independent Kinase Assays: Comparison of a Bioluminescent and a Microfluidic Assay Format" Journal of Biomedical Screening (2004) pp. 409-416, vol. 9.

Retzer, M. et al., "Lysophosphatidic Acid-induced Platelet Shape Change Proceeds Via Rho/Rho Kinase-mediated Myosin Light-chain and Moesin Phosphorylation" Cellular Signalling (2000) pp. 645-648, vol. 12.

Vicente-Manzanares, M. et al., "A Role for the Rho-p160 Rho Coiled-Coil Kinase Axis in the Chemokine Stromal Cell-Derived Factor-1α-Induced Lymphocyte Actomyosin and Microtubular Organization and Chemotaxis" The Journal of Immunology (2002) pp. 400-410, vol. 168.

Vicente-Manzanares, M. et al., "The RhoA Effector mDia Is Induced During T Cell Activation and Regulates Actin Polymerization and Cell Migration in T Lymphocytes" The Journal of Immunology (2003) pp. 1023-1034, vol. 171.

Sato, M. et al., "Involvement of Rho-Kinase-Mediated Phosphorylation of Myosin Light Chain in Enhancement of Cerebral Vasospasm" Circulation Research (2000) pp. 195-200, vol. 87.

Satoh, S. et al., "Pharmacological Profile of Hydroxy Fasudil as a Selective Rho Kinase Inhibitor on Ischemic Brain Damage" Life Sciences (2001) pp. 1441-1453, vol. 69.

Setoguchi, H. et al., "Leukotriene C4 Enhances the Contraction of Porcine Tracheal Smooth Muscle Through the Activation of Y-27632, a Rho Kinase Inhibitor, Sensitive Pathway" British Journal of Pharmacology (2001) pp. 111-118, vol. 132.

Shimokawa, H. et al., "Anti-anginal Effect of Fasudil, a Rho-Kinase Inhibitor, in Patients With Stable Effort Angina: A Multicenter Study" Journal of Cardiovascular Pharmacology (2002) pp. 751-761, vol. 40.

Steioff, K. et al., "Long Term Rho-kinase Inhibition Ameliorates Endothelial Dysfunction in LDL-Receptor Deficient Mice" European Journal of Pharmacology (2005) pp. 247-249, vol. 512.

Seasholtz, T.M. et al., "Rho and Rho Kinase Mediate Thrombin-Stimulated Vascular Smooth Muscle Cell DNA Synthesis and Migration" Circulation Research (1999) pp. 1186-1193, vol. 84.

Tatsumi, S. et al., "Involvement of Rho-Kinase in Inflammatory and Neuropathic Pain Through Phosphorylation of Myristoylated Alanine-Rich C-Kinase Substrate (Marcks)" Neuroscience (2005) pp. 491-498, vol. 131.

Uehata, M. et al., "Calcium Sensitization of Smooth Muscle Mediated by a Rho-associated Protein Kinase in Hypertension" Nature (1997) pp. 990-994, vol. 389.

Yamakawa, T. et al., "Involvement of Rho-Kinase in Angiotensin II-Induced Hypertrophy of Rat Vascular Smooth Muscle Cells" Hypertension (2000) pp. 313-318, vol. 35.

Yamamoto, Y. et al., "The Protein Kinase Inhibitor Fasudil Protects Against Ischemic Myocardial Injury Induced by Endothelin-1 in the Rabbit" Journal of Cardiovascular Pharmacology (2000) pp. 203-211, vol. 35.

Totsukawa, G. et al., "Distinct Roles of ROCK (Rho-kinase) and MLCK in Spatial Regulation of MLC Phosphorylation for Assembly of Stress Fibers and Focal Adhesions in 3T3 Fibroblasts" The Journal of Cell Biology (2000) pp. 797-806, vol. 150.

Yoshii, A. et al., "Relaxation of Contracted Rabbit Tracheal and Human Bronchial Smooth Muscle by Y-27632 through Inhibition of Ca2+ Sensitization" American Journal of Respiratory Cell and Molecular Biology (1999) pp. 1190-1200, vol. 20.

Zhou, Y. et al., "Nonsteroidal Anti-Inflammatory Drugs Can Lower Amyloidogenic Aβ42 by Inhibiting Rho" Science (2003) pp. 1215-1217, vol. 302.

Okada, H. et al., "Synthesis and Antitumor Activities of Prodrugs of Benzoylphenylureas" Chemical and Pharmaceutical Bulletin (1994) pp. 57-61, vol. 42.

Negoro, N. et al., "The Kinase Inhibitor Fasudil (HA-1077) Reduces Intimal Hyperplasia through Inhibiting Migration and Enhancing Cell Loss of Vascular Smooth Muscle Cells" Biochemical and Biophysical Research Communications (1999) pp. 211-215, vol. 262.

Somlyo, A.V. et al., "Rho-Kinase Inhibitor Retards Migration and in Vivo Dissemination of Human Prostate Cancer Cells" Biochemical and Biophysical Research Communications (2000) pp. 652-659, vol. 269.

Uchida, S. et al., "The Suppression of Small GTPase Rho Signal Transduction Pathway Inhibits Angiogenesis in Vitro and in Vivo" Biochemical and Biophysical Research Communications (2000) pp. 633-640, vol. 269.

Wakino, S. et al., "Rho/Rho Kinase as a Potential Target for the Treatment of Renal Disease" Drug News and Perspectives (2005) pp. 639-643, vol. 18.

U.S. Appl. No. 11/961,193, filed Dec. 20, 2007, Plettenburg, et. al.
U.S. Appl. No. 12/019,799, filed Jan. 25, 2008, Plettenburg, et. al.
U.S. Appl. No. 12/487,403, filed Jun. 18, 2009, Plettenburg, et. al.
U.S. Appl. No. 12/487,479, filed Jun. 18, 2009, Plettenburg, et. al.
U.S. Appl. No. 12/487,455, filed Jun. 18, 2009, Plettenburg, et. al.
U.S. Appl. No. 12/487,525, filed Jun. 18, 2009, Plettenburg, et. al.
U.S. Appl. No. 12/487,386, filed Jun. 18, 2009, Plettenburg, et. al.
U.S. Appl. No. 12/487,409, filed Jun. 18, 2009, Plettenburg, et. al.
U.S. Appl. No. 12/487,503, filed Jun. 18, 2009, Plettenburg, et. al.

Curren, et al., "The Preparation of Optically Active 2-Cyclopenten-1,4-Diol Derivatives from Furfuryl Alcohol", Tetrahedron, vol. 53, No. 6, pp. 1983-2004, 1997.

Kanda, et al., "Effect of fasudil on Rho-kinase and nephropathy in subtotally nephrectomized spontaneously hypertensive rats", Kidney International, vol. 64 (2003), pp. 2009-2019, Jul. 11, 2003.

* cited by examiner

PIPERIDINYL-SUBSTITUTED ISOQUINOLONE DERIVATIVES

This application is a continuation of International Application No. PCT/EP2006/007139 filed on Jul. 20, 2006, which claims benefit of priority to European Patent Application 05016154.6, filed on Jul. 26, 2005.

The present invention relates to novel isoquinolone and isoquinoline derivatives as described in the claims, their preparation and their use in the treatment and/or prevention of diseases related to the inhibition of Rho-kinase and/or of Rho-kinase mediated phosphorylation of myosin light chain phosphatase.

Activation of a small GTPase RhoA upon agonist stimulation results in conversion of RhoA from the inactive GDP-bound form to the active GTP-bound form with a subsequent binding to and activation of Rho-kinase. Two isoforms, Rho-kinase 1 and Rho-kinase 2, are known. Rho-kinase 2 is expressed in vascular smooth muscle cells and endothelial cells. Activation of Rho-kinase 2 by the active GTP-bound RhoA leads to calcium sensitization of smooth muscle cells through phosphorylation-mediated inhibition of the myosin light chain phosphatase activity and thereby up-regulation of the activity of myosin regulatory light chain (Uehata et al., Nature 1997, 389, 990-994).

It is known that Rho-kinase is involved in vasoconstriction, including the development of myogenic tone and smooth muscle hypercontractility (Gokina et al. J. Appl. Physiol. 2005, 98, 1940-8), bronchial smooth muscle contraction (Yoshii et al. Am. J. Resp. Cell Mol. Biol. 20, 1190-1200), asthma (Setoguchi et al. Br J Pharmacol. 2001, 132, 111-8; Nakahara, et al. Eur J 2000, 389, 103) and chronic obstructive pulmonary disease (COPD, Maruoka, Nippon Rinsho, 1999, 57, 1982-7), hypertension, pulmonary hypertension (Fukumoto et al. Heart, 91, 391-2, 2005, Mukai et al. Nature 1997, 389, 990-4) and ocular hypertension and regulation of intraocular pressure (Honjo et al. Invest. Opthalmol. Visual Sci. 2001, 42, 137-144), endothelial dysfunction (Steioff et al. Eur. J. Pharmacol. 2005, 512, 247-249), angina (Masumoto et al. Circ 2002, 105, 1545-47, Shimokawa et al. JCP, 2002, 40, 751-761), nephropathy, including hypertension-induced, non-hypertension-induced, and diabetic nephropathies, renal failure and peripheral occlusive arterial disease (PAOD) (Wakino et al. Drug News Perspect. 2005, 18, 639-43), myocardial infarction (Demiryurek et al. Eur J Pharmacol. 2005, 527, 129-40, Hattori et al. Circulation, 2004, 109, 2234-9), cardiac hypertrophy and failure (Yamakawa, et al. Hypertension 2000, 35, 313-318, Liao et al. Am J Physiol Cell Physiol. 2006, 290, C661-8, Kishi et al. Circ 2005, 111, 2741-2747), coronary heart disease, artherosclerosis, restenosis (Pacaud et al. Arch. Mal. Coeur 2005, 98, 249-254, Retzer, et al. FEBS Lett 2000, 466, 70, Negoro, et al. Biochem Biophys Res Commun 1999, 262, 211), diabetes, diabetic complications, glucose utilization and metabolic syndrome (Sandu, et al. Diabetes 2000, 49, 2178, Maeda et al. Cell Metab. 2005, 2, 119-29), sexual dysfunction, e.g., penile erectile dysfunction (Chitaley et al. Nature Medicine 2001, 7, 119-122), retinopathy, inflammation, immune diseases, AIDS, osteoporosis, endocrine dysfunctions, e.g. hyperaldosteronism, central nervous system disorders such as neuronal degeneration and spinal cord injury (Hara, et al. JNeurosurg 2000, 93, 94), cerebral ischemia (Uehata, et al. Nature 1997, 389, 990; Satoh et al. Life Sci. 2001, 69, 1441-53; Hitomi, et al. Life Sci 2000, 67, 1929; Yamamoto, et al. J Cardiovasc Pharmacol. 2000, 35, 203-11), cerebral vasospasm (Sato, et al. Circ Res 2000, 87, 195; Kim, et al. Neurosurgery 2000, 46, 440), pain, e.g. neuropathic pain (Tatsumi, et al. Neuroscience 2005, 131, 491, Inoue, et al. Nature medicine 2004, 10, 712), infection of digestive tracts with bacteria (WO 98/06433), cancer development and progression, neoplasia where inhibition of Rho kinase has been shown to inhibit tumor cell growth and metastasis (Itoh, et al. Nature Medicine 1999, 5, 221; Somlyo, et al. Res Commun 2000, 269, 652), angiogenesis (Uchida, et al. Biochem Biophys Res 2000, 269, 633-40; Gingras, et al. Biochem J 2000, 348, 273), vascular smooth muscle cell proliferation and motility (Tammy et al. Circ. Res. 1999, 84, 1186-1193; Tangkijvanich et al. Atherosclerosis 2001, 155, 321-327), endothelial cell proliferation, endothelial cell retraction and motility (Oikawa et al. Biochem. Biophys. Res. Commun. 2000, 269, 633-640), stress fiber formation (Kimura et al. Science 1997, 275, 1308-1311; Yamashiro et al. J. Cell Biol. 2000, 150, 797-806), thrombotic disorders (Kikkawa, et al. FEBS Lett. 2000, 466, 70-74; Bauer et al. Blood 1999, 94, 1665-1672, Klages, et al. J Cell Biol 1999, 144, 745; Retzer, et al. Cell Signal 2000, 12, 645) and leukocyte aggregation (Kawaguchi, et al. Eur J. Pharmacol. 2000, 403:203-8; Sanchez-Madrid, et al. J. Immunol. 2003, 171:1023-34, Sanchez-Madrid, et al. J Immunol. 2002, 168:400-10), and bone resorption (Chellaiah, et al. J Biol Chem. 2003, 278:29086-97). Na/H exchange transport system activation (Kawaguchi, et al. Eur J Pharmacol. 2000, 403:203-8), Alzheimer's disease (Zhou et al. Science 2003, 302, 1215-1217), adducin activation (Fukata et al. J. Biol. Chem., 1998, 273, 5542-5548), and in SREB (Sterol response binding element) signalling and its effects on lipid metabolism (Lin et al. Circ. Res., 92, 1296-304, 2003).

Therefore, a compound having inhibitory effect on Rho-kinase and/or on Rho-kinase mediated phosphorylation of myosin light chain phosphatase is useful for the treatment and/or prevention of cardiovascular and non-cardiovascular diseases involving Rho-kinase as the primary or secondary disease cause, like hypertension, pulmonary hypertension, ocular hypertension, retinopathy, and glaucoma, peripheral circulatory disorder, peripheral occlusive arterial disease (PAOD), coronary heart disease, angina pectoris, heart hypertrophy, heart failure, ischemic diseases, ischemic organ failure (end organ damage), fibroid lung, fibroid liver, liver failure, nephropathy, including hypertension-induced, non-hypertension-induced, and diabetic nephropathies, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, e.g. neuropathic pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy such as osteoporosis, infection of digestive tracts with bacteria, sepsis, cancer development and progression, e.g. cancers of the breast, colon, prostate, ovaries, brain and lung and their metastases.

WO 01/64238 describes isoquinoline-5-sulfonamide derivatives optionally substituted by a —($CH_2$)$_{1-6}$—O—($CH_2$)$_{0-6}$—, a —($CH_2$)$_{0-6}$—S—($CH_2$)$_{0-6}$— or a —($CH_2$)$_{0-6}$-linked heterocyclic group useful as neuroprotective agents.

WO 2004/106325 (Schering AG) describes prodrugs of the Rho-kinase inhibitor fasudil carrying an ether or ester group in the 1-position of the isoquinoline ring.

WO 2001/039726 generically describes —O—($C_0$-$C_{10}$) alkyl-heteroaryl substituted cyclohexyl derivatives useful for the treatment of microbial infections.

JP 10087629 A describes isoquinoline derivatives useful for the treatment of diseases caused by *Heliobacter pylori* such as for example gastritis cancer or ulcer. The isoquinoline derivatives may be substituted by OH in the 1-position and are preferably 5-substituted by X—[($C_1$-$C_6$)alkylene)]$_{0-1}$-Y wherein X may be oxygen and Y may be an aryl or a heterocyclic group.

Yoshida et al. (Bioorg. Med. Chem. 1999, 7, 2647-2666) disclose 6-benzyloxy-isoquinoline for the treatment of infections caused by *Heliobacter pylori*.

U.S. Pat. No. 5,480,883 generically discloses as EGF and/or PDGF receptor inhibitors useful for inhibiting cell proliferation compounds of the formula "Ar I-X-Ar II" wherein X may be $(CHR_1)_m$-Z-$(CHR_1)_n$, e.g. Z-$CH_2$, wherein Z may be O, $R_1$ is hydrogen or alkyl, Ar I may be among others an optionally substituted isoquinolone and Ar II may be among others an optionally substituted $C_{3-7}$ monocyclic saturated heterocyclic system.

WO 2005/030791 (Merck & Co.) generically describes as potassium channel inhibitors for the treatment of cardiac arrhythmias, stroke, congestive heart failure etc. isoquinolone derivatives which are optionally substituted in 6-position by a group $(CR^eR_f)_pOR^{43}$ wherein p may be zero, and $R^{43}$ is e.g. a group $R^{81}$ defined as a 4-6 membered unsaturated or saturated monocyclic heterocyclic ring with 1, 2, 3 or 4 heteroatoms selected from N, O or S; and are substituted by a directly bound optionally substituted aryl or heteroaryl ring in the 4-position.

WO 2005/030130 (Merck & Co.) generically describes as potassium channel inhibitors for the treatment of cardiac arrhythmias, stroke, congestive heart failure etc. isoquinoline derivatives which may be substituted by hydroxyl in the 1-position and are optionally substituted in 6-position by a group $(CR^eR^f)_pOR^{43}$ wherein p may be zero, and $R^{43}$ is e.g. a group $R^{81}$ defined as a 4-6 membered unsaturated or saturated monocyclic heterocylic ring with 1, 2, 3 or 4 heteroatoms selected from N, O or S; and are substituted by a directly bound optionally substituted aryl or heteroaryl ring in the 4-position.

WO 03/053330 (Ube) describes isoquinolone derivatives of the formula

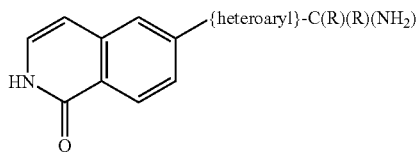

as Rho-kinase inhibitors.

An embodiment of the present invention is a compound of the formula (I)

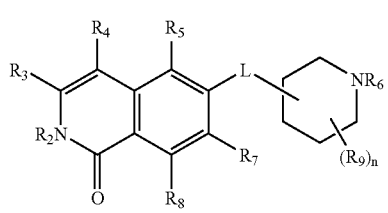

wherein $R_2$ is H, ($C_1$-$C_6$)alkyl, [($C_1$-$C_6$)alkylene]$_{0-1}$-O—R', [($C_1$-$C_6$)alkylene]$_{0-1}$-O—($C_1$-$C_6$)alkyl, [($C_1$-$C_6$)alkylene]$_{0-1}$-O—R', [($C_1$-$C_6$)alkylene]$_{0-1}$-$NH_2$, [($C_1$-$C_6$)alkylene]$_{0-1}$-NH ($C_1$-$C_6$)alkyl, [($C_1$-$C_6$)alkylene]$_{0-1}$-N[($C_1$-$C_6$)alkyl]$_2$, [($C_1$-$C_6$)alkylene]$_{0-1}$-CH[R']$_2$, [($C_1$-$C_6$)alkylene]$_{0-1}$-C (O)—R', [($C_1$-$C_6$)alkylene]$_{0-1}$-C(O)$NH_2$, [($C_1$-$C_6$)alkylene]$_{0-1}$-C(O)NH—R', or [($C_1$-$C_6$)alkylene]$_{0-1}$-C(O) N[R']$_2$;

$R_3$ is H, halogen, CN, ($C_1$-$C_6$)alkyl, ($C_1$-$C_6$)alkylene-R', OH, O—R", $NH_2$, NHR", NR"R" or NH—C(O)—R", $R_4$ is H, halogen, hydroxy, CN, ($C_1$-$C_6$)alkyl, ($C_3$-$C_8$)cycloalkyl, ($C_1$-$C_6$)alkylene-R';

$R_5$ is H, halogen, CN, $NO_2$, ($C_1$-$C_6$)alkyl, ($C_2$-$C_6$)alkenyl, R', ($C_1$-$C_6$)alkylene-($C_6$-$C_{10}$)aryl, ($C_2$-$C_6$)alkenylene-($C_6$-$C_{10}$)aryl, ($C_1$-$C_6$)alkylene-($C_5$-$C_{10}$)heterocyclyl, $NH_2$, NH—R', NH—$SO_2$H, NH—$SO_2$—($C_1$-$C_6$)alkyl, NH—$SO_2$—R', NH—C(O)—($C_1$-$C_6$)alkyl, NH—C(O)—R', C(O)N[($C_1$-$C_6$)alkyl]$_2$, C(O)OH or C(O)O—($C_1$-$C_6$)alkyl;

$R_6$ is H, R', ($C_1$-$C_8$)alkyl, ($C_1$-$C_6$)alkylene-R', ($C_1$-$C_6$)alkylene-O—($C_1$-$C_6$)alkyl, ($C_1$-$C_6$)alkylene-O—R', ($C_1$-$C_6$)alkylene-CH[R']$_2$, ($C_1$-$C_6$)alkylene-C(O)—R', ($C_1$-$C_6$)alkylene-C(O)$NH_2$, ($C_1$-$C_6$)alkylene-C(O)NH—R', or ($C_1$-$C_6$)alkylene-C(O)N[R']$_2$;

$R_7$ and $R_8$ are independently of each other H, halogen, CN, $NO_2$, ($C_1$-$C_6$)alkyl, O—($C_1$-$C_6$)alkyl, O—[($C_1$-$C_6$)alkylene]$_{0-1}$—R', ($C_2$-$C_6$)alkenyl, R', ($C_2$-$C_6$)alkenylene-($C_6$-$C_{10}$)aryl, ($C_1$-$C_6$)alkylene-R', $NH_2$, NH—R', NH—$SO_2$H, NH—$SO_2$—($C_1$-$C_6$)alkyl, NH—$SO_2$—R', $SO_2$—$NH_2$, $SO_2$—NHR', NH—C(O)—($C_1$-$C_6$)alkyl, NH—C(O)—R', C(O)N[($C_1$-$C_6$)alkyl]$_2$, C(O)OH or C(O)O—($C_1$-$C_6$) alkyl;

$R_9$ is halogen or ($C_1$-$C_6$)alkyl;

n is 0, 1, 2, 3 or 4; and

L is O or O—($C_1$-$C_6$)alkylene;

wherein R' is ($C_3$-$C_8$)cycloalkyl, ($C_5$-$C_{10}$)heterocyclyl or ($C_6$-$C_{10}$)aryl; and R" is ($C_3$-$C_8$)cycloalkyl, ($C_5$-$C_{10}$)heterocyclyl, ($C_6$-$C_{10}$)aryl, ($C_1$-$C_6$)alkyl, ($C_1$-$C_6$)alkylene-R', ($C_1$-$C_6$)alkylene-O—($C_1$-$C_6$)alkyl, ($C_1$-$C_6$)alkylene-O—R', or ($C_1$-$C_6$)alkylene-$NR_xR_y$; and wherein $R_x$ and $R_y$ are independently of each other ($C_1$-$C_6$) alkyl, ($C_5$-$C_{10}$)heterocyclyl, ($C_6$-$C_{10}$)aryl, ($C_1$-$C_4$)alkylene-($C_5$-$C_{10}$)heterocyclyl, ($C_1$-$C_4$)alkylene-($C_6$-$C_{10}$)aryl, ($C_1$-$C_4$)alkylene-NH($C_1$-$C_6$)alkyl, ($C_1$-$C_4$)alkylene-N[($C_1$-$C_6$)alkyl]$_2$, ($C_1$-$C_4$)alkylene-N[($C_6$-$C_{10}$)aryl]$_2$, or ($C_1$-$C_4$)alkylene-N[($C_5$-$C_{10}$)heterocyclyl]$_2$; and wherein in residues $R_4$, $R_5$, $R_7$ and $R_8$ one alkyl or alkylene hydrogen atom can optionally be substituted by OH, $OCH_3$, COOH, $COOCH_3$, $NH_2$, $NHCH_3$, $N(CH_3)_2$, $CONH_2$, $CONHCH_3$ or $CON(CH_3)_2$ or an alkyl or alkylene may be halogenated once or more;

or their pharmaceutically acceptable salts and/or stereoisomeric forms and/or physiologically functional derivatives.

In another embodiment of a compound of formula (I) in residues $R_4$, $R_5$, $R_7$ and $R_8$ one alkyl or alkylene hydrogen atom can optionally be substituted by OH, F, $OCH_3$, COOH, $COOCH_3$, $NH_2$, $NHCH_3$, $N(CH_3)_2$, $CONH_2$, $CONHCH_3$ or $CON(CH_3)_2$.

Stereoisomeric forms of the isoquinolone derivatives of the formula (I) include the corresponding tautomeric 1-hydroxy-substituted isoquinoline derivatives of the formula (I')

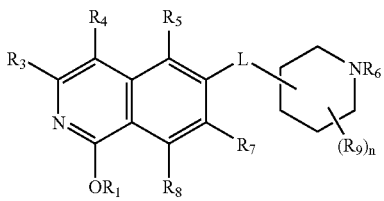

(I')

wherein $R_1$ is H, $(C_1-C_6)$alkyl, $(C_2-C_6)$alkenyl, $(C_2-C_6)$alkynyl, $[(C_1-C_6)$alkylene$]_{0-1}-(C_3-C_8)$cycloalkyl, $[(C_1-C_6)$alkylene$]_{0-1}-(C_5-C_{10})$heterocyclyl, $[(C_1-C_6)$alkylene$]_{0-1}-(C_6-C_{10})$aryl, C(O)—$(C_1-C_6)$alkyl, C(O)$(C_2-C_6)$alkenyl, C(O)—$(C_2-C_6)$alkynyl, C(O)-$[(C_1-C_6)$alkylene$]_{0-1}-(C_3-C_8)$cycloalkyl, C(O)-$[(C_1-C_6)$alkylene$]_{0-1}-(C_5-C_{10})$heterocyclyl, or C(O)-$[(C_1-C_6)$alkylene$]_{0-1}-(C_6-C_{10})$aryl, and wherein $R_3$, $R_4$, $R_5$, $R_6$, $R_7$, $R_8$, $R_9$, n and L are as defined above.

In a preferred embodiment, $R_2$ in the compound of the formula (I) is H, the compound is thus characterized by a compound of the formula (II)

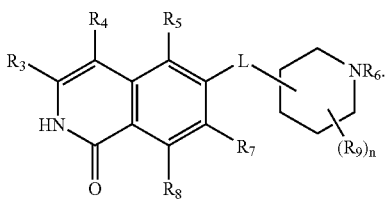

(II)

In a further preferred embodiment, $R_1$ in the compound of the formula (I') is H, the compound is thus characterized by a compound of the formula (II')

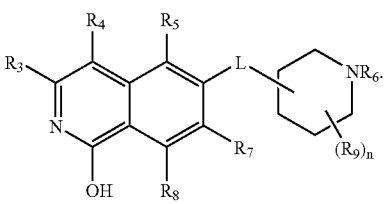

(II')

The compounds (II) and (II') are tautomeric forms of each other.

For example the compound of the formula

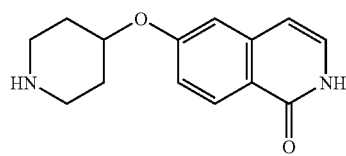

is a tautomer of the compound with the formula

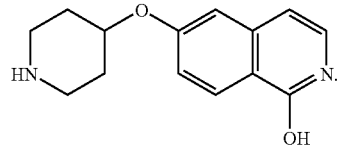

The following preferred embodiments refer to the compounds of the formulae (I), (I'), (II) and (II'):

$R_3$ is preferably H, halogen, $(C_1-C_6)$alkyl, $(C_1-C_4)$alkylene-R', O—R" or NHR". More preferred, $R_3$ is H, $(C_1-C_6)$ alkyl or NHR". Most preferred, $R_3$ is H, $(C_1-C_4)$alkyl, NH—$(C_5-C_6)$heterocyclyl or NH-phenyl, especially preferred $R_3$ is H, $(C_1-C_4)$alkyl, NH—$(C_5-C_6)$heteroaryl containing one or more N atoms or NH-phenyl. Most especially preferred, $R_3$ is H.

Preferably, $R_4$ is H, halogen, CN, $(C_1-C_6)$alkyl, NH—$(C_6-C_{10})$aryl or $(C_1-C_6)$alkylene-R'. More preferably, $R_4$ is H, halogen, $(C_1-C_6)$alkyl, NH—$(C_6-C_{10})$aryl or $(C_1-C_6)$alkylene-R'. In a further preferred embodiment, $R_4$ is H, halogen, $(C_1-C_6)$alkyl, NH—$(C_6-C_{10})$aryl or $(C_1-C_2)$alkylene-$(C_6-C_{10})$aryl. Most preferred, $R_4$ is H, halogen, or $(C_1-C_6)$alkyl. Especially preferred, $R_4$ is H, halogen or $(C_1-C_6)$alkyl. Most especially preferred, $R_4$ is H.

Preferably, $R_5$ is H, halogen, CN, $(C_1-C_6)$alkyl, R', NH—$(C_6-C_{10})$aryl or $(C_1-C_6)$alkylene-R'. More preferably, $R_5$ is H, halogen, $(C_1-C_6)$alkyl, R', NH—$(C_6-C_{10})$aryl or $(C_1-C_6)$alkylene-R'. In a further preferred embodiment, $R_5$ is H, halogen, $(C_6-C_{10})$aryl, NH—$(C_6-C_{10})$aryl, $(C_1-C_2)$alkylene-$(C_6-C_{10})$aryl, $(C_1-C_6)$alkyl or $(C_5-C_{10})$heteroaryl. Most preferred, $R_5$ is H, halogen, phenyl, $(C_1-C_6)$alkyl or $(C_5-C_6)$heteroaryl. Especially preferred, $R_5$ is H, halogen or $(C_1-C_6)$alkyl. More especially preferred $R_5$ is H or halogen. Most especially preferred, $R_5$ is H.

Preferably, $R_6$ is H, $(C_1-C_6)$alkyl, R', $(C_1-C_4)$alkylene-$(C_3-C_8)$cycloalkyl, $(C_1-C_4)$alkylene-$(C_5-C_{10})$heterocyclyl, $(C_1-C_4)$alkylene-C(O)—$(C_5-C_{10})$heterocyclyl, $(C_1-C_4)$alkylene-C(O)—$(C_6-C_{10})$aryl or $(C_1-C_6)$alkylene-$(C_6-C_{10})$aryl. In a further preferred embodiment, $R_6$ is H, $(C_1-C_6)$alkyl, $(C_5-C_{10})$heterocyclyl, $(C_3-C_8)$cycloalkyl, $(C_1-C_4)$alkylene-$(C_3-C_8)$cycloalkyl, $(C_1-C_4)$alkylene-$(C_5-C_{10})$heterocyclyl or $(C_1-C_6)$alkylene-$(C_6-C_{10})$aryl. More preferred, $R_6$ is H, $(C_1-C_6)$alkyl, $(C_3-C_8)$cycloalkyl, $(C_1-C_4)$alkylene-$(C_3-C_8)$cycloalkyl, $(C_1-C_4)$alkylene-$(C_5-C_{10})$heterocyclyl or $(C_1-C_6)$alkylene-$(C_6-C_{10})$aryl.

In a more preferred embodiment, $R_6$ is H, $(C_1-C_6)$alkyl, $(C_3-C_8)$cycloalkyl, $(C_1-C_4)$alkylene-$(C_3-C_9)$cycloalkyl, $(C_1-C_4)$alkylene-$(C_5-C_{10})$heterocyclyl, in which the heterocyclyl is unsubstituted or substituted by $(C_1-C_4)$alkyl, or is $(C_1-C_4)$alkylene-$(C_6-C_{10})$aryl, in which the aryl is unsubstituted or substituted, preferably one to three times, by halogen, $(C_1-C_4)$alkyl especially methyl, ethyl, isopropyl or 3,3,3-trifluoromethyl, O—$(C_1-C_4)$alkyl especially methoxy, $SO_2$—$(C_1-C_4)$alkyl especially $SO_2$—$CH_3$ or $SO_2$—$CF_3$, or by $N[(C_1-C_4)$alkyl$]_2$ especially $N(CH_3)_2$, In a more especially preferred embodiment $R_6$ is H, $(C_1-C_6)$alkyl, $(C_3-C_8)$cycloalkyl, $(C_1-C_4)$alkylene-$(C_3-C_8)$cycloalkyl, $(C_1-C_2)$alkylene-thienyl, $(C_1-C_2)$alkylene-pyridyl, $(C_1-C_2)$alkylene-piperidinyl, $(C_1-C_2)$alkylene-pyrrolidinyl, $(C_1-C_2)$alkylene-1-methyl-pyrrolyl, $(C_1-C_2)$alkylene-1-methyl-pyrazolyl, $(C_1-C_2)$alkylene-furanyl, $(C_1-C_2)$alkylene-tetrahydrofuranyl or $(C_1-C_2)$ alkylene-1H-indazolyl, $(C_1-C_2)$alkylene-naphtyl or $(C_1-C_2)$ alkylene-phenyl wherein phenyl is unsubstituted or substituted by halogen, methyl, ethyl, isopropyl, 3,3,3-trifluoromethyl, methoxy, $SO_2$—$CH_3$, $SO_2$—$CF_3$ or $N(CH_3)_2$;

preferably the $(C_1-C_2)$alkylene is methylene. In a more especially preferred embodiment, $R_6$ is H, $(C_1-C_6)$alkyl, $(C_3-C_6)$cycloalkyl or $(C_1-C_4)$alkylene-$(C_3-C_6)$cycloalkyl. In a further more especially preferred embodiment, $R_6$ is H, $(C_1-C_6)$alkyl. In a most preferred embodiment, $R_6$ is H. Examples of $R_6$ groups are hydrogen, methyl, ethyl, propyl, isopropyl, cyclopropyl, 3-methyl-butyl, butyl, s-butyl, 3,3,3-trifluoropropyl or a substituent selected from the group consisting of

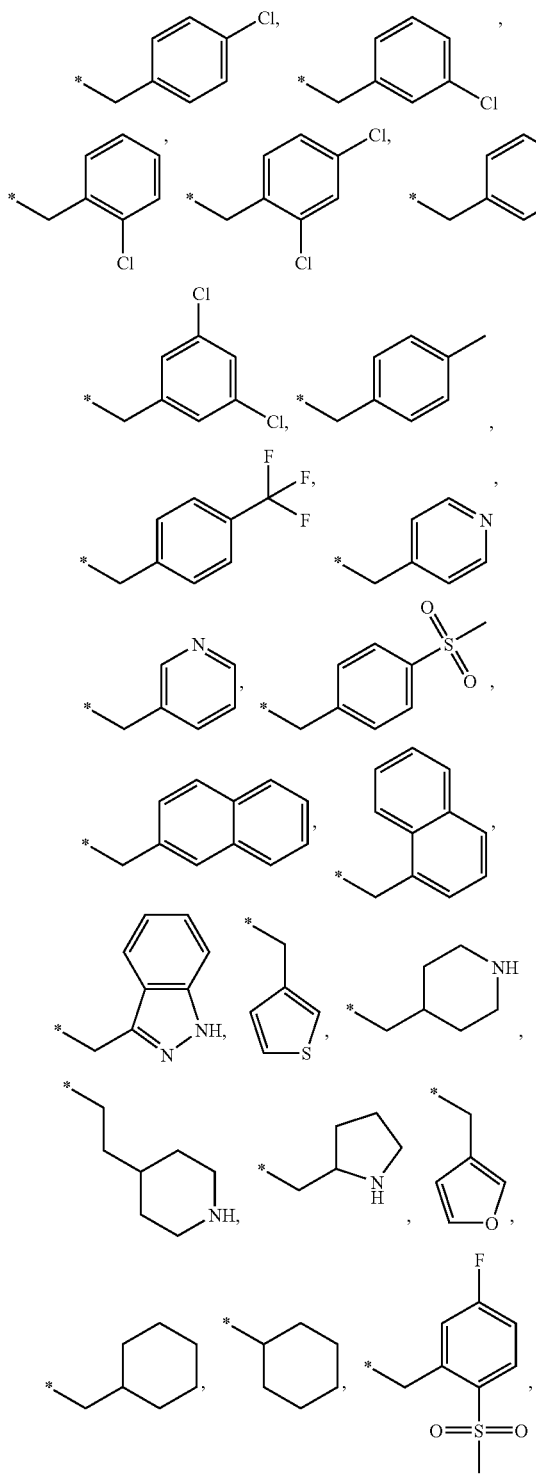

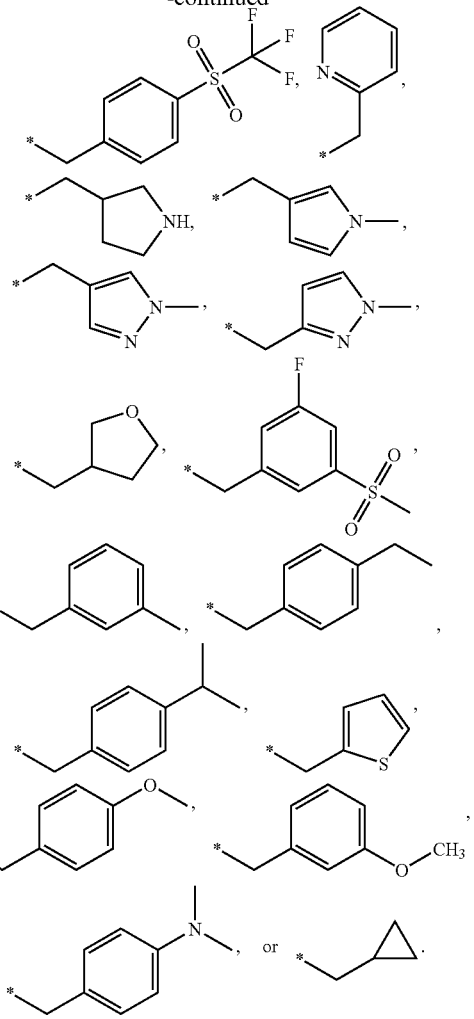

The asterisk (*) denotes where the bond is connected to the N-atom of the piperidine.

Preferably, $R_7$ and $R_8$ are independently of each other H, halogen, CN, $(C_1-C_6)$alkyl, O—$(C_1-C_6)$alkyl, $(C_2-C_6)$alkenyl, R' or $(C_1-C_6)$alkylene-$(C_3-C_8)$cycloalkyl. More preferred, $R_7$ and $R_8$ are independently of each other H, halogen, CN, $(C_1-C_4)$alkyl, O—$(C_1-C_4)$alkyl, $(C_2-C_4)$alkenyl, phenyl, $(C_3-C_6)$cycloalkyl, $(C_1-C_4)$alkylene-$(C_3-C_6)$cycloalkyl or $(C_5-C_6)$heteroaryl. Even more preferred, $R_7$ and $R_8$ are independently of each other H, halogen, $(C_1-C_4)$alkyl, O—$(C_1-C_4)$alkyl or $(C_3-C_6)$cycloalkyl. Most preferably, $R_7$ is H, halogen, $(C_1-C_4)$alkyl or O—$(C_1-C_4)$alkyl and $R_8$ is H. In another even more preferred embodiment $R_7$ and $R_8$ are independently of each other H, halogen, $(C_1-C_4)$alkyl, O—$(C_1-C_4)$alkyl or phenyl. Especially preferred, $R_7$ and $R_8$ are H.

$R_9$ is preferably halogen or $(C_1-C_4)$alkyl. More preferred, $R_9$ is Cl, F, methyl or ethyl. More preferably $R_9$ is methyl.

Preferably, n is 0, 1, 2 or 3. More preferred, n is 0 or 1. Most preferred, n is 0.

The linker group L may be bound to the piperidinyl ring in any position via a piperidinyl ring carbon atom and may thereby form the (R)- or the (S)-stereoisomer of a compound according to the invention.

In a preferred embodiment, L is attached to the 4-position of the piperidinyl ring

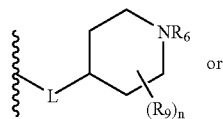

L is attached to the 3-position of the piperidinyl ring

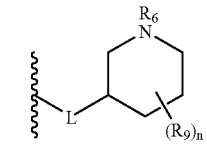

in all their stereochemical forms.

In an especially preferred embodiment, L is attached to the 4-position of the piperidinyl ring.

Preferably, L is O-methylene, O-ethylene or O. More preferably, L is O-methylene, O-ethylene or most preferred O attached to the 4-position of the piperidinyl ring.

Most preferably, L is O.

In preferred embodiments of the present invention one or more or all of the groups contained in the compounds of formulae (I) or (I') can independently of each other have any of the preferred, more preferred or most preferred definitions of the groups specified above or any one or some of the specific denotations which are comprised by the definitions of the groups and specified above, all combinations of preferred definitions, more preferred or most preferred and/or specific denotations being a subject of the present invention. Also with respect to all preferred embodiments the invention includes the compounds of the formulae (I) or (I') in all stereoisomeric forms and mixtures of stereoisomeric forms in all ratios, and/or their physiologically acceptable salts.

A preferred embodiment of the present invention is a compound of the formula (I), (I'), (II) or (II') wherein $R_3$ is H, halogen, CN, $(C_1-C_6)$alkyl, $(C_1-C_6)$alkylene-R', OH, O—R", $NH_2$, or NHR";

$R_4$ is H, halogen, hydroxy, CN, $(C_1-C_6)$alkyl, $(C_3-C_8)$cycloalkyl, $(C_1-C_6)$alkylene-R';

$R_5$ is H, halogen, CN, $NO_2$, $(C_1-C_6)$alkyl, $(C_2-C_6)$alkenyl, R', $(C_1-C_6)$alkylene-$(C_6-C_{10})$aryl, $(C_2-C_6)$alkenylene-$(C_6-C_{10})$aryl, $(C_1-C_6)$alkylene-$(C_5-C_{10})$heterocyclyl, $NH_2$, NH—R', NH—$SO_2$H, NH—$SO_2$—$(C_1-C_6)$alkyl, NH—$SO_2$—R', NH—C(O)—$(C_1-C_6)$alkyl, NH—C(O)—R', C(O)N[$(C_1-C_6)$alkyl]$_2$, C(O)OH or C(O)O—$(C_1-C_6)$alkyl;

$R_6$ is H, $(C_3-C_8)$cycloalkyl, $(C_1-C_8)$alkyl, $(C_1-C_6)$alkylene-R', $(C_1-C_6)$alkylene-O—$(C_1-C_6)$alkyl, $(C_1-C_6)$alkylene-O—R', $(C_1-C_6)$alkylene-CH[R']$_2$, $(C_1-C_6)$alkylene-C(O)NH$_2$, $(C_1-C_6)$alkylene-C(O)NH—R', or $(C_1-C_6)$alkylene-C(O)N[R']$_2$;

$R_7$ and $R_8$ are independently of each other H, halogen, CN, $NO_2$, $(C_1-C_6)$alkyl, $(C_2-C_6)$alkenyl, R', $(C_2-C_6)$alkenylene-$(C_6-C_{10})$aryl, $(C_1-C_6)$alkylene-R', $NH_2$, NH—R', NH—$SO_2$—$(C_1-C_6)$alkyl, NH—$SO_2$—R', $SO_2$—$NH_2$, $SO_2$—NHR', NH—C(O)—$(C_1-C_6)$alkyl, NH—C(O)—R', C(O)N[$(C_1-C_6)$alkyl]$_2$, C(O)OH or C(O)O—$(C_1-C_6)$alkyl;

$R_9$ is halogen or $(C_1-C_6)$alkyl;

n is 0, 1, 2; and

L is O or O—$(C_1-C_3)$alkylene;

wherein $R_1$, $R_2$, R', R", Rx and Ry are as defined above;

or their pharmaceutically acceptable salts and/or stereoisomeric forms and/or physiologically functional derivatives.

A further preferred embodiment of the present invention is a compound of the formula (I), (I'), (II) or (II') wherein $R_3$ is H, halogen, CN, $(C_1-C_6)$alkyl, $(C_1-C_2)$alkylene-R' or NHR";

$R_4$ is H, halogen, CN, $(C_1-C_6)$alkyl, $(C_3-C_8)$cycloalkyl, $(C_1-C_2)$alkylene-R';

$R_5$ is H, halogen, CN, $NO_2$, $(C_1-C_6)$alkyl, $(C_2-C_6)$alkenyl, R', $(C_1-C_6)$alkylene-$(C_6-C_{10})$aryl, $(C_2-C_6)$alkenylene-$(C_6-C_{10})$aryl, $(C_1-C_6)$alkylene-$(C_5-C_{10})$heterocyclyl, $NH_2$, NH—R', NH—C(O)—$(C_1-C_6)$alkyl, or C(O)N[$(C_1-C_6)$alkyl]$_2$;

$R_6$ is H, $(C_3-C_8)$cycloalkyl, $(C_1-C_8)$alkyl, or $(C_1-C_3)$alkylene-R';

$R_7$ and $R_8$ are independently of each other H, halogen, CN, $NO_2$, $(C_1-C_6)$alkyl, $(C_2-C_6)$alkenyl, R', $(C_2-C_3)$alkenylene-$(C_6-C_{10})$aryl, $(C_1-C_3)$alkylene-R', NH—R', NH—$SO_2$—$(C_1-C_6)$alkyl, or $SO_2$—$NH_2$;

$R_9$ is halogen or $(C_1-C_6)$alkyl;

n is 0 or 1; and

L is O or O-methylene;

wherein $R_1$, $R_2$, R', R", Rx and Ry are as defined above;

or their pharmaceutically acceptable salts and/or stereoisomeric forms and/or physiologically functional derivatives.

A most preferred embodiment of the present invention is a compound of the formula (I), (I'), (II) or (II') wherein $R_3$ is H, halogen, CN, $(C_1-C_6)$alkyl, $(C_1-C_2)$alkylene-R' or NHR";

$R_4$ is H, halogen, CN, $(C_1-C_4)$alkyl, $(C_3-C_6)$cycloalkyl, $(C_1-C_2)$alkylene-R';

$R_5$ is H, halogen, CN, $NO_2$, $(C_1-C_6)$alkyl, $(C_2-C_6)$alkenyl, R', $(C_1-C_6)$alkylene-$(C_6-C_{10})$aryl, $(C_2-C_6)$alkenylene-$(C_6-C_{10})$aryl, $(C_1-C_6)$alkylene-$(C_5-C_{10})$heterocyclyl, NH—R';

$R_6$ is H, $(C_3-C_6)$cycloalkyl or $(C_1-C_4)$alkyl;

$R_7$ and $R_8$ are independently of each other H, halogen, CN, $NO_2$, $(C_1-C_6)$alkyl, $(C_2-C_6)$alkenyl, R', $(C_2-C_3)$alkenylene-$(C_6-C_{10})$aryl, $(C_1-C_3)$alkylene-R', NH—$SO_2$—$(C_1-C_6)$alkyl, or $SO_2$—$NH_2$;

n is 0 and $R_9$ is not present or n is 1 and $R_9$ is halogen or $(C_1-C_4)$alkyl; and L is O;

wherein $R_1$, $R_2$, R', R", Rx and Ry are as defined above;

or their pharmaceutically acceptable salts and/or stereoisomeric forms and/or physiologically functional derivatives.

In another preferred embodiment of the present invention is a compound of the formula (I), (I'), (II) or (II') wherein $R_3$ is H, halogen, CN, $(C_1-C_6)$alkyl, $(C_1-C_6)$alkylene-R', OH, O—R", $NH_2$, or NHR";

$R_4$ is H, halogen, hydroxy, CN, $(C_1-C_6)$alkyl, $(C_3-C_8)$cycloalkyl, $(C_1-C_6)$alkylene-R';

$R_5$ is H, halogen, CN, $NO_2$, $(C_1-C_6)$alkyl, $(C_2-C_6)$alkenyl, R', $(C_1-C_6)$alkylene-$(C_6-C_{10})$aryl, $(C_2-C_6)$alkenylene-$(C_6-C_{10})$aryl, $(C_1-C_6)$alkylene-$(C_5-C_{10})$heterocyclyl, $NH_2$, NH—R', NH—$SO_2$H, NH—$SO_2$—$(C_1-C_6)$alkyl, NH—$SO_2$—R', NH—C(O)—$(C_1-C_6)$alkyl, NH—C(O)—R', C(O)N[$(C_1-C_6)$alkyl]$_2$, C(O)OH or C(O)O—$(C_1-C_6)$alkyl;

$R_6$ is H, $(C_3-C_8)$cycloalkyl, $(C_1-C_8)$alkyl, $(C_1-C_6)$alkylene-R', $(C_1-C_6)$alkylene-O—$(C_1-C_6)$alkyl, $(C_1-C_6)$alkylene-O—R', $(C_1-C_6)$alkylene-CH[R']$_2$, $(C_1-C_6)$alkylene-C(O)NH$_2$, $(C_1-C_6)$alkylene-C(O)NH—R', or $(C_1-C_6)$alkylene-C(O)N[R']$_2$;

$R_7$ and $R_8$ are independently of each other H, halogen, CN, $NO_2$, $(C_1$-$C_6)$alkyl, O—$(C_1$-$C_6)$alkyl, $(C_2$-$C_6)$alkenyl, R', $(C_2$-$C_6)$alkenylene-$(C_6$-$C_{10})$aryl, $(C_1$-$C_6)$alkylene-R', $NH_2$, NH—R', NH—$SO_2$—$(C_1$-$C_6)$alkyl, NH—$SO_2$—R', $SO_2$—$NH_2$, $SO_2$—NHR', NH—C(O)—$(C_1$-$C_6)$alkyl, NH—C(O)—R', C(O)N[$(C_1$-$C_6)$alkyl]$_2$, C(O)OH or C(O)O—$(C_1$-$C_6)$alkyl;

$R_9$ is halogen or $(C_1$-$C_6)$alkyl;

n is 0, 1, 2; and

L is O or O—$(C_1$-$C_4)$alkylene;

wherein $R_1$, $R_2$, R', R", $R_x$ and $R_y$ are as defined above;

or their pharmaceutically acceptable salts and/or stereoisomeric forms and/or physiologically functional derivatives.

A further preferred embodiment of the present invention is a compound of the formula (I), (I'), (II) or (II') wherein $R_3$ is H, halogen, CN, $(C_1$-$C_6)$alkyl, or $(C_1$-$C_2)$alkylene-R';

$R_4$ is H, halogen, CN, $(C_1$-$C_6)$alkyl, or $(C_1$-$C_2)$alkylene-R';

$R_5$ is H, halogen, CN, $NO_2$, $(C_1$-$C_6)$alkyl, $R_6$ is H, $(C_3$-$C_8)$cycloalkyl, $(C_1$-$C_8)$alkyl, $(C_1$-$C_3)$alkylene-$(C_3$-$C_6)$cycloalkyl, $(C_1$-$C_3)$alkylene-$(C_6$-$C_{10})$aryl or $(C_1$-$C_3)$alkylene-$(C_5$-$C_{10})$heterocyclyl;

$R_7$ and $R_8$ are independently of each other H, halogen, CN, $NO_2$, $(C_1$-$C_6)$alkyl, O—$(C_1$-$C_6)$alkyl, $(C_3$-$C_6)$cycloalkyl or phenyl;

$R_9$ is halogen or $(C_1$-$C_6)$alkyl;

n is 0 or 1; and

L is O or O-methylene;

wherein $R_1$, $R_2$, R', are as defined above;

or their pharmaceutically acceptable salts and/or stereoisomeric forms and/or physiologically functional derivatives.

A most preferred embodiment of the present invention is a compound of the formula (I), (I'), (II) or (II') wherein $R_3$ is H;

$R_4$ is H, halogen, or $(C_1$-$C_4)$alkyl;

$R_5$ is H, halogen or $(C_1$-$C_6)$alkyl;

$R_6$ is H, $(C_3$-$C_6)$cycloalkyl, $(C_1$-$C_4)$alkyl, $(C_1$-$C_2)$alkylene-$(C_3$-$C_6)$cycloalkyl, $(C_1$-$C_4)$alkylene-$(C_5$-$C_{10})$heterocyclyl, in which heterocyclyl is unsubstituted or substituted by $(C_1$-$C_4)$alkyl, or is $(C_1$-$C_4)$alkylene-$(C_6$-$C_{10})$aryl, in which aryl is unsubstituted or substituted by halogen, $(C_1$-$C_4)$alkyl, O—$(C_1$-$C_4)$alkyl, $SO_2$—$(C_1$-$C_4)$alkyl or N[$(C_1$-$C_4)$alkyl]$_2$;

$R_7$ and $R_8$ are independently of each other H, halogen, $(C_1$-$C_4)$alkyl, O—$(C_1$-$C_4)$alkyl or phenyl;

$R_9$ is $(C_1$-$C_4)$alkyl;

n is 0 or 1; and

L is O;

wherein $R_1$, $R_2$ are as defined above, preferably $R_1$ is H and $R_2$ is H;

or their pharmaceutically acceptable salts and/or stereoisomeric forms and/or physiologically functional derivatives.

As in any embodiment of the invention, in the preceding embodiments which contain preferred, more preferred, most preferred or exemplary definitions of compounds according to the invention, one or more or all of the groups can have any of its preferred, more preferred, most preferred definitions specified above or any one or some of the specific denotations which are comprised by its definitions and are specified above.

Physiologically acceptable salts of compounds of the formulae (I) and (I') mean both their organic and inorganic salts as described in Remington's Pharmaceutical Sciences (17th edition, page 1418 (1985)). Because of the physical and chemical stability and the solubility, preference is given for acidic groups inter alia to sodium, potassium, calcium and ammonium salts; preference is given for basic groups inter alia to salts of maleic acid, fumaric acid, succinic acid, malic acid, tartaric acid, methylsulfonic acid, hydrochloric acid, sulfuric acid, phosphoric acid or of carboxylic acids or sulfonic acids, for example as hydrochlorides, hydrobromides, phosphates, sulfates, methanesulfonates, acetates, lactates, maleates, fumarates, malates, gluconates, and salts of amino acids, of natural bases or carboxylic acids. The preparation of physiologically acceptable salts from compounds of the formulae (I) and (I') which are capable of salt formation, including their stereoisomeric forms, takes place in a manner known per se. The compounds of the formula (I) form stable alkali metal, alkaline earth metal or optionally substituted ammonium salts with basic reagents such as hydroxides, carbonates, bicarbonates, alcoholates and ammonia or organic bases, for example trimethyl- or triethylamine, ethanolamine, diethanolamine or triethanolamine, trometamol or else basic amino acids, for example lysine, ornithine or arginine. Where the compounds of the formulae (I) or (I') have basic groups, stable acid addition salts can also be prepared with strong acids. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid.

Salts with a physiologically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formulae (I) or (I') of the invention, for example an N-oxide, which on administration to a mammal such as, for example, a human is able to form (directly or indirectly) a compound of the formula (I) or (I') or an active metabolite thereof.

Physiologically functional derivatives include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The invention relates to a compound of the formula (I) or (I') in the form of their racemates, racemic mixtures and pure enantiomers and to their diastereomers and mixtures thereof.

If radicals or substituents may occur more than once in the compounds of the formulae (I) or (I'), they may all, independently of one another, have the stated meaning and be identical or different.

The compounds of the invention may also exist in various polymorphous forms and/or solvates, for example as amorphous and crystalline polymorphous forms. All polymorphous forms of the compounds of the invention belong within the framework of the invention and are a further aspect of the invention.

All references to "compound(s) of formula (I)" or to "compound(s) of formula (I')" hereinafter refer to compound(s) of the formulae (I) or (I') as described above, and their physiologically acceptable salts, solvates and physiologically functional derivatives as described herein.

The term alkyl and the corresponsonding alkylene substituents are understood as a hydrocarbon residue which can be linear, i.e. straight-chain, or branched and has 1, 2, 3, 4, 5 or 6 carbon atoms, respectively, where applicable. This also applies if an alkyl group occurs as a substituent on another group, for example in an alkoxy group (O-alkyl), S-alkyl or a —O($C_1$-$C_6$)alkylene-O—, an alkoxycarbonyl group or an arylalkyl group. Examples of alkyl groups are methyl, ethyl, propyl, butyl, pentyl or hexyl, the n-isomers of all these groups, isopropyl, isobutyl, 1-methylbutyl, isopentyl, neopentyl, 2,2-dimethylbutyl, 2-methylpentyl, 3-methylpentyl, isohexyl, sec-butyl, tert-butyl or tert-pentyl. Alkyl groups may—if not otherwise stated—be halogenated once or more, e.g. alkyl groups may be fluorinated, e.g. perfluorinated. Examples of halogenated alkyl groups are $CF_3$ and $CH_2CF_3$, $OCF_3$, $SCF_3$, or —O—$(CF_2)_2$—O—.

Alkenyl are, for example, vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl. Alkynyl are, for example, ethynyl, 1-propynyl, 2-propynyl (=propargyl) or 2-butynyl.

Halogen means fluoro, chloro, bromo or iodo.

($C_3$-$C_8$)cycloalkyl groups are cyclic alkyl groups containing 3, 4, 5, 6, 7 or 8 ring carbon atoms like cyclopropyl, cyclobutyl, cyclopentyl, cyclohexyl or cyclooctyl, which can also be substituted and/or contain 1 or 2 double bounds (unsaturated cycloalkyl groups) like, for example, cyclopentenyl or cyclohexenyl can be bonded via any carbon atom.

A ($C_6$-$C_{10}$)aryl group means an aromatic ring or a ring system which comprises two aromatic rings which are fused or otherwise linked, for example a phenyl, naphthyl, biphenyl, tetrahydronaphthyl, alpha- or beta-tetralon-, indanyl- or indan-1-on-yl group. A preferred ($C_6$-$C_{10}$)aryl group is phenyl.

A ($C_5$-$C_{10}$)heterocyclyl group means a mono- or bicyclic ring system which comprises, apart from carbon, one or more heteroatoms such as, for example, e.g. 1, 2 or 3 nitrogen atoms, 1 or 2 oxygen atoms, 1 or 2 sulfur atoms or combinations of different hetero atoms. The heterocyclyl residues can be bound at any positions, for example on the 1-position, 2-position, 3-position, 4-position, 5-position, 6-position, 7-position or 8-position. ($C_5$-$C_{10}$)heterocyclyl groups may be (1) aromatic [=heteroaryl groups] or (2) saturated or (3) mixed aromatic/saturated.

Suitable ($C_5$-$C_{10}$)heterocyclyl group include acridinyl, azocinyl, benzimidazolyl, benzofuryl, benzomorpholinyl, benzothienyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, furanyl, quinazolinyl, quinolinyl, 4H-quinolizinyl, quinoxalinyl, quinuclidinyl, chromanyl, chromenyl, chromen-2-onyl, cinnolinyl, decahydroquinolinyl, 2H,6H-1,5,2-dithiazinyl, dihydrofuro[2,3-b]-tetrahydrofuran, furyl, furazanyl, homomorpholinyl, homopiperazinyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, prolinyl, pteridinyl, purynyl, pyranyl, pyrazinyl, pyroazolidinyl, pyrazolinyl, pyrazolyl, pyridazinyl, pyridonyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl. Pyridyl stands both for 2-, 3- and 4-pyridyl. Thienyl stands both for 2- and 3-thienyl. Furyl stands both for 2- and 3-furyl. Also included are the corresponding N-oxides of these compounds, for example, 1-oxy-2-, 3- or 4-pyridyl.

Substitutions in ($C_5$-$C_{10}$)heterocyclyl residues can occur on free carbon atoms or on nitrogen atoms.

Preferred examples of ($C_5$-$C_{10}$)heterocyclyl residues are pyrazinyl, pyridyl, pyrimidinyl, pyrazolyl, morpholinyl, pyrrolidinyl, piperazinyl, piperidinyl, thienyl, benzofuryl, quinolinyl, tetrazolyl and triazolyl.

($C_6$-$C_{10}$)aryl and ($C_5$-$C_{10}$)heterocyclyl groups are unsubstituted or, unless otherwise stated, substituted one or more times by suitable groups independently selected from halogen, $CF_3$, $NO_2$, $N_3$, CN, C(O)—($C_1$-$C_6$)alkyl, C(O)—($C_1$-$C_6$)aryl, COOH, COO($C_1$-$C_6$)alkyl, $CONH_2$, CONH($C_1$-$C_6$)alkyl, CON[($C_1$-$C_6$)alkyl]$_2$, ($C_3$-$C_8$)cycloalkyl, ($C_1$-$C_6$)alkyl, ($C_1$-$C_6$)alkylene-OH, ($C_1$-$C_6$)alkylene-$NH_2$, ($C_1$-$C_6$)alkylene-NH($C_1$-$C_6$)alkyl, ($C_1$-$C_6$)alkylene-N[($C_1$-$C_6$)alkyl]$_2$, ($C_2$-$C_6$)alkenyl, ($C_2$-$C_6$)alkynyl, O—($C_1$-$C_6$)alkyl, O—C(O)—($C_1$-$C_6$)alkyl, O—C(O)—($C_6$-$C_{10}$)aryl, O—C(O)—($C_5$-$C_{10}$)heterocyclyl, $PO_3H_2$, $SO_3H$, $SO_2$—$NH_2$, $SO_2$NH($C_1$-$C_6$)alkyl, $SO_2$N[($C_1$-$C_6$)alkyl]$_2$, S—($C_1$-$C_6$)alkyl; S—($C_1$-$C_6$)alkylene-($C_6$-$C_{10}$)aryl, S—($C_1$-$C_6$)alkylene-($C_5$-$C_{10}$)heterocyclyl, SO—($C_1$-$C_6$)alkyl, SO—($C_1$-$C_6$)alkylene-($C_6$-$C_{10}$)aryl, SO—($C_1$-$C_6$)alkylene-($C_5$-$C_{10}$)heterocyclyl, $SO_2$—($C_1$-$C_6$)alkyl, $SO_2$—($C_1$-$C_6$)alkylene-($C_6$-$C_{10}$)aryl, $SO_2$—($C_1$-$C_6$)alkylene-($C_5$-$C_{10}$)heterocyclyl, $SO_2$—NH($C_1$-$C_6$)alkylene-($C_6$-$C_{10}$)aryl, $SO_2$—NH($C_1$-$C_6$)alkylene-($C_5$-$C_{10}$)heterocyclyl, $SO_2$—N[($C_1$-$C_6$)alkyl][($C_1$-$C_6$)alkylene-($C_6$-$C_{10}$)aryl], $SO_2$—N[($C_1$-$C_6$)alkyl][($C_1$-$C_6$)alkylene-($C_5$-$C_{10}$)heterocyclyl], $SO_2$—N[($C_1$-$C_6$)alkylene-($C_6$-$C_{10}$)aryl]$_2$, $SO_2$—N[($C_1$-$C_6$)alkylene-($C_5$-$C_{10}$)heterocyclyl]$_2$, C(NH)($NH_2$), $NH_2$, NH—($C_1$-$C_6$)alkyl, N[($C_1$-$C_6$)alkyl]$_2$, NH—C(O)—($C_1$-$C_6$)alkyl, NH—C(O)O—($C_1$-$C_6$)alkyl, NH—C(O)—($C_6$-$C_{10}$)aryl, NH—C(O)—($C_5$-$C_{10}$)heterocyclyl, NH—C(O)O—($C_6$-$C_{10}$)aryl, NH—C(O)O—($C_5$-$C_{10}$)heterocyclyl, NH—C(O)—NH—($C_1$-$C_6$)alkyl, NH—C(O)—NH—($C_6$-$C_{10}$)aryl, NH—C(O)—NH—($C_5$-$C_{10}$)heterocyclyl, NH—$SO_2$—($C_1$-$C_6$)alkyl, NH—$SO_2$—($C_6$-$C_{10}$)aryl, NH—$SO_2$—($C_5$-$C_{10}$)heterocyclyl, N($C_1$-$C_6$)alkyl-C(O)—($C_1$-$C_6$)alkyl, N($C_1$-$C_6$)alkyl-C(O)O—($C_1$-$C_6$)alkyl, N($C_1$-$C_6$)alkyl-C(O)—($C_6$-$C_{10}$)aryl, N($C_1$-$C_6$)alkyl-C(O)-heterocyclyl, N($C_1$-$C_6$)alkyl-C(O)O—($C_6$-$C_{10}$)aryl, N($C_1$-$C_6$)alkyl-C(O)O—($C_5$-$C_{10}$)heterocyclyl, N($C_1$-$C_6$)alkyl-C(O)—NH—($C_1$-$C_6$)alkyl], N($C_1$-$C_6$)alkyl-C(O)—NH—($C_6$-$C_{10}$)aryl, N($C_1$-$C_6$)alkyl-C(O)—NH—($C_5$-$C_{10}$)heterocyclyl, N[($C_1$-$C_6$)alkyl]-C(O)—N[($C_1$-$C_6$)alkyl]$_2$, N[($C_1$-$C_6$)alkyl]-C(O)—N[($C_1$-$C_6$)alkyl]-($C_6$-$C_{10}$)aryl, N[($C_1$-$C_6$)alkyl]-C(O)—N[($C_1$-$C_6$)alkyl]-($C_5$-$C_{10}$)heterocyclyl, N[($C_1$-$C_6$)alkyl]-C(O)—N[($C_6$-$C_{10}$)aryl]$_2$, N[($C_1$-$C_6$)alkyl]-C(O)—N[($C_5$-$C_{10}$)heterocyclyl]$_2$, N[($C_6$-$C_{10}$)aryl]-C(O)—($C_1$-$C_6$)alkyl, N[($C_5$-$C_{10}$)heterocyclyl]-C(O)—($C_1$-$C_6$)alkyl, N[($C_6$-$C_{10}$)aryl]-C(O)O—($C_1$-$C_6$)alkyl, N[($C_5$-$C_{10}$)heterocyclyl]-C(O)O—($C_1$-$C_6$)alkyl, N(aryl)-C(O)—($C_6$-$C_{10}$)aryl, N[($C_5$-$C_{10}$)heterocyclyl]-C(O)—($C_6$-$C_{10}$)aryl, N[($C_6$-$C_{10}$)aryl]-C(O)O—($C_6$-$C_{10}$)aryl, N[($C_5$-$C_{10}$)heterocyclyl]-C(O)O—($C_6$-$C_{10}$)aryl, N[($C_6$-$C_{10}$)aryl]-C(O)—NH—($C_1$-$C_6$)alkyl, N[($C_5$-$C_{10}$)heterocyclyl]-C(O)—NH—($C_1$-$C_6$)alkyl, N(aryl)-C(O)—NH—($C_6$-$C_{10}$)aryl, N[($C_5$-$C_{10}$)heterocyclyl]-C(O)—NH—($C_6$-$C_{10}$)aryl, N[($C_6$-$C_{10}$)aryl]-C(O)—N[($C_1$-$C_6$)alkyl]$_2$, N[($C_5$-$C_{10}$)heterocyclyl]-C(O)—N[($C_1$-$C_6$)alkyl]$_2$, N[($C_6$-$C_{10}$)aryl]-C(O)—N[($C_1$-$C_6$)alkyl]-($C_6$-$C_{10}$)aryl, N[($C_5$-$C_{10}$)heterocyclyl]-C(O)—N[($C_1$-$C_6$)alkyl]-($C_6$-$C_{10}$)aryl, N[($C_6$-$C_{10}$)aryl]-C(O)—N[($C_6$-$C_{10}$)aryl]$_2$, N[($C_5$-$C_{10}$)heterocyclyl]-C(O)—N[($C_6$-$C_{10}$)aryl]$_2$, ($C_6$-$C_{10}$)aryl, ($C_1$-$C_6$)alkylene-($C_6$-$C_{10}$)aryl, O—($C_1$-$C_6$)alkylene-($C_6$-$C_{10}$)aryl, ($C_5$-$C_{10}$)heterocyclyl, ($C_1$-$C_6$)alkylene-($C_5$-$C_{10}$)heterocyclyl, O—($C_1$-$C_6$)alkylene-($C_5$-$C_{10}$)heterocyclyl, wherein the ($C_6$-$C_{10}$)aryl or ($C_5$-$C_{10}$)heterocyclyl may be substituted one to 3 times by halogen, OH, $NO_2$, CN, O—($C_1$-$C_6$)alkyl, ($C_1$-$C_6$)alkyl, $NH_2$, NH($C_1$-$C_6$)alkyl, N[($C_1$-$C_6$)alkyl]$_2$, $SO_2CH_3$, COOH, C(O)O—($C_1$-$C_6$)alkyl, $CONH_2$, ($C_1$-$C_6$)alkylene-O—($C_1$-$C_6$)alkyl, ($C_1$-$C_6$)alkylene-O—($C_6$-$C_{10}$)aryl, O—($C_1$-$C_6$)alkylene-($C_6$-$C_{10}$)aryl; or wherein ($C_6$-$C_{10}$)aryl is vicinally substituted by a O—($C_1$-$C_4$)alkylene-O group whereby a 5-8-membered ring is formed together with the carbon atoms the oxygen atoms are attached to. Aryl or heterocyclyl substituents of ($C_6$-$C_{10}$)aryl and ($C_5$-$C_{10}$)heterocyclyl groups may not be further substituted by an aryl or heterocyclyl containing group.

If substituted, preferred substituents for ($C_6$-$C_{10}$)aryl groups are ($C_1$-$C_4$)alkyl, O—($C_1$-$C_4$)alkyl, O-phenyl, C(O)O—($C_1$-$C_6$)alkyl, C(O)OH, C(O)—($C_1$-$C_4$)alkyl, halogen, $NO_2$, $SO_2NH_2$, CN, $SO_2$—($C_1$-$C_4$)alkyl, NH—$SO_2$—($C_1$-$C_4$)alkyl, $NH_2$, NH—C(O)—($C_1$-$C_4$)alkyl, ($C_3$-$C_8$)cycloalkyl, ($C_1$-$C_4$)alkyl-OH, C(O)N[($C_1$-$C_4$)alkyl]$_2$, C(O)$NH_2$, N[($C_1$-$C_4$)alkyl]$_2$, ($C_1$-$C_4$)alkenylene-($C_6$-$C_{10}$)aryl, wherein the ($C_6$-$C_{10}$)aryl may be further substituted by ($C_1$-$C_4$)alkyl, ($C_1$-$C_4$)alkylene-O—($C_1$-$C_6$)alkyl, O—($C_1$-$C_6$)alkyl-($C_6$-$C_{10}$)aryl, or may be vicinally substituted by a O—($C_1$-$C_4$)alkylene-O group whereby a 5-8-membered ring is formed together with the carbon atoms the oxygen atoms are attached to. More preferably, substituents for ($C_6$-$C_{10}$)aryl are halogen, ($C_1$-$C_4$)alkyl especially methyl, ethyl, isopropyl or 3,3,3-trifluoromethyl, O—($C_1$-$C_4$)alkyl especially methoxy, $SO_2$—($C_1$-$C_4$)alkyl especially $SO_2$—$CH_3$ or $SO_2$—$CF_3$, or N[($C_1$-$C_4$)alkyl]$_2$ especially N[($CH_3$)$_2$.

In monosubstituted phenyl groups the substituent can be located in the 2-position, the 3-position or the 4-position, with the 3-position and the 4-position being preferred. If a phenyl group carries two substituents, they can be located in 2,3-position, 2,4-position, 2,5-position, 2,6-position, 3,4-position or 3,5-position. In phenyl groups carrying three substituents the substituents can be located in 2,3,4-position, 2,3,5-position, 2,3,6-position, 2,4,5-position, 2,4,6-position, or 3,4,5-position.

The above statements relating to phenyl groups correspondingly apply to divalent groups derived from phenyl groups, i.e. phenylene which can be unsubstituted or substituted 1,2-phenylene, 1,3-phenylene or 1,4-phenylene. The above statements also correspondingly apply to the aryl subgroup in arylalkylene groups. Examples of arylalkylene groups which can also be unsubstituted or substituted in the aryl subgroup as well as in the alkylene subgroup, are benzyl, 1-phenylethylene, 2-phenylethylene, 3-phenylpropylene, 4-phenylbutylene, 1-methyl-3-phenyl-propylene.

If substituted, preferred substituents for ($C_5$-$C_{10}$)heterocyclyl groups are ($C_1$-$C_4$)alkyl, O—($C_1$-$C_4$)alkyl, ($C_1$-$C_4$)alkylene-phenyl, halogen, ($C_1$-$C_4$)alkylene-O—($C_1$-$C_4$)alkyl, ($C_5$-$C_{10}$)heterocyclyl, ($C_1$-$C_4$)alkylene-N[($C_1$-$C_4$)alkyl]$_2$, or ($C_6$-$C_{10}$)aryl, wherein the ($C_6$-$C_{10}$)aryl may be further substituted by ($C_1$-$C_4$)alkyl, ($C_1$-$C_4$)alkylene-O—($C_1$-$C_6$)alkyl, O—($C_1$-$C_6$)alkyl-($C_6$-$C_{10}$)aryl, or may be vicinally substituted by a O—($C_1$-$C_4$)alkylene-O group whereby a 5-8-membered ring is formed together with the carbon atoms the oxygen atoms are attached to. More preferred substituents for ($C_5$-$C_{10}$)heterocyclyl are ($C_1$-$C_4$)alkyl.

The general and preferred substituents of ($C_6$-$C_{10}$)aryl and ($C_5$-$C_{10}$)heterocyclyl groups may be combined with the general and preferred definitions of $R_1$, $R_2$, $R_3$, $R_4$, $R_5$, $R_6$, $R_7$, $R_8$, $R_9$, n and L as described above.

The present invention therefore also relates to the compounds of the formulae (I) or (I'), or their physiologically acceptable salts and/or stereoisomeric forms for use as pharmaceuticals (or medicaments), to the use of the compounds of the formulae (I) or (I'), or their physiologically acceptable salts and/or stereoisomeric forms for the production of pharmaceuticals for the treatment and/or prevention of diseases associated with Rho-kinase and/or Rho-kinase mediated phosphorylation of myosin light chain phosphatase, i.e. for the treatment and/or prevention of hypertension, pulmonary hypertension, ocular hypertension, retinopathy, glaucoma, peripheral circulatory disorder, peripheral occlusive arterial disease (PAOD), coronary heart disease, angina pectoris, heart hypertrophy, heart failure, ischemic diseases, ischemic organ failure (end organ damage), fibroid lung, fibroid liver, liver failure, nephropathy, including hypertension-induced, non-hypertension-induced, and diabetic nephropathies, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, e.g. neuropathic pain; neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy such as osteoporosis, infection of digestive tracts with bacteria, sepsis, cancer development and progression, e.g. cancers of the breast, colon, prostate, ovaries, brain and lung and their metastases.

The treatment and/or prevention of diseases in humans is a preferred embodiment but also warm blooded animals such as cats, dogs, rats, horses etc. may be treated with the compounds of the present invention.

The present invention furthermore relates to pharmaceutical preparations (or pharmaceutical compositions) which contain an effective amount of at least one compound of the formula (I) or (I'), or its physiologically acceptable salts and/or stereoisomeric forms and a pharmaceutically acceptable carrier, i.e. one or more pharmaceutically acceptable carrier substances (or vehicles) and/or additives (or excipients).

Optionally the physiologically functional derivatives, including the prodrugs, of a compound of the formula (I) or (I') may be utilized in the above mentioned uses and pharmaceutical preparations.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carrier substances and/or additives being used in addition to the compound(s) of the formulae (I) or (I'), or its (their) physiologically acceptable salts and/or its (their) stereoisomeric forms as well as their prodrugs. For the production of pills, tablets, coated tablets and hard gelatin capsules it is possible to use, for example, lactose, corn starch or derivatives thereof, talc, stearic acid or its salts, etc. Carrier substances for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, saline, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical preparations normally contain about 0.5 to about 90% by weight of a compound of the formula (I) or (I'), or their physiologically acceptable salts and/or their stereoisomeric forms. The amount of the active ingredient of the formula (I) or (I') and/or its physiologically acceptable salts and/or its stereoisomeric forms in the pharmaceutical preparations normally is from about 0.5 to about 1000 mg, preferably from about 1 to about 500 mg.

In addition to the active ingredients of the formula (I) or (I') and/or their physiologically acceptable salts and/or stereoisomeric forms and to carrier substances, the pharmaceutical preparations can contain one or more additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formulae (I) and/or (I') and/or their physiologically acceptable salts and/or their stereoisomeric forms. In case a pharmaceutical preparation contains two or more compounds of the formulae (I) and/or (I'), the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formulae (I) or (I') allows a great deal of control over the biological and physico-chemical properties of the compounds and thus allows the selection of such desired compounds. Furthermore, in addition to at least one compound of the formula (I) or (I') and/or its physiologically acceptable salts and/or its stereoisomeric forms, the pharmaceutical preparations can also contain one or more other therapeutically or prophylactically active ingredients.

When using the compounds of the formulae (I) or (I') the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from about 0.01 to about 100 mg/kg, preferably from about 0.1 to about 50 mg/kg, in particular from about 0.1 to about 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

Furthermore, the compounds of the formulae (I) or (I') can be used as synthesis intermediates for the preparation of other compounds, in particular of other pharmaceutical active ingredients, which are obtainable from the compounds of the formula I, for example by introduction of substituents or modification of functional groups.

It is understood that modifications that do not substantially affect the activity of the various embodiments of this invention are included within the invention disclosed herein.

The compounds of the formulae (I) or (I') can be prepared according to the following exemplified compounds without limiting the scope of the claims.

In general, protective groups that may still be present in the products obtained in the coupling reaction are then removed by standard procedures. For example, tert-butyl protecting groups, in particular a tert-butoxycarbonyl group which is a protection form of an amino group, can be deprotected, i.e. converted into the amino group, by treatment with trifluoroacetic acid. As already explained, after the coupling reaction also functional groups can be generated from suitable precursor groups. In addition, a conversion into a physiologically acceptable salt or a prodrug of a compound of the formulae (I) or (I') can then be carried out by known processes.

In general, a reaction mixture containing a final compound of the formula (I) or (I') or an intermediate is worked up and, if desired, the product is then purified by customary processes known to those skilled in the art. For example, a synthesized compound can be purified using well known methods such as crystallization, chromatography or reverse phase-high performance liquid chromatography (RP-HPLC) or other methods of separation based, for example, on the size, charge or hydrophobicity of the compound. Similarly, well known methods such as amino acid sequence analysis, NMR, IR and mass spectrometry (MS) can be used for characterizing a compound of the invention.

Isoquinolinones can by synthesized via a variety of methods. The following general schemes illustrate some of the possible ways to access isoquinolones, but do not limit the present invention.

Scheme 1.

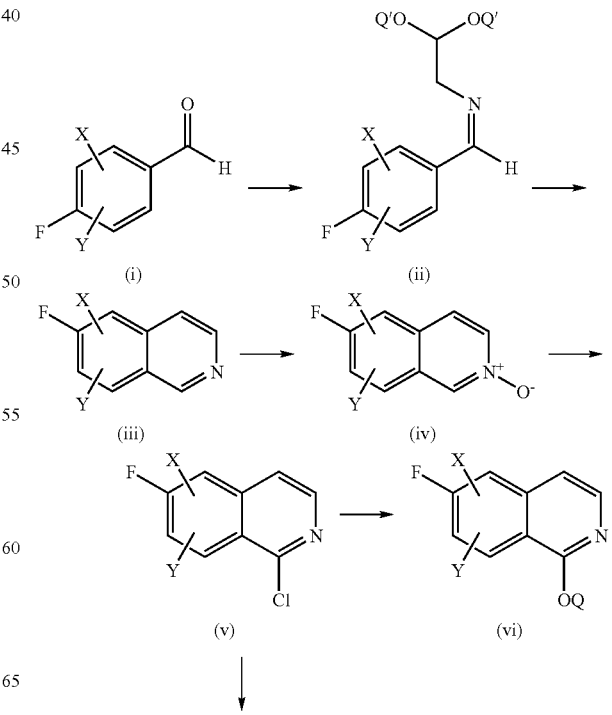

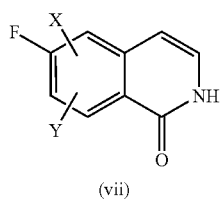

(vii)

A suitably substituted aldehyde, for example substituted by X or Y being independently from each other hydrogen, alkyl, alkoxy or halogen attached in a suitable position, can be reacted with a suitable compound such as for example an acetal of aminoacetaldehyde in a solvent like THF, chloroform or toluene under acid catalysis by toluene sulfonic acid or another appropriate acid to give imine (ii) wherein Q' can be for instance methyl or ethyl, which in turn can be cyclized by different methods to the isoquinoline (iii). For example this can be done by Lewis acid catalysis by suitable Lewis acids like titanium tetrachloride, ferrous halides, aluminium halides etc. at temperatures ranging from ambient to 100° C. or by reducing the imine to the corresponding amine by action of a suitable reducing agent like sodium borohydride, converting the amine into an amide or sulphonamide by reaction with a suitable acid chloride and subsequent cyclization to the isoquinoline by action of an appropriate lewis acid. The isoquinoline (iii) itself can then be converted to the corresponding N-oxide (iv) by action of a suitable oxidative agent like hydrogen peroxide, m-chloro perbenzoic acid or others at room temperature or elevated temperature. The N-oxide (iv) can then be converted into the 1-chloro-isoquinoline derivative (v) by reacting it with a reagent like phosphorous oxy chloride in or without presence of phosphorous pentachloride. The derivative (v) can then be turned into suitable 1-alkoxy-derivatives by reacting it with various alcohols Q-OH like methanol, ethanol or benzyl alcohol in the presence of a suitable base like sodium hydride and in a suitable solvent like dimethyl formamide, dimethyl acetamide or others. Alternatively (v) can be directly converted into the isoquinolinone derivative (vii) by reacting it with a reagent like ammonium acetate.

Scheme 2.

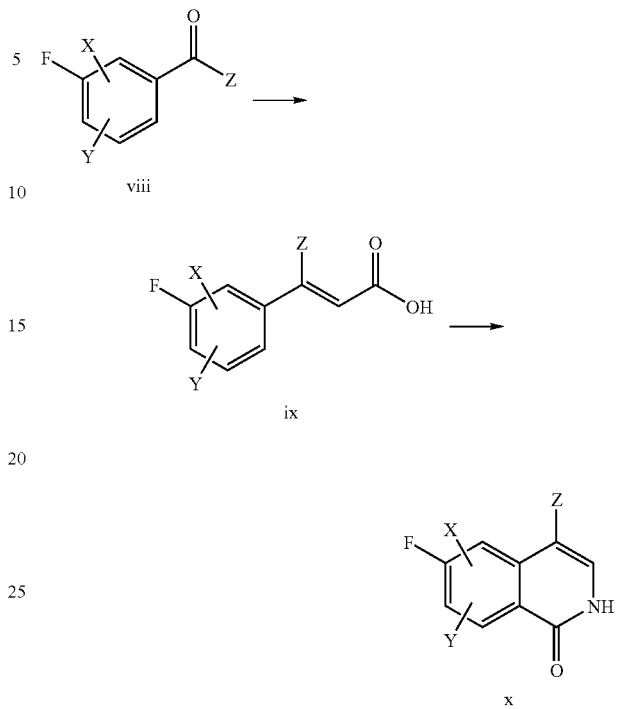

Alternatively isoquinolines can be obtained by reacting suitable 3-formylated or acylated fluorobenzenes (viii), wherein z is for example H or alkyl like methyl or ethyl, with a reagent like triethyl phosphono acetate in the presence of a suitable base like sodium hydride to give the corresponding cinnamic acid ester, which subsequently is cleaved by action of a suitable base like potassium hydroxide, sodium hydroxide or lithium hydroxide in a suitable solvent to deliver acid (ix). (ix) can then be converted in the corresponding acid chloride by well known methods, which can be transferred into the acid azide by reaction with sodium azide in a suitable solvent like ether, chloroform or acetone in or without the presence of water. The corresponding azide then can be converted into isoquinolinone (x) by reacting it in a suitable solvent like diphenylmethane or dipenylether at suitable temperature.

Scheme 3.

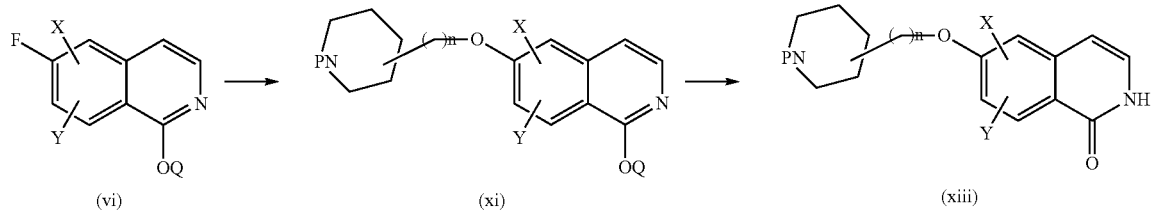

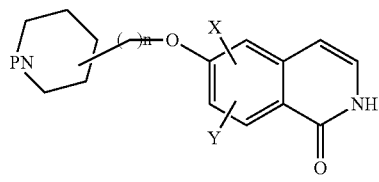

(xii)

The above obtained 6-Fluoro-isoquinolones, for example (vi), can be reacted with suitable P-substituted amino alcohols wherein P is for example hydrogen, alkyl or a protecting group like for example Boc in the presence of base such as DBU, cesium carbonate or sodium hydride to give the corresponding alkoxy substituted derivatives (xi). Eventually, this conversion can already by performed at earlier stages of the synthesis (e.g. by reacting a suitable intermediate). It is understood, that this may require in case of unprotected isoquinolones protection on the nitrogen or oxygen of the isoquinolone moiety by suitable methods, like reaction with suitably substituted alkyl or benzyl halides in the presence of base.

The products like (xi) obtained via this method can then, if a suitable amino functionality is present, be reacted with suitable aldehydes or ketones in the presence of a reducing agent like sodium triacetoxy borohydride, sodium borohydride or sodium cyanoborohydride in a suitable solvent and in the presence of a water withdrawing agent like molecular sieves or a suitable ortho ester. This amino group may have to be liberated in an initial step like for example acidic removal of Boc-groups.

In case of use of protected isoquinolones, cleavage of the used protection groups is required to liberate the desired isoquinolone (xii). This liberation, however, can be performed before or after the reductive amination step, depending on the nature of the used aldehyde/ketone and the protection group used.

Isoquinolone derivatives like (xii) can be obtained as free bases or as various salts like for example hydrochlorides, hydrobromides, phosphates, sulfates or fumarates. The salts obtained can be converted into the corresponding free base by either subjecting them to ion exchange chromatography or for example by alkaline aqueous treatment and subsequent extraction with suitable organic solvents like for example methyl tert. butyl ether, chloroform, ethyl acetate or isopropanol/dichloromethane mixtures and subsequent evaporation to dryness.

The general methods for the preparation of substituted isoquinolone derivatives as described above can be readily adapted to the preparation of the compounds of the formula (I) or formula (I'). In the following examples the preparation of the compounds of the present invention is outlined in more detail. Accordingly, the following examples are part of and intended to illustrate but not to limit the present invention.

(2,2-Dimethoxy-ethyl)-(4-fluoro-benzyl)-amine (1)

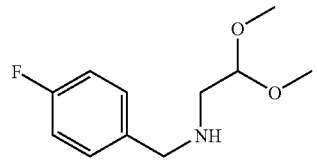

12.4 g of 4-fluorobenzaldehyde were dissolved in 100 mL of toluene and reacted with 10.5 g of 2-aminoacetaldehyde dimethylacetal and 1.90 g (10 mmol) of p-toluenesulfonic acid monohydrate for two hours at a Dean Stark apparatus. The solution was allowed to cool down, extracted with saturated sodium bicarbonate, water and brine, dried over magnesium sulfate and evaporated to dryness. The crude product was dissolved in 100 mL of ethanol. 1.89 g of sodium borohydride were added portionwise. Stirring was continued overnight. For workup, acetic acid was added until no gas evolution could be observed. Then the solution was evaporated to dryness, taken up in dichloromethane and washed twice with water. The organic layer was extracted with brine, dried over magnesium sulfate and evaporated to dryness. The obtained crude product (20 g) was used for further reactions without purification. $R_f$=0.86 min (Method B). Detected mass: 182.1 (M-OMe$^-$), 214.2 (M+H$^+$).

N-(2,2-Dimethoxy-ethyl)-N-(4-fluoro-benzyl)-4-methyl-benzene-sulfonamide (2)

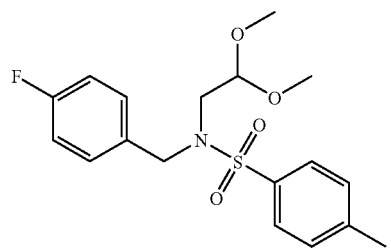

20 g of (2,2-dimethoxy-ethyl)-(4-fluoro-benzyl)-amine (1) were dissolved in 120 mL of dichloromethane. 20 mL of pyridine were added. At 0° C. a solution of 23.8 g p-toluenesulfonic acid chloride in dichloromethane was added dropwise. The reaction was allowed to warm to room temperature and stirring is continued until conversion was completed. For workup, the reaction mixture was extracted twice with 2M hydrochloric acid, twice with sodium bicarbonate and once with brine. The organic layer was dried over magnesium sulfate, evaporated to dryness and the obtained crude product was purified by silica gel chromatography to yield 22.95 g of compound 2 as an orange oil. $R_t$=1.71 min (Method C). Detected mass: 336.1 (M-OMe⁻).

6-Fluoro-isoquinoline (3)

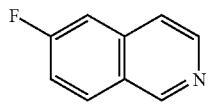

41.6 g of AlCl₃ were suspended in 400 mL of dichloromethane. At room temperature, a solution of 22.95 g of N-(2,2-dimethoxy-ethyl)-N-(4-fluoro-benzyl)-4-methyl-benzenesulfonamide (2) in 150 mL of dichloromethane was added. Stirring was continued at room temperature overnight, the solution was poured on ice, the organic layer was separated, the aqueous phase was extracted twice with dichloromethane and the combined organic layers were then extracted twice with sodium bicarbonate. The organic layer was dried over magnesium sulfate, evaporated to dryness and the obtained crude product (8.75 g) is purified by silica gel chromatography to yield 2.74 g of compound (3). $R_t$=0.30 min (Method C). Detected mass: 148.1 (M+H⁺).

7-Chloro-6-fluoro-isoquinoline (4)

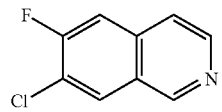

Starting from 3-chloro-4-fluoro-benzaldehyde, the title compound was prepared by the same reaction sequence as used for the synthesis of 6-fluoro-isoquinoline (3). $R_t$=0.77 min (Method A). Detected mass: 182.1/184.1 (M+H⁺).

7-Chloro-6-fluoro-isoquinoline 2-oxide (5)

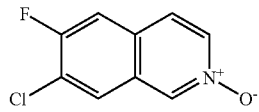

25 g (137.7 mmol) of 7-chloro-6-fluoro-isoquinoline (4) were in dissolved in 500 mL of dichloromethane. At room temperature 50.9 g (206.5 mmol) of m-chloro perbenzoic acid (70%) were added and the mixture was stirred at room temperature until complete conversion iwas achieved. For workup, the precipitate was filtered off and washed with dichloromethane. The filtrate was washed twice with sodium bicarbonate-solution. The layers were separated and the aqueous phase was extracted twice with dichloromethane. The organic phases were dried with MgSO₄ and evaporated.

The so obtained solid material (18.4 g) was used without further purification. $R_t$=0.87 min (Method C). Detected mass: 198.1/200.1 (M+H⁺).

1,7-Di-chloro-6-fluoro-isoquinoline (6)

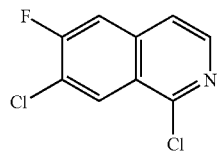

2.6 g (12.0 mmol) of 7-chloro-6-fluoro-isoquinoline 2-oxide (5) were heated in 40 mL of POCl₃ at reflux for 4 h. After the mixture has cooled down to room temperature, it was poured on ice. The aqueous solution was extracted three times with dichloromethane. The combined organic layers were dried with MgSO₄ and evaporated to yield 2.91 g of the title compound, which was used without further purification. $R_t$=2.34 min (Method A). Detected mass: 216.0/218.0 (M+H⁺).

4-(Isoquinolin-6-yloxy)-piperidine-1-carboxylic acid-tert-butylester (7)

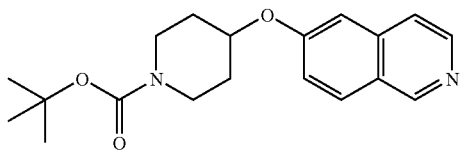

7.49 g of 4-hydroxy-piperidine-1-carboxylic acid-tert-butylester were dissolved in 20 mL of dry dimethyl acetamide. 1.49 g of sodium hydride (60%) were added. Then a solution of 3.65 g of 6-fluoroisoquinoline (3) in dimethyl acetamide was added dropwise. The solution was heated at 80° C. for 2 hours, then the solvent was removed and the residue was taken up in dichloromethane. The organic layer was extracted twice with water and then with brine, dried over magnesium sulfate and evaporated to dryness. The crude product was purified by silica gel chromatography to yield 6.22 g of 4-(isoquinolin-6-yloxy)-piperidine-1-carboxylic acid-tert-butylester (7). $R_t$=1.32 min (Method B). Detected mass: 329.1 (M+H⁺).

4-(2-Oxy-isoquinolin-6-yloxy)-piperidine-1-carboxylic acid tert-butyl ester (8)

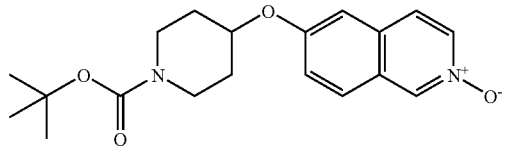

3.97 g (12.1 mmol) of 4-(isoquinolin-6-yloxy)-piperidine-1-carboxylic acid tert-butyl ester (7) were dissolved in 100 mL of dichloromethane and 4.47 g (18.1 mmol) of m-chloro perbenzoic acid (70%) were added at room temperature. The reaction mixture was stirred for 1 h and then washed with saturated sodium bicarbonate solution. The aqueous phase was separated and extracted with dichloromethane. The combined organic layers were dried over magnesium sulfate and evaporated to yield 4.19 g of crude material, which can be used for further conversion without purification. $R_t$=1.46 min (Method B). Detected mass: 345.2 (M+H$^+$).

1-Chloro-6-(piperidin-4-yloxy)-isoquinoline-hydrochloride (9)

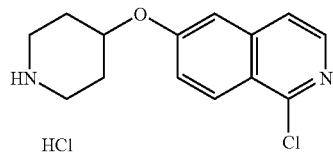

3.5 g (10.16 mmol) of 4-(2-oxy-isoquinolin-6-yloxy)-piperidine-1-carboxylic acid tert-butyl ester (8) were dissolved in 250 mL of HCl-saturated ethanol at 50° C. The clear solution was concentrated i. vac. and the residue was refluxed in 50 mL of POCl$_3$. After 3 h the POCl$_3$ was removed i. vac. and the residue was taken up in water. The pH was adjusted to 11 by adding sodium hydroxide and the aqueous solution was extracted twice with dichloromethane. The combined organic layers were dried over magnesium sulfate and evaporated to dryness. The residue was purified by preparative HPLC, by which the title compound was obtained as trifluoroacetate. This was converted to the corresponding HCl-salt by dissolving the product in 2 N HCl, followed by lyophilization. Yield: 950 mg. $R_t$=1.03 min (Method B). Detected mass: 263.1/265.1 (M+H$^+$).

4-(1-Chloro-isoquinolin-6-yloxy)-piperidine-1-carboxylic acid tert-butyl ester (10)

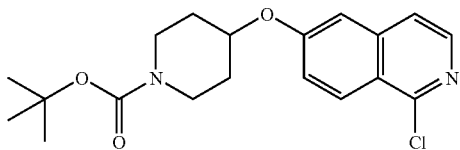

1.23 g (4.11 mmol) of 1-chloro-6-(piperidin-4-yloxy)-isoquinoline hydrochloride (9) were dissolved in 50 mL of dichloromethane and 0.85 mL (6.15 mmol) of triethylamine were added. At 0° C. a solution of 1.09 g (5.0 mmol) of di-tert-butyl-di-carbonate in 10 mL of dichloromethane was added dropwise and the mixture was allowed to stand at room temperature overnight. For workup, the mixture was washed twice with water, dried over magnesium sulfate and evaporated, to yield 1.1 g of the desired product, which could be used without further purification. $R_t$=1.86 min (Method C). Detected mass: 363.1/365.2 (M+H$^+$).

4-(1-Benzyloxy-isoquinolin-6-yloxy)-piperidine-1-carboxylic acid tert-butyl ester (11)

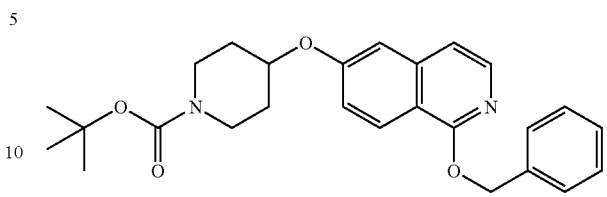

0.70 g (6.49 mmol) of benzyl alcohol were dissolved in 10 mL of dimethyl acetamide. 260 mg (6.49 mmol) of sodium hydride (60%) were added and the solution was stirred at room temperature. After 30 min a solution of 1.57 g (4.33 mmol) of 4-(1-chloro-isoquinolin-6-yloxy)-piperidine-1-carboxylic acid tert-butyl ester (10) in 10 mL of dimethyl acetamide was added and the resulting mixture was heated at 90° C. (bath temperature). After 8 h and standing at room temperature overnight 1.0 additional equivalents of benzyl alcohol and sodium hydride were added and heating at 90° C. was continued for 8 h. For workup, the solvent was removed i. vac. and the residue was dissolved in dichloromethane. The organic solution was washed twice with water, dried with MgSO$_4$ and evaporated. The resulting crude product was purified by preparative HPLC. $R_t$=2.13 min (Method C). Detected mass: 435.2 (M+H$^+$).

6-(Piperidin-4-yloxy)-2H-isoquinolin-1-one (12)

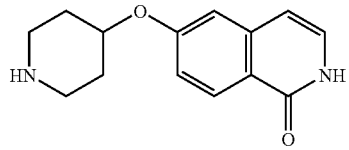

Coumpound (11) was dissolved in ethanol/2 N HCl (1:1) and stirred at room temperature until complete conversion was achieved. The solvent was removed i. vac. and the residue was purified by preparative HPLC. The resulting trifluoroacetate was dissolved in 2 N HCl and lyophilized. After another lyophilization from water, 850 mg of the title compound could be obtained as HCl salt. $R_t$=0.75 min (Method B). Detected mass: 245.1 (M+H$^+$).

Alternative synthetic approach:

6-Fluoro-isoquinolinone (13)

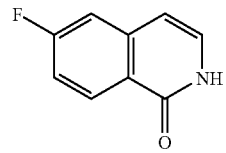

4.8 mL (90.3 mmol, 1.5 eq.) of thionyl chloride was added portionwise to a solution of 10 g (60.2 mmol) of 3-fluoro cinnamic acid in 44 mL of chloroform and 1 mL of DMF. The reaction was heated to reflux for 2.5 h. Then the solvents were distilled to yield 11.4 g of the crude acid chloride, which was used without any further purification.

The acid chloride was dissolved in 45 mL of acetone. At 0° C. 8.03 g of $NaN_3$ (123.5 mmol, 2 eq.) were added portionwise. Then 41 mL of water were added while the temperature was kept below 5° C. The reaction was stirred for another 1.5 h. Then 55 mL of chloroform were added. The mixture was extracted with 80 mL of water followed by 40 mL of brine. After drying over $Na_2SO_4$ and filtration 14 mL of diphenyl ether were added and most of the chloroform was removed in vacuo (without heating). A total removal of the chloroform should be avoided.

The solution containing the azide, diphenyl ether and the remaining chloroform was added dropwise at 260° C. within 15 minutes to a solution of 10 mL of tributyl amine in 97 mL of diphenyl ether. A vigorous reaction can be observed during the addition. The reaction was stirred for another 20 minutes at 260° C. After cooling to room temperature 270 mL of n-heptane were added. The precipitated product was filtered off and washed with ether to yield 5.65 g of the title compound. MS (DCI) Detected mass: 164.0 (M+H$^+$).

6-Fluoro-2-(4-methoxy-benzyl)-2H-isoquinolin-1-one (14)

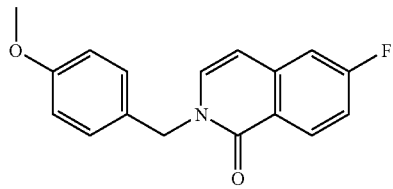

169 μL of p-methoxybenzylchloride (1.24 mmol, 1.1 eq) were added to a suspension of 200 mg of 6-fluoro-isoquinolinone (13) (1.13 mmol) and 368 mg of $Cs_2CO_3$ (1.36 mmol, 1.2 eq) in 3 mL of DMF. The mixture was stirred for 2 h and then poured on ice. The precipitate was filtered, washed with water and dried to yield 300 mg of the title compound. LCMS Method B, retention time 1.76 min, detected mass 284.14 [M+H]$^+$ 6-(Piperidin-4-yloxy)-2H-isoquinolin-1-one (12) and tautomer

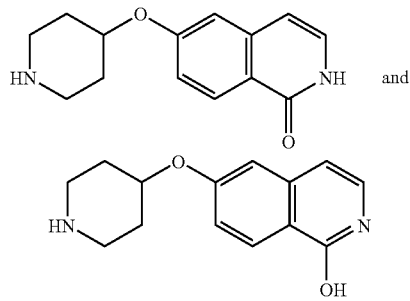

117 mg (0.58 mmol) of 4-hydroxy-piperidine-1-carboxylic acid-tert-butylester were dissolved in 2 mL of N,N-dimethyl acetamide. Under an argon atmosphere, 63.6 mg (2.7 mmol) of sodium hydride were added and the mixture was stirred at room temperature. After 30 minutes, 150 mg (0.53 mmol) of 6-fluoro-2-(4-methoxybenzyl)-2H-isoquinolin-1-one (14) were added and the solution was heated to 80° C. for 1 h. The mixture was poured in water and extracted with chloroform. The combined organic layers were dried over $Na_2SO_4$, filtered and evaporated. The crude intermediate was purified by preparative HPLC. The protecting groups were removed by dissolving the protected intermediate in 2 mL of TFA and heating the reaction to 150° C. for 2 h in a microwave reactor. The reaction mixture was quenched with methanol and evaporated to dryness. The remaining residue was taken up in dichloromethane, extracted three times with 1N HCl and the combined aqueous layer was extracted once with dichloromethane. The combined aqueous layer was lyophilized, the remainder was taken up in water twice and lyophilized again to give the product as HCl salt. The purity of the obtained product is sufficient, but eventually occurring impurities could be removed by silica gel chromatography or HPLC.

7-Bromo-6-fluoro-isoquinoline (15)

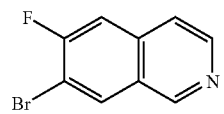

Starting from 3-bromo-4-fluoro-benzaldehyde, the title compound was prepared by the same reaction sequence as used for the synthesis of 6-fluoro-isoquinoline (3). $R_t$=0.91 min (Method B). Detected mass: 226.0/228.0 (M+H$^+$).

7-Methyl-6-(piperidin-4-yloxy)-2H-isoquinolin-1-one (16)

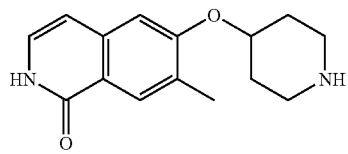

a) 6-Fluoro-7-methyl-2H-isoquinolin-1-one

To a solution of 10.0 g (55.5 mmol) of 3-fluoro-4-methyl-cinnamic acid in 80 mL of acetone were subsequently added at 0° C. 6.74 g (66.6 mmol) of triethylamine in 10 mL of acetone followed by 7.83 g (72.2 mmol) of ethyl chloroformate. After stirring for 2 h at 0 to 5° C. a solution of 4.0 g (61.1 mmol) of sodium azide in 9.5 mL of water was added. After stirring for one additional hour the reaction mixture was poured onto 200 mL of ice water and extraced twice with chloroform. The organic phase was dried over magnesium sulfate, 40 mL of diphenylether were added and the chloroform was cautiously removed in vacuo. The residue was then added dropwise into 50 mL of diphenylether, which had been preheated to 245° C. After complete addition it was stirred for one further hour at 230-250° C. After cooling down to 150° C. the reaction mixture was poured into 270 mL of heptane and after further cooling in an ice bath the precipitated product was filtered by suction and 4.1 g 6-fluoro-7-methyl-2H-isoquinolin-1-one were obtained.

b) 6-Fluoro-2-(4-methoxy-benzyl)-7-methyl-2H-isoquinolin-1-one

To a solution of 9.17 g (51.8 mmol) of 6-fluoro-7-methyl-2H-isoquinolin-1-one in 80 mL of DMF were added 20.2 g (62.1 mmol) cesium carbonate and then 8.92 g (56.9 mmol) 4-methoxybenzylchloride. After stirring at room temperature for 90 minutes the reaction mixture was poured into 600 mL of water, stirred for 1 h, and then the precipitated product was filtrated by suction. From the mother liquor additional producted was isolated by chromatography with heptane/ethyl acetate (80:20). The combined products were recrystallized from ethyl acetate and 8.39 g 6-fluoro-2-(4-methoxy-benzyl)-7-methyl-2H-isoquinolin-1-one were received.

c) 4-[2-(4-Methoxy-benzyl)-7-methyl-1-oxo-1,2-dihydro-isoquinolin-6-yloxy]-piperidine-1-carboxylic acid tert-butyl ester A solution of 3.2 g (15.9 mmol) 1-tert-butoxycarbonyl-4-hydroxypiperidine in 110 mL dimethylacetamide was stirred with 1.36 g (45.4 mmol) of 80-% sodium hydride for 1 h at room temperature. Then a suspension of 4.5 g (15.1 mmol) of 6-fluoro-2-(4-methoxy-benzyl)-7-methyl-2H-isoquinolin-1-one in dimethylacetamide was added. The reaction mixture was heated to 80° C. for 2 h during which time a clear solution was obtained. The reaction mixture was slowly added to 160 mL water and after 1 h of stirring the product was isolated by filtration and dried over night in vacuum. 6.4 g of 4-[2-(4-Methoxy-benzyl)-7-methyl-1-oxo-1,2-dihydro-isoquinolin-6-yloxy]-piperidine-1-carboxylic acid tert-butyl ester were obtained.

d) 7-Methyl-6-(piperidin-4-yloxy)-2H-isoquinolin-1-one hydrochloride 6.4 g (13.4 mmol) 4-[2-(4-methoxy-benzyl)-7-methyl-1-oxo-1,2-dihydro-isoquinolin-6-yloxy]-piperidine-1-carboxylic acid tert-butyl ester were dissolved in 30.5 g (267.4 mmol) trifluoroacetic acid. After 1 h at room temperature the mixture was heated for 2 h in a microwave oven at 150° C. Then the excess trifluoroacetic acid was distilled off in vacuo and the residue was diluted with 130 mL of 1 M hydrochloric acid. The aqueous phase was washed with methylene chloride 3 times and then it was freeze dried to give a hydrochloride, which was crystallized from isopropanol. This furnished 3.2 g 7-methyl-6-(piperidin-4-yloxy)-2H-isoquinolin-1-one (16) as hydrochloride.

$R_t$=1.24 min (Method B). Detected mass: 259.1 (M+H$^+$).

7-Bromo-6-(piperidin-4-yloxy)-2H-isoquinolin-1-one (17)

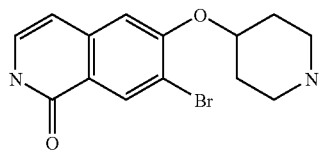

a) 3-(4-Bromo-3-fluoro-phenyl)-acrylic acid ethyl ester

To a solution of 13.4 g (60 mmol) triethyl phosphonoacetate in 80 mL of toluene was added 1.8 g (60 mmol) 80 percent sodium hydride at 0° C. After 30 minutes 11.0 g (54 mmol) 4-bromo-3-fluorobenzaldehyde in 40 mL of toluene were added and the resulting thick mixture was stirred with a mechanical stirrer overnight. After dilution with 500 mL of ethyl acetate and 200 mL of water the organic phase was separated and washed with sodium bicarbonate solution and brine. After drying over magnesium sulfate followed by evaporation and purification by flash chromatography 10.6 g of 3-(4-bromo-3-fluoro-phenyl)-acrylic acid ethyl ester were obtained.

b) 3-(4-Bromo-3-fluoro-phenyl)-acrylic acid 10.5 g (38.6 mmol) of 3-(4-bromo-3-fluoro-phenyl)-acrylic acid ethyl ester were dissolved in 100 mL of methanol and stirred overnight with 97 mL of aqueous 1 M sodium hydroxide solution. After removal of the methanol in vacuo the residue was acidified with concentrated hydrochloric acid. The precipitate was isolated by suction and dried in vacuo at 50° C. furnishing 8.0 g of 3-(4-bromo-3-fluoro-phenyl)-acrylic acid.

c) 7-Bromo-6-fluoro-2H-isoquinolin-1-one

To a solution of 4.0 g (16.3 mmol) of 3-(4-bromo-3-fluoro-phenyl)-acrylic acid in 60 mL acetone were subsequently added at 0-5° C. 2.0 g (19.6 mmol) triethylamine in 10 mL of acetone followed by 2.3 g (21.2 mmol) of ethyl chloroformate in 10 mL of acetone. After stirring for 1 h at 0-5° C. a solution of 1.6 g (24.5 mmol) of sodium azide in 9 mL of water was added. After stirring for 1 additional h the reaction mixture was poured onto 200 mL ice water and extraced with chloroform twice. The organic phase was dried over magnesium sulfate, 24 mL of diphenylether were added and the chloroform was cautiously removed in vacuo. The residue was then added dropwise into 60 mL of diphenylether, which had been preheated to 250° C. After complete addition the reaction mixture was stirred for additional 30 minutes at 230-250° C. After cooling down to 100° C. the reaction mixture was poured into 100 mL of heptane and after further cooling in an ice bath the precipitated product was filtered by suction and 2.4 g of crude 7-bromo-6-fluoro-2H-isoquinolin-1-one were obtained.

d) 7-Bromo-6-fluoro-2-(4-methoxy-benzyl)-2H-isoquinolin-1-one

From 2.4 g of crude 7-bromo-6-fluoro-2H-isoquinolin-1-one, 3.9 g (11.9 mmol) of cesium carbonate and 1.7 g (10.9 mmol) of 4-methoxybenzylchloride were obtained 0.93 g of 7-bromo-6-fluoro-2-(4-methoxy-benzyl)-2H-isoquinolin-1-one analogous to the procedure described in step b of example 16.

e) 7-Bromo-6-(piperidin-4-yloxy)-2H-isoquinolin-1-one-hydrochloride

From 0.93 g (2.6 mmol) of 7-bromo-6-fluoro-2-(4-methoxy-benzyl)-2H-isoquinolin-1-one and 0.54 g (2.7 mmol) of 1-tert-butoxycarbonyl-4-hydroxypiperidine were obtained 0.35 g of 7-bromo-6-(piperidin-4-yloxy)-2H-isoquinolin-1-one as hydrochloride analogous to the procedures described in steps c and d of example 16.

$R_t$=0.80 min (Method A). Detected mass: 323.1/325.1 (M+H$^+$).

Cis and trans N-Boc-2-methyl-piperidin-4-ol (18 and 19)

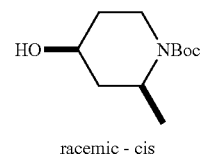

racemic - cis

-continued

19

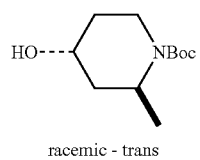

racemic - trans 213 mg (5.6 mmol) of NaBH₄ were added portionwise at 0° C. to a solution of 1.0 g (4.7 mmol) 1-boc-2-methyl-piperidin-4-on in 10 mL of ethanol. The mixture was stirred at room temperature for 2 h. The solvent was removed by distillation and the remainder was dissolved in water and ethyl acetate. The aqueous layer was extracted twice with ethyl acetate and the combined organic layers were dried over Na₂SO₄. After filtration the solvent was removed by distillation and the crude product was purified by column chromatography (n-heptane/ethyl acetate 1/1) to yield 367 mg (36%) of the cis-isomer 18 and 205 mg (20%) of the trans-isomer 19 in addition to 97 mg (10%) mixture of both isomers.

Cis-Isomer (18)

$^1$H-NMR (CDCl$_3$): δ=4.28 (1H, m), 4.17 (1H, m), 3.82 (1H, m), 3.26 (1H, m), 1.85 (1H, ddd, J=14.7, 6.6, und 3.4 Hz), 1.77 (1H, m), 1.66 (2H, m), 1.33 (3H, d, J=7.1 Hz).

Trans-Isomer (19)

$^1$H-NMR (CDCl$_3$): δ=4.50 (1H, m), 4.04 (1H, m), 3.95 (1H, m), 2.87 (1H, dt, J=2.9 und 13.6 Hz), 1.93 (1H, m), 1.83 (1H, m), 1.53 (1H, m), 1.32 (1H, m), 1.14 (3H, d, J=7.1 Hz).

1-Cyclopropyl-piperidin-4-ol (20)

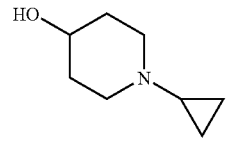

5 g of 4-hydroxypiperidine were dissolved in methanol. 23.8 mL of 1[(1-ethoxycyclopropyl)oxy]trimethylsilane and 5.8 g of sodium cyano borohydride were added and the mixture was reacted at 60° C. for 12 h. The same amounts of the two reagents were added again and stirring was continued at 60° C. for another 12 h. The mixture was diluted with methanol, filtered over celite and evaporated to dryness. The residue was taken up in ethyl acetate, extracted twice with 2N sodium hydroxide and once with brine, dried over sodium sulfate and evaporated to dryness. The residue was purified by silica gel chromatography to yield 2 g of product 20, MS: 141 (M⁺)

The following compounds were obtained as their HCl salt in a similar fashion as described in the syntheses of 12, 16 or 17, starting from the acids and amines listed in the subsequent Table 1.

The used acrylic acids were either commercially available or synthesized from the corresponding aldehydes in similar fashion as described in the literature (see for instance: J. Med. Chem. 2005, 48, 71-90). One example is described in the synthesis of 17, step a.

TABLE 1

| Example | Acid | Amine | Product | [M + H⁺]/ | R$_f$/[min] | Method |
|---|---|---|---|---|---|---|
| 21 | 3-(3-Fluoro-phenyl)-but-2-enoic acid | | | 259.3 | 0.85 | B |
| 22 | 3-(3,4-Difluoro-phenyl)-but-2-enoic acid | | | 277.2 | 0.80 | B |
| 23 | 3,3-Difluoro cinnamic acid | | | 263.1 | 0.77 | B |
| 24 | 3-Fluoro-4-trifluoromethyl cinnamic acid | | | 313.3 | 0.92 | B |

TABLE 1-continued

| Example | Acid | Amine | Product | [M + H⁺]/ | $R_t$/ [min] | Method |
|---|---|---|---|---|---|---|
| 25 | 3-Fluoro-4-methoxy cinnamic acid | HO-piperidine-NBoc | 6-(piperidin-4-yloxy)-7-methoxy-isoquinolin-1(2H)-one | 275.4 | 0.32 | D |
| 26 | 3-(2,3-Difluoro-phenyl)-but-2-enoic acid | HO-piperidine-NBoc | 4-methyl-5-fluoro-6-(piperidin-4-yloxy)-isoquinolin-1(2H)-one | 277.46 | 1.00 | D |
| 27 | 3-(3-Fluoro-4-trifluoromethyl phenyl)-but-2-enoic acid | HO-piperidine-NBoc | 4-methyl-6-(piperidin-4-yloxy)-7-CF₃-isoquinolin-1(2H)-one | 327.2 | 0.97 | B |
| 28 | 3-(3-Fluoro-4-methyl phenyl)-but-2-enoic acid | HO-piperidine-NBoc | 4-methyl-6-(piperidin-4-yloxy)-7-methyl-isoquinolin-1(2H)-one | 273.0 | 0.89 | B |
| 29 | 3-Fluoro cinnamic acid | HOCH₂-piperidine-NBoc | 6-(piperidin-4-ylmethoxy)-isoquinolin-1(2H)-one | 259.3 | 0.89 | B |
| 30 | 3-(2,3-Difluoro-phenyl)-pent-2-enoic acid | HO-piperidine-NBoc | 4-ethyl-5-fluoro-6-(piperidin-4-yloxy)-isoquinolin-1(2H)-one | 291.0 | 1.06 | B |
| 31 | 3-(3-Fluoro-phenyl)-pent-2-enoic acid | HO-piperidine-NBoc | 4-ethyl-6-(piperidin-4-yloxy)-isoquinolin-1(2H)-one | 273.1 | 1.33 | D |

TABLE 1-continued

| Example | Acid | Amine | Product | [M + H⁺]/ | R_f/ [min] | Method |
|---|---|---|---|---|---|---|
| 32 | 3-(3,4-Difluoro-phenyl)-pent-2-enoic acid | HO—⟨piperidine⟩—NBoc | 4-ethyl-7-fluoro-6-(piperidin-4-yloxy)isoquinolin-1(2H)-one | 291.1 | 0.88 | A |
| 33 | 3-Fluoro cinnamic acid | 19 | 6-((2-methylpiperidin-4-yl)oxy)isoquinolin-1(2H)-one (cis) | 259.2 | 0.78 | B |
| 34 | 3-Fluoro cinnamic acid | 18 | 6-((2-methylpiperidin-4-yl)oxy)isoquinolin-1(2H)-one | 259.2 | 0.75 | B |
| 35 | 3-Fluor-4-Methoxy cinnamic acid | 1-methyl-4-hydroxypiperidine | 7-methoxy-6-((1-methylpiperidin-4-yl)oxy)isoquinolin-1(2H)-one | 289.5 | 0.62 | D |
| 36 | 3-(2,3-Difluoro-phenyl)-but-2-enoic acid | 1-methyl-4-hydroxypiperidine | 5-fluoro-4-methyl-6-((1-methylpiperidin-4-yl)oxy)isoquinolin-1(2H)-one | 291.2 | 1.00 | B |
| 37 | 3-(3-Fluoro-4-methyl phenyl)-but-2-enoic acid | 1-methyl-4-hydroxypiperidine | 4,7-dimethyl-6-((1-methylpiperidin-4-yl)oxy)isoquinolin-1(2H)-one | 287.2 | 0.95 | B |

TABLE 1-continued

| Example | Acid | Amine | Product | [M + H⁺]/ | R$_t$/ [min] | Method |
|---|---|---|---|---|---|---|
| 38 | 3-(2,3-Difluoro-phenyl)-pent-2-enoic acid | 1-methyl-4-hydroxypiperidine | 4-ethyl-5-fluoro-6-(1-methylpiperidin-4-yloxy)isoquinolin-1(2H)-one | 305.2 | 0.97 | B |
| 39 | 3-(3-Fluoro-phenyl)-pent-2-enoic acid | 1-methyl-4-hydroxypiperidine | 4-ethyl-6-(1-methylpiperidin-4-yloxy)isoquinolin-1(2H)-one | 287.2 | 0.87 | B |
| 40 | 3-Fluoro cinnamic acid | 1-methyl-4-hydroxypiperidine | 6-(1-methylpiperidin-4-yloxy)isoquinolin-1(2H)-one | 259.3 | 0.72 | C |
| 41 | 3-Fluoro cinnamic acid | 20 | 6-(1-cyclopropylpiperidin-4-yloxy)isoquinolin-1(2H)-one | 285.2 | 0.77 | A |
| 42 | 3-(3-Fluoro-4-trifluoromethyl phenyl)-but-2-enoic acid | 1-methyl-4-hydroxypiperidine | 4-methyl-6-(1-methylpiperidin-4-yloxy)-7-trifluoromethyl-isoquinolin-1(2H)-one | 341.2 | 0.91 | C |
| 43 | 3-Fluoro-4-methyl cinnamic acid | 3-hydroxy-N-Boc-piperidine | 7-methyl-6-(piperidin-3-yloxy)isoquinolin-1(2H)-one | 259.2 | 0.82 | B |
| 44 | 3-Fluoro-4-methyl cinnamic acid | 1-methyl-4-hydroxypiperidine | 7-methyl-6-(1-methylpiperidin-4-yloxy)isoquinolin-1(2H)-one | 273.2 | 0.83 | B |

TABLE 1-continued

| Example | Acid | Amine | Product | [M + H⁺]/ | R_f/ [min] | Method |
|---------|------|-------|---------|-----------|------------|--------|
| 45 | 3-Fluoro cinnamic acid | | | 245.2 | 0.75 | B |
| (R)-45 | 3-Fluoro cinnamic acid | | | 245.2 | 0.78 | B |
| 46 | 4-Chloro-3-fluoro cinnamic acid | | | 279.1 | 0.86 | B |
| 47 | 3-(3-Fluoro-4-methyl phenyl)-but-2-enoic acid | | | 273.2 | 0.81 | A |
| 48 | 3-Fluoro cinnamic acid | | | 259.2 | 0.85 | B |

TABLE 1-continued

| Example | Acid | Amine | Product | [M + H⁺]/ | R$_f$/[min] | Method |
|---|---|---|---|---|---|---|
| 49 | 3-Fluoro cinnamic acid | 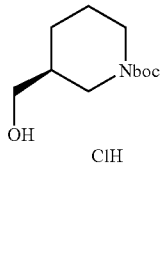 | 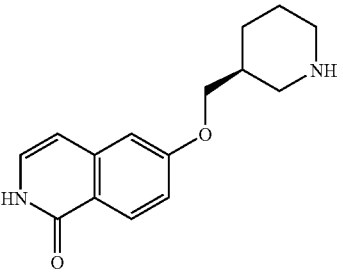 | 259.1 | 0.95 | B |
| 50 | 3-Fluoro cinnamic acid | 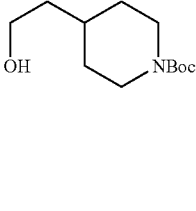 | 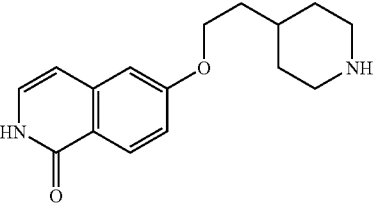 | 273 | 0.92 | A |
| 51 | 3-Fluoro cinnamic acid | 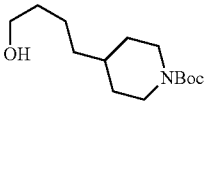 | 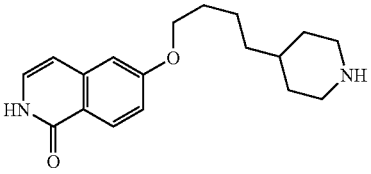 | 301.5 | 1.25 | D |

4-Bromo-6-(piperidin-4-yloxy)-2H-isoquinolin-1-one (52)

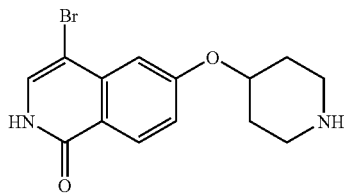

200 mg of (12) were suspended in 25 mL of chloroform. 100 μL of triethylamine was added and stirring was continued for 2 h. The solution was evaporated and the residue was purified by silica gel chromatography (dichloromethane:methanol:triethylamine 10:1:0.1). Another purification by HPLC and changing the anion to HBr yielded 73 mg of product as hydrobromide. R$_f$=1.35 min (Method A). Detected mass: 407.1/409.1 (M+H⁺).

4-(1-Benzyloxy-7-chloro-isoquinolin-6-yloxy)-piperidine-1-carboxylic acid tert-butyl-ester (53)

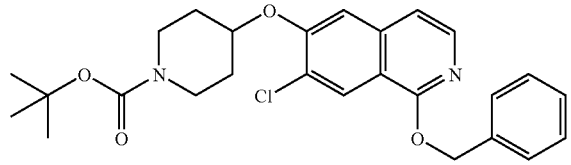

289.8 mg (1.44 mmol) of 4-Hydroxy-piperidine-1-carboxylic acid tert-butyl-ester were dissolved in 10 mL of dimethyl acetamide and 57.6 mg (1.44 mmol) of sodium hydride (60%) were added. The reaction mixture was stirred at room temperature. After 30 minutes a solution of 310 mg (1.44 mmol) of 1,7-di-chloro-6-fluoro-isoquinoline (6) in 3 mL of dimethyl acetamide was added and the mixture was stirred at room temperature for 1 h to complete conversion. Then 155.7 mg (1.44 mmol) of benzyl alcohol followed by 57.6 mg (1.44 mmol) of sodium hydride (60%) were added and stirring was continued at room temperature. To reach complete conversion, 0.5 equivalents of benzyl alcohol and sodium hydride were added twice, after 2 h and standing overnight. For working up, the solvent was evaporated, the residue was taken up in dichloromethane, washed twice with water, dried with MgSO$_4$ and evaporated. Final purification was accomplished by preparative HPLC.

7-Chloro-6-(piperidin-4-yloxy)-2H-isoquinolin-1-one (54) and tautomer

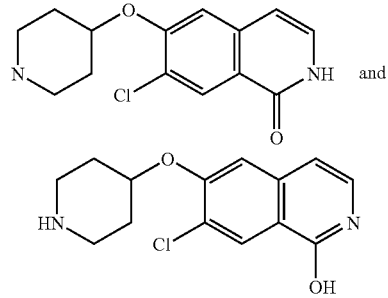

254 mg (0.52 mmol) of 4-(1-benzyloxy-7-chloro-isoquinolin-6-yloxy)-piperidine-1-carboxylic acid tert-butylester (53) were stirred in methanol/2 N HCl (1:1) at room temperature overnight. The solvent was removed i. vac. and the residue was purified by preparative HPLC. The product fractions were evaporated and dissolved in 2 N HCl. Lyophilization results in 57 mg of the desired compound as hydrochloride. $R_t$=0.95 min (Method B). Detected mass: 279.1 (M+H$^+$).

7-Chloro-6-(1-isopropyl-piperidin-4-yloxy)-2H-isoquinolin-1-one (55) and tautomer

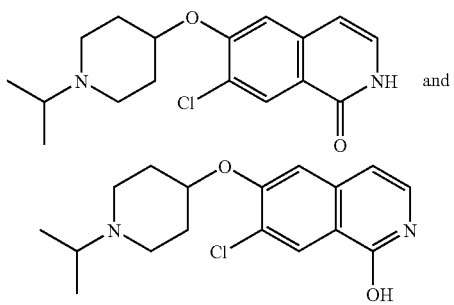

64 mg (0.23 mmol) of 7-chloro-6-(piperidin-4-yloxy)-2H-isoquinolin-1-one-hydro-chloride (54) were dissolved in 5 mL of methanol. 41.4 mg (0.41 mmol) of triethyl amine were added and the mixture stirred at room temperature for 10 minutes. After adding freshly dried molecular sieves, 122.4 mg (2.04 mmol) acetic acid, 26.7 mg (0.46 mmol) of acetone and 43.3 mg (0.69 mmol) of sodium cyanoborohydride, the reaction mixture was refluxed for 8 h. After the addition of 2 equivalents acetone and 2 equivalents of sodium cyanoborohydride at room temperature, the reaction was refluxed for another 2 h to complete conversion. For working up, the mixture was filtered and the filtrate was evaporated. The residue was dissolved in dichloromethane, washed twice with 2 N NaOH and water and dried over MgSO$_4$. After evaporation of the solvent and purification by preparative HPLC, 13 mg of the title compound were obtained as trifluoroacetate. $R_t$=0.96 min (Method B). Detected mass: 321.1/323.2 (M+H$^+$).

General Procedure A for the Reductive Amination Reaction:

0.243 mmol of 6-(piperidin-4-yloxy)-2H-isoquinolin-1-one-hydrochloride (12) or of another suitable amine, 0.243 mmol of the aldehyde and 0.365 mmol triethylamine are stirred in 3 mL HC(OMe)$_3$ for 1 h at room temperature. The mixture is cooled to −10° C., 1.75 mL of a freshly prepared DMF solution containing 1.215 mmol NaHB(OAc)$_3$ and 1.215 mmol HOAc is added. Stirring is continued at −10° C. for 30 min, the mixture is then allowed to warm to room temperature and left at room temperature over night. 0.5 mL of water is added and the mixture is evaporated, dissolved in DMF and purified by preparative HPLC. The purified products are dissolved in 1 mL HCl in isopropanol (5-6M) and left over night at room temperature (cleaves BOC/tBu ester groups of some of the products). 2 mL water is added and the solution is freeze-dried to yield the hydrochlorides of the products.

The following compounds shown in the subsequent Table 2 were synthesized in a similar fashion as described in this general procedure and obtained as hydrochloride salts:

TABLE 2

| Example | Aldehyde or Ketone | Amine | Product | [M + H$^+$] | $R_t$/ [min] | Method |
|---|---|---|---|---|---|---|
| 56 | ![acetaldehyde] | 12 | ![product 56] | 273.2 | 0.75 | B |
| 57 | ![propanal] | 12 | ![product 57] | 287.2 | 0.89 | B |
| 58 | ![cyclopropanecarbaldehyde] | 12 | ![product 58] | 299.2 | 0.97 | B |
| 59 | ![butanal] | 12 | ![product 59] | 301.2 | 0.95 | B |

TABLE 2-continued

| Example | Aldehyde or Ketone | Amine | Product | [M + H⁺] | R_t/ [min] | Method |
|---|---|---|---|---|---|---|
| 60 | isobutyraldehyde | 12 | 6-((1-isobutylpiperidin-4-yl)oxy)isoquinolin-1(2H)-one | 301.2 | 0.98 | B |
| 61 | 3,3,3-trifluoropropanal | 12 | 6-((1-(3,3,3-trifluoropropyl)piperidin-4-yl)oxy)isoquinolin-1(2H)-one | 341.1 | 0.91 | B |
| 62 | 4-chlorobenzaldehyde | 12 | 6-((1-(4-chlorobenzyl)piperidin-4-yl)oxy)isoquinolin-1(2H)-one | 369.1 | 1.17 | B |
| 63 | 3-chlorobenzaldehyde | 12 | 6-((1-(3-chlorobenzyl)piperidin-4-yl)oxy)isoquinolin-1(2H)-one | 369.2 | 1.17 | B |
| 64 | 2-chlorobenzaldehyde | 12 | 6-((1-(2-chlorobenzyl)piperidin-4-yl)oxy)isoquinolin-1(2H)-one | 369.2 | 1.08 | B |
| 65 | 2,4-dichlorobenzaldehyde | 12 | 6-((1-(2,4-dichlorobenzyl)piperidin-4-yl)oxy)isoquinolin-1(2H)-one | 403.2/ 405.2 | 1.21 | A |
| 66 | benzaldehyde | 12 | 6-((1-benzylpiperidin-4-yl)oxy)isoquinolin-1(2H)-one | 335.2 | 1.02 | A |
| 67 | 3,5-dichlorobenzaldehyde | 12 | 6-((1-(3,5-dichlorobenzyl)piperidin-4-yl)oxy)isoquinolin-1(2H)-one | 403.2/ 405.2 | 1.29 | A |
| 68 | 4-methylbenzaldehyde | 12 | 6-((1-(4-methylbenzyl)piperidin-4-yl)oxy)isoquinolin-1(2H)-one | 349.2 | 1.11 | A |

TABLE 2-continued

| Example | Aldehyde or Ketone | Amine | Product | [M + H+] | Rt/ [min] | Method |
|---|---|---|---|---|---|---|
| 69 | 4-(trifluoromethyl)benzaldehyde | 12 | | 403.2 | 1.24 | A |
| 70 | isonicotinaldehyde (pyridine-4-carbaldehyde) | 12 | | 336.2 | 0.60 | A |
| 71 | nicotinaldehyde (pyridine-3-carbaldehyde) | 12 | | 336.2 | 0.62 | A |
| 72 | 4-(methylsulfonyl)benzaldehyde | 12 | | 413.2 | 0.88 | A |
| 73 | 2-naphthaldehyde | 12 | | 385.2 | 1.35 | A |
| 74 | 1-naphthaldehyde | 12 | | 385.2 | 1.27 | A |
| 75 | 1H-indazole-3-carbaldehyde | 12 | | 375.2 | 1.06 | A |
| 76 | thiophene-3-carbaldehyde | 12 | | 341.2 | 0.92 | A |

TABLE 2-continued

| Example | Aldehyde or Ketone | Amine | Product | [M + H⁺] | R$_t$/ [min] | Method |
|---|---|---|---|---|---|---|
| 77 | | 12 | | 342.3 | 0.66 | A |
| 78 | | 12 | | 356.3 | 0.63 | A |
| 79 | | 12 | Chiral | 328.3 | 0.23 | A |
| 80 | | 12 | | 325.2 | 0.91 | A |
| 81 | | 54 | | 321.1 | 0.96 | B |
| 82 | | 54 | | 335.1 | 1.11 | B |
| 83 | | 54 | | 335.1 | 1.02 | B |
| 84 | | 54 | | 333.1 | 1.05 | B |

TABLE 2-continued

| Example | Aldehyde or Ketone | Amine | Product | [M + H⁺] | R$_t$/ [min] | Method |
|---|---|---|---|---|---|---|
| 85 | 3-methylbutanal | 54 | 7-chloro-6-((1-isopentylpiperidin-4-yl)oxy)isoquinolin-1(2H)-one | 349.1 | 1.15 | B |
| 86 | 3,3,3-trifluoropropanal | 54 | 7-chloro-6-((1-(3,3,3-trifluoropropyl)piperidin-4-yl)oxy)isoquinolin-1(2H)-one | 375.1 | 1.02 | B |
| 87 | cyclohexanecarbaldehyde | 54 | 7-chloro-6-((1-(cyclohexylmethyl)piperidin-4-yl)oxy)isoquinolin-1(2H)-one | 375.1 | 1.24 | B |
| 88 | cyclohexanone | 54 | 7-chloro-6-((1-cyclohexylpiperidin-4-yl)oxy)isoquinolin-1(2H)-one | 361.1 | 1.15 | B |
| 89 | 2,4-dichlorobenzaldehyde | 54 | 7-chloro-6-((1-(2,4-dichlorobenzyl)piperidin-4-yl)oxy)isoquinolin-1(2H)-one | 437.1 | 1.30 | B |
| 90 | benzaldehyde | 54 | 6-((1-benzylpiperidin-4-yl)oxy)-7-chloroisoquinolin-1(2H)-one | 369.4 | 1.23 | B |
| 91 | 3,5-dichlorobenzaldehyde | 54 | 7-chloro-6-((1-(3,5-dichlorobenzyl)piperidin-4-yl)oxy)isoquinolin-1(2H)-one | 437.0 | 1.30 | B |
| 92 | 4-methylbenzaldehyde | 54 | 7-chloro-6-((1-(4-methylbenzyl)piperidin-4-yl)oxy)isoquinolin-1(2H)-one | 383.1 | 1.23 | B |
| 93 | 4-(trifluoromethyl)benzaldehyde | 54 | 7-chloro-6-((1-(4-(trifluoromethyl)benzyl)piperidin-4-yl)oxy)isoquinolin-1(2H)-one | 437.1 | 1.30 | B |

TABLE 2-continued
| Example | Aldehyde or Ketone | Amine | Product | [M + H⁺] | R$_t$/ [min] | Method |
|---|---|---|---|---|---|---|
| 94 | 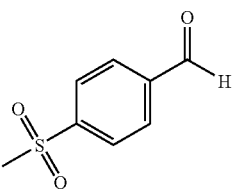 | 54 | 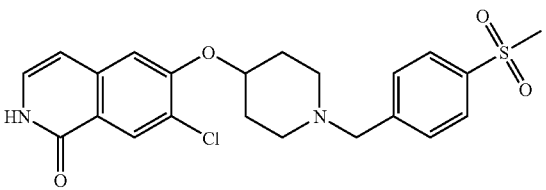 | 447.1 | 1.00 | B |
| 95 | 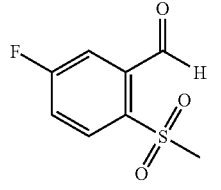 | 54 | 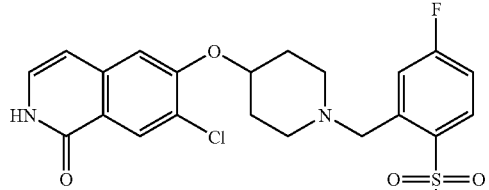 | 465.1 | 1.11 | B |
| 96 | 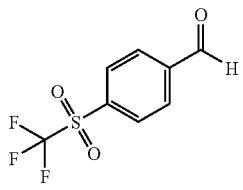 | 54 | 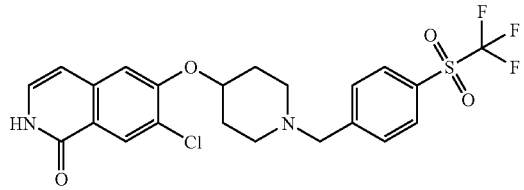 | 501.1 | 1.29 | B |
| 97 | 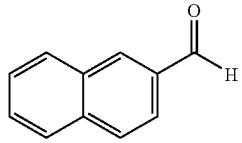 | 54 | 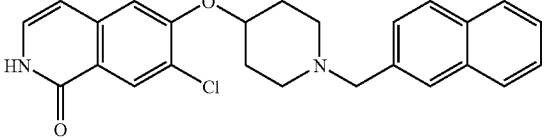 | 419.1 | 1.29 | A |
| 98 | 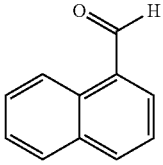 | 54 | 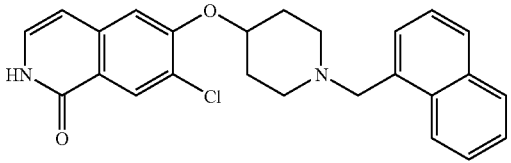 | 419.1 | 1.34 | A |
| 99 |  | 54 | 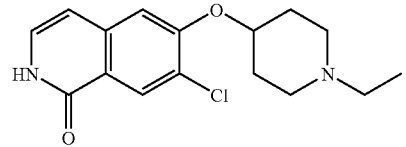 | 307.1 | 0.94 | B |
| 100 | 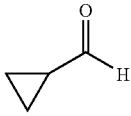 | 23 | 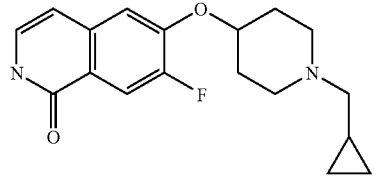 | 317.3 | 0.96 | B |
| 101 | 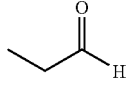 | 23 | 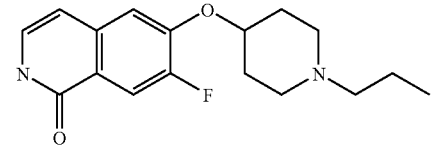 | 305.3 | 0.94 | B |

TABLE 2-continued

| Example | Aldehyde or Ketone | Amine | Product | [M + H⁺] | R_t/ [min] | Method |
|---|---|---|---|---|---|---|
| 102 | acetaldehyde | 21 | 4-methyl-6-(1-ethylpiperidin-4-yloxy)isoquinolin-1(2H)-one | 287.1 | 0.87 | B |
| 103 | propanal | 21 | 4-methyl-6-(1-propylpiperidin-4-yloxy)isoquinolin-1(2H)-one | 301.1 | 0.97 | B |
| 104 | butanal | 21 | 4-methyl-6-(1-butylpiperidin-4-yloxy)isoquinolin-1(2H)-one | 315.2 | 1.00 | B |
| 105 | acetone | 21 | 4-methyl-6-(1-isopropylpiperidin-4-yloxy)isoquinolin-1(2H)-one | 301.2 | 0.96 | B |
| 106 | isobutyraldehyde | 21 | 4-methyl-6-(1-isobutylpiperidin-4-yloxy)isoquinolin-1(2H)-one | 315.2 | 0.97 | B |
| 107 | cyclopropanecarbaldehyde | 21 | 4-methyl-6-(1-(cyclopropylmethyl)piperidin-4-yloxy)isoquinolin-1(2H)-one | 313.2 | 0.99 | B |
| 108 | 3-methylbutanal | 21 | 4-methyl-6-(1-isopentylpiperidin-4-yloxy)isoquinolin-1(2H)-one | 329.2 | 1.13 | B |

TABLE 2-continued

| Example | Aldehyde or Ketone | Amine | Product | [M + H⁺] | R$_t$/ [min] | Method |
|---|---|---|---|---|---|---|
| 109 | F₃C-CH₂-CHO | 21 | 4-methyl-6-[(1-(3,3,3-trifluoropropyl)piperidin-4-yl)oxy]isoquinolin-1(2H)-one | 355.1 | 0.98 | B |
| 110 | cyclohexanone | 21 | 6-[(1-cyclohexylpiperidin-4-yl)oxy]-4-methylisoquinolin-1(2H)-one | 341.2 | 1.09 | B |
| 111 | 4-chlorobenzaldehyde | 21 | 6-[(1-(4-chlorobenzyl)piperidin-4-yl)oxy]-4-methylisoquinolin-1(2H)-one | 383.1<br>385.1 | 1.25 | B |
| 112 | 3-chlorobenzaldehyde | 21 | 6-[(1-(3-chlorobenzyl)piperidin-4-yl)oxy]-4-methylisoquinolin-1(2H)-one | 383.1<br>385.1 | 1.17 | B |
| 113 | 2-chlorobenzaldehyde | 21 | 6-[(1-(2-chlorobenzyl)piperidin-4-yl)oxy]-4-methylisoquinolin-1(2H)-one | 383.1<br>385.1 | 1.15 | B |
| 114 | 2,4-dichlorobenzaldehyde | 21 | 6-[(1-(2,4-dichlorobenzyl)piperidin-4-yl)oxy]-4-methylisoquinolin-1(2H)-one | 417.1<br>419.1 | 1.27 | B |
| 115 | benzaldehyde | 21 | 6-[(1-benzylpiperidin-4-yl)oxy]-4-methylisoquinolin-1(2H)-one | 349.1 | 1.16 | B |

TABLE 2-continued

| Example | Aldehyde or Ketone | Amine | Product | [M + H⁺] | R_t/ [min] | Method |
|---|---|---|---|---|---|---|
| 116 | 3,5-dichlorobenzaldehyde | 21 | 4-methyl-6-[(1-(3,5-dichlorobenzyl)piperidin-4-yl)oxy]isoquinolin-1(2H)-one | 417.1 419.1 | 1.26 | B |
| 117 | 4-methylbenzaldehyde | 21 | 4-methyl-6-[(1-(4-methylbenzyl)piperidin-4-yl)oxy]isoquinolin-1(2H)-one | 363.2 | 1.24 | B |
| 118 | 4-(trifluoromethyl)benzaldehyde | 21 | 4-methyl-6-[(1-(4-(trifluoromethyl)benzyl)piperidin-4-yl)oxy]isoquinolin-1(2H)-one | 417.1 | 1.24 | B |
| 119 | isonicotinaldehyde | 21 | 4-methyl-6-[(1-(pyridin-4-ylmethyl)piperidin-4-yl)oxy]isoquinolin-1(2H)-one | 350.2 | 0.82 | B |
| 120 | butyraldehyde | 23 | 6-[(1-butylpiperidin-4-yl)oxy]-7-fluoroisoquinolin-1(2H)-one | 319.1 | 0.98 | A |
| 121 | acetone | 23 | 7-fluoro-6-[(1-isopropylpiperidin-4-yl)oxy]isoquinolin-1(2H)-one | 305.4 | 0.90 | D |
| 122 | isobutyraldehyde | 23 | 7-fluoro-6-[(1-isobutylpiperidin-4-yl)oxy]isoquinolin-1(2H)-one | 319.1 | 0.88 | A |
| 123 | acetaldehyde | 28 | 6-[(1-ethylpiperidin-4-yl)oxy]-4,7-dimethylisoquinolin-1(2H)-one | 301.2 | 1.00 | B |

TABLE 2-continued

| Example | Aldehyde or Ketone | Amine | Product | [M + H⁺] | R_f / [min] | Method |
|---|---|---|---|---|---|---|
| 124 | propanal | 28 | | 315.2 | 1.07 | B |
| 125 | butanal | 28 | | 329.2 | 1.04 | B |
| 126 | isobutyraldehyde | 28 | | 329.2 | 1.04 | B |
| 127 | cyclopropanecarbaldehyde | 28 | | 327.2 | 1.07 | B |
| 128 | 3-methylbutanal | 28 | | 343.23 | 1.15 | B |
| 129 | 3,3,3-trifluoropropanal | 28 | | 369.1 | 1.02 | B |
| 130 | cyclohexanecarbaldehyde | 28 | | 329.3 | 1.20 | B |

TABLE 2-continued

| Example | Aldehyde or Ketone | Amine | Product | [M + H⁺] | R_t/ [min] | Method |
|---|---|---|---|---|---|---|
| 131 | cyclohexanone | 28 | | 355.2 | 1.13 | B |
| 132 | 4-chlorobenzaldehyde | 28 | | 397.2 | 1.26 | B |
| 133 | 3-chlorobenzaldehyde | 28 | | 397.2 | 1.22 | B |
| 134 | 2-chlorobenzaldehyde | 28 | | 397.2 | 1.21 | B |
| 135 | 2,4-dichlorobenzaldehyde | 28 | | 431.2/ 433.2 | 1.30 | B |
| 136 | benzaldehyde | 28 | | 363.2 | 1.12 | B |
| 137 | 3,5-dichlorobenzaldehyde | 28 | | 431.2/ 433.2 | 1.32 | B |

TABLE 2-continued

| Example | Aldehyde or Ketone | Amine | Product | [M + H⁺] | R$_t$/ [min] | Method |
|---|---|---|---|---|---|---|
| 138 | acetaldehyde | 29 | 6-((1-ethylpiperidin-4-yl)methoxy)isoquinolin-1(2H)-one | 287.1 | 0.82 | B |
| 139 | propanal | 29 | 6-((1-propylpiperidin-4-yl)methoxy)isoquinolin-1(2H)-one | 301.1 | 0.94 | B |
| 140 | butanal | 29 | 6-((1-butylpiperidin-4-yl)methoxy)isoquinolin-1(2H)-one | 315.1 | 0.99 | B |
| 141 | acetone | 29 | 6-((1-isopropylpiperidin-4-yl)methoxy)isoquinolin-1(2H)-one | 301.2 | 0.95 | B |
| 142 | isobutyraldehyde | 29 | 6-((1-isobutylpiperidin-4-yl)methoxy)isoquinolin-1(2H)-one | 315.2 | 0.99 | B |
| 143 | cyclopropanecarbaldehyde | 29 | 6-((1-(cyclopropylmethyl)piperidin-4-yl)methoxy)isoquinolin-1(2H)-one | 313.2 | 0.92 | B |

TABLE 2-continued

| Example | Aldehyde or Ketone | Amine | Product | [M + H⁺] | R_t/ [min] | Method |
|---|---|---|---|---|---|---|
| 144 | isovaleraldehyde | 29 | 6-((1-isopentylpiperidin-4-yl)methoxy)isoquinolin-1(2H)-one | 329.3 | 1.10 | B |
| 145 | 3,3,3-trifluoropropanal | 29 | 6-((1-(3,3,3-trifluoropropyl)piperidin-4-yl)methoxy)isoquinolin-1(2H)-one | 355.1 | 0.94 | B |
| 146 | cyclohexanecarbaldehyde | 29 | 6-((1-(cyclohexylmethyl)piperidin-4-yl)methoxy)isoquinolin-1(2H)-one | 355.2 | 1.18 | B |
| 147 | cyclohexanone | 29 | 6-((1-cyclohexylpiperidin-4-yl)methoxy)isoquinolin-1(2H)-one | 341.2 | 1.08 | B |
| 148 | 4-chlorobenzaldehyde | 29 | 6-((1-(4-chlorobenzyl)piperidin-4-yl)methoxy)isoquinolin-1(2H)-one | 393.1 | 1.18 | B |
| 149 | 3-chlorobenzaldehyde | 29 | 6-((1-(2-chlorobenzyl)piperidin-4-yl)methoxy)isoquinolin-1(2H)-one | 383.1 | 1.14 | B |

TABLE 2-continued

| Example | Aldehyde or Ketone | Amine | Product | [M + H⁺] | R$_t$/ [min] | Method |
|---|---|---|---|---|---|---|
| 150 | benzaldehyde | 29 | (isoquinolinone-O-CH2-piperidine-N-CH2-phenyl) | 349.1 | 1.05 | B |
| 151 | 3,5-dichlorobenzaldehyde | 29 | (isoquinolinone-O-CH2-piperidine-N-CH2-3,5-dichlorophenyl) | 417.1/ 419.1 | 1.25 | B |
| 152 | 4-(trifluoromethyl)benzaldehyde | 29 | (isoquinolinone-O-CH2-piperidine-N-CH2-4-CF3-phenyl) | 417.1 | 1.05 | B |
| 153 | isonicotinaldehyde | 29 | (isoquinolinone-O-CH2-piperidine-N-CH2-4-pyridyl) | 350.2 | 0.74 | B |
| 154 | nicotinaldehyde | 29 | (isoquinolinone-O-CH2-piperidine-N-CH2-3-pyridyl) | 350.2 | 0.80 | B |
| 155 | picolinaldehyde | 29 | (isoquinolinone-O-CH2-piperidine-N-CH2-2-pyridyl) | 350.2 | 0.94 | B |
| 156 | 4-(methylsulfonyl)benzaldehyde | 29 | (isoquinolinone-O-CH2-piperidine-N-CH2-4-SO2Me-phenyl) | 427.1 | 1.06 | B |

TABLE 2-continued

| Example | Aldehyde or Ketone | Amine | Product | [M + H⁺] | R$_t$/ [min] | Method |
|---|---|---|---|---|---|---|
| 157 | 4-(trifluoromethylsulfonyl)benzaldehyde | 29 | | 481.1 | 1.30 | B |
| 158 | propanal | 45 | | 287.2 | 0.83 | B |
| 159 | butanal | 45 | | 301.2 | 0.89 | B |
| 160 | isobutyraldehyde | 45 | | 301.2 | 0.89 | B |
| 161 | cyclopropanecarbaldehyde | 45 | | 299.2 | 0.84 | B |
| 162 | 3-methylbutanal | 45 | | 315.2 | 1.01 | B |
| 163 | 3,3,3-trifluoropropanal | 45 | | 341.1 | 0.98 | B |
| 164 | cyclohexanecarbaldehyde | 45 | | 341.2 | 1.13 | B |
| 165 | 4-chlorobenzaldehyde | 45 | | 369.2 | 1.09 | B |

TABLE 2-continued

| Example | Aldehyde or Ketone | Amine | Product | [M + H+] | R$_t$/[min] | Method |
|---|---|---|---|---|---|---|
| 166 | 3-chlorobenzaldehyde | 45 | isoquinolinone-O-piperidine-CH2-(3-Cl-phenyl) | 369.2 | 1.10 | B |
| 167 | 2-chlorobenzaldehyde | 45 | isoquinolinone-O-piperidine-CH2-(2-Cl-phenyl) | 369.2 | 1.05 | B |
| 168 | 2,4-dichlorobenzaldehyde | 45 | isoquinolinone-O-piperidine-CH2-(2,4-diCl-phenyl) | 403.4/405.4 | 1.36 | D |
| 169 | benzaldehyde | 45 | isoquinolinone-O-piperidine-CH2-phenyl | 335.2 | 1.02 | B |
| 170 | 3,5-dichlorobenzaldehyde | 45 | isoquinolinone-O-piperidine-CH2-(3,5-diCl-phenyl) | 403.1/405.1 | 1.22 | B |
| 171 | 4-methylbenzaldehyde | 45 | isoquinolinone-O-piperidine-CH2-(4-Me-phenyl) | 349.2 | 1.12 | B |
| 172 | 4-trifluoromethylbenzaldehyde | 45 | isoquinolinone-O-piperidine-CH2-(4-CF3-phenyl) | 403.2 | 1.18 | B |
| 173 | isonicotinaldehyde | 45 | isoquinolinone-O-piperidine-CH2-(4-pyridyl) | 336.2 | 0.67 | B |
| 174 | nicotinaldehyde | 45 | isoquinolinone-O-piperidine-CH2-(3-pyridyl) | 336.2 | 0.87 | B |

TABLE 2-continued

| Example | Aldehyde or Ketone | Amine | Product | [M + H⁺] | R_t/ [min] | Method |
|---|---|---|---|---|---|---|
| 175 | pyridine-2-carbaldehyde | 45 | isoquinolinone-O-piperidine-CH2-(2-pyridyl) | 336.2 | 0.95 | B |
| 176 | 4-(methylsulfonyl)benzaldehyde | 45 | isoquinolinone-O-piperidine-CH2-(4-methylsulfonylphenyl) | 413.2 | 0.88 | B |
| 177 | 4-(trifluoromethylsulfonyl)benzaldehyde | 45 | isoquinolinone-O-piperidine-CH2-(4-trifluoromethylsulfonylphenyl) | 431.2 | 0.95 | B |
| 178 | naphthalene-2-carbaldehyde | 45 | isoquinolinone-O-piperidine-CH2-(2-naphthyl) | 385.2 | 1.15 | B |
| 179 | naphthalene-1-carbaldehyde | 45 | isoquinolinone-O-piperidine-CH2-(1-naphthyl) | 385.2 | 1.16 | B |
| 180 | N-Boc-pyrrolidine-2-carbaldehyde | 45 | isoquinolinone-O-piperidine-CH2-(pyrrolidin-3-yl) | 328.2 | 0.68 | B |
| 181 | 1-methyl-1H-pyrrole-3-carbaldehyde | 45 | isoquinolinone-O-piperidine-CH2-(1-methylpyrrol-3-yl) | 338.2 | 0.94 | B |
| 182 | 1-methyl-1H-pyrazole-4-carbaldehyde | 45 | isoquinolinone-O-piperidine-CH2-(1-methylpyrazol-4-yl) | 339.2 | 0.94 | B |

TABLE 2-continued

| Example | Aldehyde or Ketone | Amine | Product | [M + H⁺] | R_t [min] | Method |
|---|---|---|---|---|---|---|
| 183 | indazole-3-carboxaldehyde | 45 | isoquinolinone-O-piperidine-CH2-indazole | 375.2 | 0.99 | B |
| 184 | isovaleraldehyde | 25 | methoxy-isoquinolinone-O-piperidine-N-isopentyl | 346.2 | 0.96 | A |
| 185 | 3,3,3-trifluoropropanal | 25 | methoxy-isoquinolinone-O-piperidine-N-CH2CH2CF3 | 371.2 | 0.82 | A |
| 186 | cyclohexanecarboxaldehyde | 25 | methoxy-isoquinolinone-O-piperidine-N-CH2-cyclohexyl | 371.2 | 1.08 | A |
| 187 | 4-chlorobenzaldehyde | 25 | methoxy-isoquinolinone-O-piperidine-N-CH2-(4-Cl-phenyl) | 399.2 | 1.10 | A |
| 188 | 3-chlorobenzaldehyde | 25 | methoxy-isoquinolinone-O-piperidine-N-CH2-(3-Cl-phenyl) | 399.2 | 1.10 | A |
| 189 | acetaldehyde | 26 | 4-methyl-5-fluoro-isoquinolinone-O-piperidine-N-ethyl | 305.2 | 0.94 | B |
| 190 | butyraldehyde | 26 | 4-methyl-5-fluoro-isoquinolinone-O-piperidine-N-butyl | 333.2 | 1.15 | B |

TABLE 2-continued

| Example | Aldehyde or Ketone | Amine | Product | [M + H⁺] | R_f [min] | Method |
|---|---|---|---|---|---|---|
| 191 | isobutyraldehyde | 26 | 4-methyl-5-fluoro-6-(1-isobutylpiperidin-4-yloxy)isoquinolin-1(2H)-one | 33.2 | 1.05 | B |
| 192 | 3-methylbutanal | 26 | 4-methyl-5-fluoro-6-(1-isopentylpiperidin-4-yloxy)isoquinolin-1(2H)-one | 347.2 | 1.17 | B |
| 193 | 3,3,3-trifluoropropanal | 26 | 4-methyl-5-fluoro-6-(1-(3,3,3-trifluoropropyl)piperidin-4-yloxy)isoquinolin-1(2H)-one | 373.1 | 1.06 | B |
| 194 | cyclohexanecarbaldehyde | 26 | 4-methyl-5-fluoro-6-(1-(cyclohexylmethyl)piperidin-4-yloxy)isoquinolin-1(2H)-one | 373.2 | 1.23 | B |
| 195 | cyclohexanone | 26 | 4-methyl-5-fluoro-6-(1-cyclohexylpiperidin-4-yloxy)isoquinolin-1(2H)-one | 359.2 | 1.17 | B |
| 196 | 4-chlorobenzaldehyde | 26 | 4-methyl-5-fluoro-6-(1-(4-chlorobenzyl)piperidin-4-yloxy)isoquinolin-1(2H)-one | 401.1 | 1.24 | B |
| 197 | 3-chlorobenzaldehyde | 26 | 4-methyl-5-fluoro-6-(1-(2-chlorobenzyl)piperidin-4-yloxy)isoquinolin-1(2H)-one | 401.1 | 1.20 | B |

TABLE 2-continued

| Example | Aldehyde or Ketone | Amine | Product | [M + H⁺] | Rₜ [min] | Method |
|---|---|---|---|---|---|---|
| 198 | 2,4-dichlorobenzaldehyde | 26 | (structure) | 435.1/ 437.1 | 1.30 | B |
| 199 | benzaldehyde | 26 | (structure) | 367.2 | 1.17 | B |
| 200 | 3,5-dichlorobenzaldehyde | 26 | (structure) | 435.1/ 437.1 | 1.31 | B |
| 201 | 4-methylbenzaldehyde | 26 | (structure) | 381.2 | 1.25 | B |
| 202 | 4-(trifluoromethyl)benzaldehyde | 26 | (structure) | 435.1 | 1.31 | B |
| 203 | pyridine-2-carbaldehyde | 26 | (structure) | 368.2 | 0.99 | A |
| 204 | 4-(methylsulfonyl)benzaldehyde | 26 | (structure) | 445.2 | 1.05 | B |

TABLE 2-continued
| Example | Aldehyde or Ketone | Amine | Product | [M + H+] | Rt / [min] | Method |
|---|---|---|---|---|---|---|
| 205 | 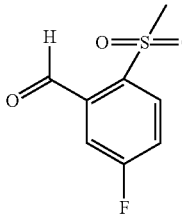 | 26 | 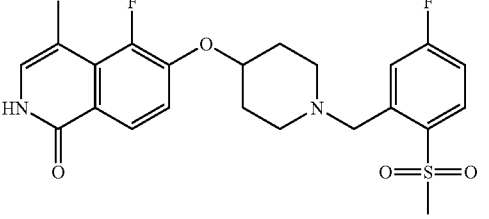 | 463.1 | 1.16 | B |
| 206 | 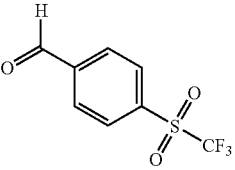 | 26 | 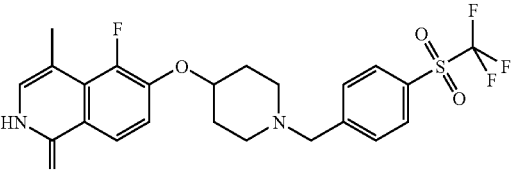 | 499.1 | 1.32 | B |
| 207 | 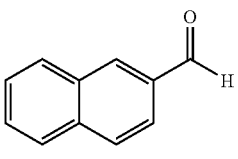 | 26 | 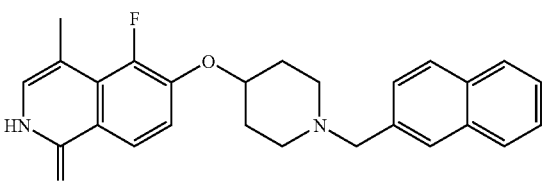 | 417.2 | 1.30 | B |
| 208 | 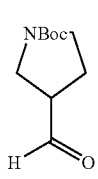 | 26 | 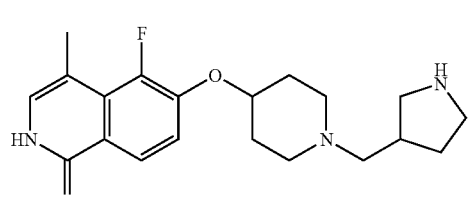 | 360.2 | 0.78 | B |
| 209 | 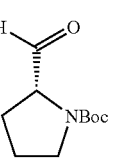 | 26 | 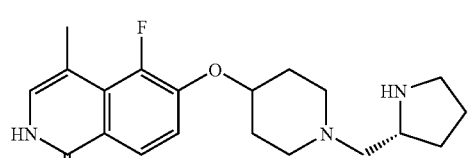 | 360.2 | 0.86 | B |
| 210 |  | 26 | 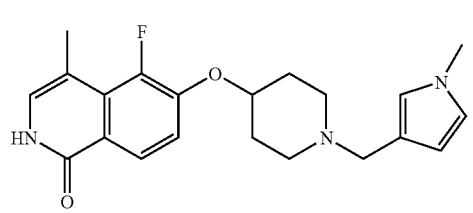 | 370.2 | 1.17 | B |
| 211 |  | 26 | 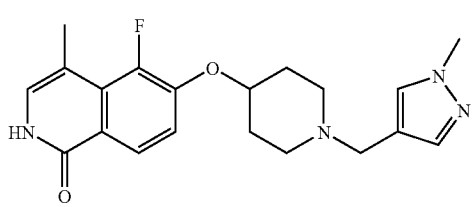 | 371.1 | 1.01 | B |

TABLE 2-continued
| Example | Aldehyde or Ketone | Amine | Product | [M + H+] | Rt/ [min] | Method |
|---|---|---|---|---|---|---|
| 212 | 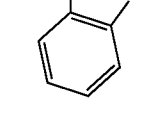 | 26 | 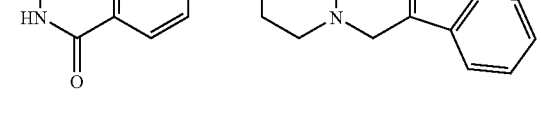 | 407.2 | 1.15 | B |
| 213 | 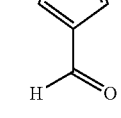 | 26 | 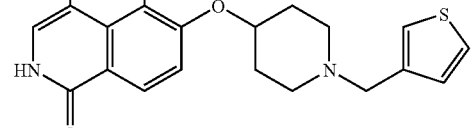 | 373.1 | 1.12 | B |
| 214 | 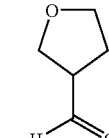 | 26 | 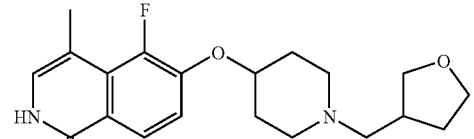 | 361.2 | 1.05 | B |
| 215 | 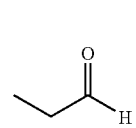 | 31 |  | 315.3 | 0.94 | A |
| 216 | 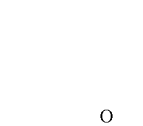 | 31 | 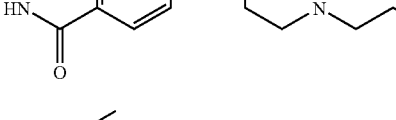 | 329.3 | 1.04 | A |
| 217 | 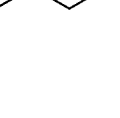 | 31 | 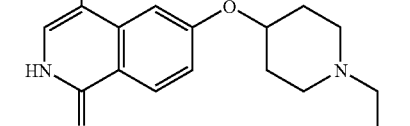 | 329.3 | 1.07 | A |
| 218 | 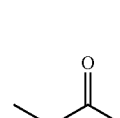 | 31 |  | 327.3 | 0.98 | A |

TABLE 2-continued

| Example | Aldehyde or Ketone | Amine | Product | [M + H⁺] | R_t/ [min] | Method |
|---|---|---|---|---|---|---|
| 219 | isovaleraldehyde | 31 | 4-ethyl-6-(1-isopentylpiperidin-4-yloxy)isoquinolin-1(2H)-one | 343.3 | 1.13 | A |
| 220 | 3,3,3-trifluoropropanal | 31 | 4-ethyl-6-(1-(3,3,3-trifluoropropyl)piperidin-4-yloxy)isoquinolin-1(2H)-one | 369.2 | 1.05 | A |
| 221 | cyclohexanecarbaldehyde | 31 | 6-(1-(cyclohexylmethyl)piperidin-4-yloxy)-4-ethylisoquinolin-1(2H)-one | 369.2 | 1.05 | A |
| 222 | cyclohexanone | 31 | 6-(1-cyclohexylpiperidin-4-yloxy)-4-ethylisoquinolin-1(2H)-one | 355.3 | 1.15 | A |
| 223 | 4-chlorobenzaldehyde | 31 | 6-(1-(4-chlorobenzyl)piperidin-4-yloxy)-4-ethylisoquinolin-1(2H)-one | 397.2 | 1.26 | A |
| 224 | 3-chlorobenzaldehyde | 31 | 6-(1-(3-chlorobenzyl)piperidin-4-yloxy)-4-ethylisoquinolin-1(2H)-one | 397.2 | 1.28 | A |
| 225 | 2-chlorobenzaldehyde | 31 | 6-(1-(2-chlorobenzyl)piperidin-4-yloxy)-4-ethylisoquinolin-1(2H)-one | 397.2 | 1.28 | A |

TABLE 2-continued

| Example | Aldehyde or Ketone | Amine | Product | [M + H⁺] | R_t/ [min] | Method |
|---|---|---|---|---|---|---|
| 226 | benzaldehyde | 31 | | 363.2 | 1.16 | A |
| 227 | 4-methylbenzaldehyde | 31 | | 377.3 | 1.26 | A |
| 228 | 4-(trifluoromethyl)benzaldehyde | 31 | | 431.3 | 431.3 | A |
| 229 | isonicotinaldehyde | 31 | | 364.3 | 0.83 | A |
| 230 | picolinaldehyde | 31 | | 364.3 | 1.06 | A |
| 231 | 4-(methylsulfonyl)benzaldehyde | 31 | | 441.3 | 1.03 | A |
| 232 | 2-naphthaldehyde | 31 | | 413.3 | 1.40 | A |

TABLE 2-continued

| Example | Aldehyde or Ketone | Amine | Product | [M + H+] | R_t/ [min] | Method |
|---|---|---|---|---|---|---|
| 233 | 1-methyl-1H-pyrrole-3-carbaldehyde | 31 | 4-ethyl-6-((1-((1-methyl-1H-pyrrol-3-yl)methyl)piperidin-4-yl)oxy)isoquinolin-1(2H)-one | 366.3 | 1.19 | A |
| 234 | 1H-indazole-3-carbaldehyde | 31 | 4-ethyl-6-((1-((1H-indazol-3-yl)methyl)piperidin-4-yl)oxy)isoquinolin-1(2H)-one | 403.3 | 1.11 | A |
| 235 | thiophene-3-carbaldehyde | 31 | 4-ethyl-6-((1-(thiophen-3-ylmethyl)piperidin-4-yl)oxy)isoquinolin-1(2H)-one | 369.2 | 1.12 | A |
| 236 | acetaldehyde | 30 | 4-ethyl-5-fluoro-6-((1-ethylpiperidin-4-yl)oxy)isoquinolin-1(2H)-one | 319.2 | 1.01 | A |
| 237 | propionaldehyde | 30 | 4-ethyl-5-fluoro-6-((1-propylpiperidin-4-yl)oxy)isoquinolin-1(2H)-one | 333.2 | 1.08 | B |
| 238 | butyraldehyde | 30 | 4-ethyl-5-fluoro-6-((1-butylpiperidin-4-yl)oxy)isoquinolin-1(2H)-one | 347.2 | 1.23 | B |
| 239 | isobutyraldehyde | 30 | 4-ethyl-5-fluoro-6-((1-isobutylpiperidin-4-yl)oxy)isoquinolin-1(2H)-one | 347.2 | 1.18 | B |

TABLE 2-continued

| Example | Aldehyde or Ketone | Amine | Product | [M + H⁺] | R₁/ [min] | Method |
|---|---|---|---|---|---|---|
| 240 | 3,3,3-trifluoropropanal | 30 | (structure) | 387.1 | 1.20 | B |
| 241 | 3-chlorobenzaldehyde | 30 | (structure) | 415.2 | 1.24 | B |
| 242 | 2-chlorobenzaldehyde | 30 | (structure) | 415.2 | 1.27 | B |
| 243 | 3,5-dichlorobenzaldehyde | 30 | (structure) | 449.2/ 451.2 | 1.49 | A |
| 244 | 4-methylbenzaldehyde | 30 | (structure) | 395.2 | 1.32 | B |
| 245 | pyridine-3-carbaldehyde | 30 | (structure) | 382.2 | 1.00 | B |
| 246 | pyridine-2-carbaldehyde | 30 | (structure) | 382.5 | 1.23 | D |

TABLE 2-continued

| Example | Aldehyde or Ketone | Amine | Product | [M + H⁺] | R_t/ [min] | Method |
|---|---|---|---|---|---|---|
| 247 | 2-naphthaldehyde | 30 | | 431.3 | 1.48 | A |
| 248 | cyclohexanecarbaldehyde | 30 | | 387.3 | 1.42 | A |
| 249 | acetaldehyde | 32 | | 319.2 | 0.94 | A |
| 250 | propionaldehyde | 32 | | 333.1 | 0.98 | A |
| 251 | butyraldehyde | 32 | | 347.2 | 1.14 | A |
| 252 | acetone | 32 | | 333.2 | 0.97 | A |
| 253 | isobutyraldehyde | 32 | | 347.1 | 1.05 | A |

TABLE 2-continued

| Example | Aldehyde or Ketone | Amine | Product | [M + H⁺] | R_t/ [min] | Method |
|---|---|---|---|---|---|---|
| 254 | cyclopropanecarbaldehyde | 32 | | 345.2 | 1.04 | A |
| 255 | 3-methylbutanal | 32 | | 361.16 | 1.23 | A |
| 256 | 3,3,3-trifluoropropanal | 32 | | 387.1 | 1.06 | A |
| 257 | cyclohexanecarbaldehyde | 32 | | 387.2 | 1.38 | A |
| 258 | cyclohexanone | 32 | | 373.15 | 1.24 | A |
| 259 | 4-chlorobenzaldehyde | 32 | | 415.1/ 417.1 | 1.31 | A |
| 260 | 3-chlorobenzaldehyde | 32 | | 415.1/ 417.1 | 1.29 | A |

TABLE 2-continued

| Example | Aldehyde or Ketone | Amine | Product | [M + H⁺] | R_t/ [min] | Method |
|---|---|---|---|---|---|---|
| 261 | 2-chlorobenzaldehyde | 32 | 4-ethyl-7-fluoro-6-[(1-(2-chlorobenzyl)piperidin-4-yl)oxy]isoquinolin-1(2H)-one | 415.2/ 417.2 | 1.20 | B |
| 321 | 2,4-dichlorobenzaldehyde | 32 | 4-ethyl-7-fluoro-6-[(1-(2,4-dichlorobenzyl)piperidin-4-yl)oxy]isoquinolin-1(2H)-one | 449.1/ 451.1 | 1.35 | B |
| 262 | benzaldehyde | 32 | 4-ethyl-7-fluoro-6-[(1-benzylpiperidin-4-yl)oxy]isoquinolin-1(2H)-one | 381.2 | 1.22 | B |
| 263 | 3,5-dichlorobenzaldehyde | 32 | 4-ethyl-7-fluoro-6-[(1-(3,5-dichlorobenzyl)piperidin-4-yl)oxy]isoquinolin-1(2H)-one | 449.1/ 451.1 | 1.38 | B |
| 264 | N-Boc-piperidine-4-carbaldehyde | 16 | 7-methyl-6-[(1-(piperidin-4-ylmethyl)piperidin-4-yl)oxy]isoquinolin-1(2H)-one | 356.3 | 0.73 | B |
| 265 | tetrahydrofuran-3-carbaldehyde | 16 | 7-methyl-6-[(1-((tetrahydrofuran-3-yl)methyl)piperidin-4-yl)oxy]isoquinolin-1(2H)-one | 343.2 | 0.94 | B |
| 266 | thiophene-3-carbaldehyde | 16 | 7-methyl-6-[(1-(thiophen-3-ylmethyl)piperidin-4-yl)oxy]isoquinolin-1(2H)-one | 355.1 | 1.05 | B |
| 267 | 1H-indazole-3-carbaldehyde | 16 | 7-methyl-6-[(1-((1H-indazol-3-yl)methyl)piperidin-4-yl)oxy]isoquinolin-1(2H)-one | 389.2 | 1.08 | B |

TABLE 2-continued

| Example | Aldehyde or Ketone | Amine | Product | [M + H⁺] | $R_t$/ [min] | Method |
|---|---|---|---|---|---|---|
| 268 | 1-methyl-1H-pyrazole-3-carbaldehyde | 16 | | 353.2 | 0.90 | B |
| 269 | 1-methyl-1H-pyrrole-3-carbaldehyde | 16 | | 352.2 | 1.05 | B |
| 270 | N-Boc-pyrrolidine-3-carbaldehyde | 16 | | 342.2 | 0.86 | B |
| 271 | 1-naphthaldehyde | 16 | | 399.2 | 1.28 | B |
| 272 | 2-naphthaldehyde | 16 | | 399.2 | 1.26 | B |
| 273 | 4-(trifluoromethylsulfonyl)benzaldehyde | 16 | | 481.2 | 1.28 | B |
| 274 | 3-fluoro-5-(methylsulfonyl)benzaldehyde | 16 | | 445.2 | 1.05 | B |
| 275 | 4-(methylsulfonyl)benzaldehyde | 16 | | 427.2 | 1.07 | B |

TABLE 2-continued

| Example | Aldehyde or Ketone | Amine | Product | [M + H⁺] | R_t / [min] | Method |
|---|---|---|---|---|---|---|
| 276 | pyridine-2-carbaldehyde | 16 | 7-methyl-6-({1-[(pyridin-2-yl)methyl]piperidin-4-yl}oxy)isoquinolin-1(2H)-one | 350.2 | 1.01 | B |
| 277 | pyridine-3-carbaldehyde | 16 | 7-methyl-6-({1-[(pyridin-3-yl)methyl]piperidin-4-yl}oxy)isoquinolin-1(2H)-one | 350.2 | 0.87 | B |
| 278 | pyridine-4-carbaldehyde | 16 | 7-methyl-6-({1-[(pyridin-4-yl)methyl]piperidin-4-yl}oxy)isoquinolin-1(2H)-one | 350.2 | 0.79 | B |
| 279 | 4-(trifluoromethyl)benzaldehyde | 16 | 7-methyl-6-({1-[4-(trifluoromethyl)benzyl]piperidin-4-yl}oxy)isoquinolin-1(2H)-one | 417.2 | 1.25 | B |
| 280 | 4-methylbenzaldehyde | 16 | 7-methyl-6-({1-(4-methylbenzyl)piperidin-4-yl}oxy)isoquinolin-1(2H)-one | 363.2 | 1.18 | B |
| 281 | 3,5-dichlorobenzaldehyde | 16 | 6-({1-(3,5-dichlorobenzyl)piperidin-4-yl}oxy)-7-methylisoquinolin-1(2H)-one | 417.1/ 419.2 | 1.28 | B |
| 282 | benzaldehyde | 16 | 6-({1-benzylpiperidin-4-yl}oxy)-7-methylisoquinolin-1(2H)-one | 349.19 | 1.09 | B |
| 283 | 2,4-dichlorobenzaldehyde | 16 | 6-({1-(2,4-dichlorobenzyl)piperidin-4-yl}oxy)-7-methylisoquinolin-1(2H)-one | 417.13 | 1.25 | B |
| 284 | 2-chlorobenzaldehyde | 16 | 6-({1-(2-chlorobenzyl)piperidin-4-yl}oxy)-7-methylisoquinolin-1(2H)-one | 383.2/ 385.2 | 1.14 | B |

TABLE 2-continued

| Example | Aldehyde or Ketone | Amine | Product | [M + H⁺] | R_t [min] | Method |
|---|---|---|---|---|---|---|
| 285 | 3-chlorobenzaldehyde | 16 | | 383.2/ 385.2 | 1.18 | B |
| 286 | 4-chlorobenzaldehyde | 16 | | 383.2/ 385.2 | 1.18 | B |
| 287 | cyclohexanone | 16 | | 341.2 | 1.15 | B |
| 288 | cyclohexanecarbaldehyde | 16 | | 355.5 | 1.40 | D |
| 289 | 3,3,3-trifluoropropanal | 16 | | 355.5 | 1.18 | D |
| 290 | cyclopropanecarbaldehyde | 16 | | 313.1 | 0.95 | B |
| 291 | isovaleraldehyde | 16 | | 315.5 | 1.23 | D |
| 292 | acetone | 16 | | 301.5 | 1.09 | D |
| 293 | butyraldehyde | 16 | | 315.2 | 1.00 | B |

TABLE 2-continued

| Example | Aldehyde or Ketone | Amine | Product | [M + H+] | Rt/ [min] | Method |
|---|---|---|---|---|---|---|
| 294 | propanal | 16 | 6-((1-propylpiperidin-4-yl)oxy)-7-methyl-2H-isoquinolin-1-one | 301.2 | 1.02 | B |
| 295 | acetaldehyde | 16 | 6-((1-ethylpiperidin-4-yl)oxy)-7-methyl-2H-isoquinolin-1-one | 287.2 | 0.88 | B |
| 296 | 2-(1-Boc-piperidin-4-yl)acetaldehyde | 16 | 6-((1-(2-(piperidin-4-yl)ethyl)piperidin-4-yl)oxy)-7-methyl-2H-isoquinolin-1-one | 370.3 | 0.85 | B |

General Procedure B for the Reductive Amination Reaction:

100 mg (0.25 mmol) 7-Chloro-6-(piperidin-4-yloxy)-2H-isoquinolin-1-one trifluoro-acetate (54, trifluoroacetate) were dissolved in 5 mL Methanol. After adding molecular sieves 4 A, 51.5 mg (0.51 mmol) triethyl amine, 152.9 mg (2.55 mmol) acetic acid and 0.32 mmol of the corresponding aldehyde, a solution of 48.0 mg (0.76 mmol) sodium cyanoboron hydride is added dropwise and the mixture is stirred at room temperature until complete conversion is achieved. In some cases it was necessary to heat the mixture at 60° C. to achieve complete conversion. For the isolation of the products, the solution was filtered and the solvent was removed i. vac. The residue was dissolved in dichloromethane, washed with 1 N NaOH and sat. NaCl-solution, dried with MgSO4 and evaporated. The crude products were purified by preparative HPLC. The obtained trifluoroacetates were stirred in 2 N HCl/Methanol, evaporated, dissolved in water and freeze dried to yield the desired products as hydrochlorides.

The following compounds in Table 3 were synthesized and obtained as hydrochlorides by this procedure using compound 54.

TABLE 3

| Example | Aldehyde | Product | [M + H+] | Rt/ [min] | Method |
|---|---|---|---|---|---|
| 297 | 3-chlorobenzaldehyde | 6-((1-(3-chlorobenzyl)piperidin-4-yl)oxy)-7-chloro-2H-isoquinolin-1-one | 405.1 | 1.20 | B |
| 298 | 3-methylbenzaldehyde | 6-((1-(3-methylbenzyl)piperidin-4-yl)oxy)-7-chloro-2H-isoquinolin-1-one | 383.1 | 1.19 | B |
| 299 | 4-ethylbenzaldehyde | 6-((1-(4-ethylbenzyl)piperidin-4-yl)oxy)-7-chloro-2H-isoquinolin-1-one | 397.1 | 1.28 | B |

TABLE 3-continued

| Example | Aldehyde | Product | [M + H⁺] | R$_f$/[min] | Method |
|---|---|---|---|---|---|
| 300 | 4-isopropylbenzaldehyde | | 411.1 | 1.34 | B |
| 301 | thiophene-2-carbaldehyde | | 375.1 | 1.09 | B |
| 302 | 4-methoxybenzaldehyde | | 399.1 | 1.13 | B |
| 303 | isonicotinaldehyde | | 370.1 | 0.87 | B |
| 304 | 3-methoxybenzaldehyde | | 399.1 | 1.14 | B |
| 305 | piperidine-4-carbaldehyde | | 376.2 | 0.75 | B |
| 306 | 4-(dimethylamino)benzaldehyde | | 412.2 | 1.00 | B |
| 307 | 4-chlorobenzaldehyde | | 403.1 | 1.21 | B |

7-Fluoro-6-(1-isopropyl-piperidin-4-yloxy)-4-methyl-2H-isoquinolin-1-one (308)

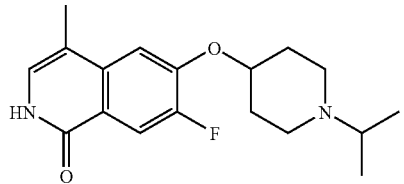

By alkylation of 50 mg of 7-fluoro-4-methyl-6-(piperidin-4-yloxy)-2H-isoquinolin-1-one (22) with isopropylbromide in the presence of triethylamine in DMF at 60° C. 31 mg of 7-Fluoro-6-(1-isopropyl-piperidin-4-yloxy)-4-methyl-2H-isoquinolin-1-one were obtained.

$R_t$=0.93 min (Method B). Detected mass: 319.2 (M+H$^+$).

5-Chloro-6-(piperidin-4-yloxy)-2H-isoquinolin-1-one (309)

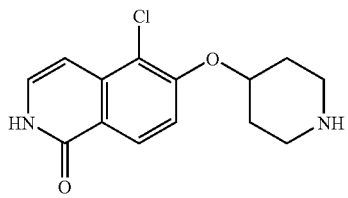

60 mg (0.21 mmol) 6-(piperidin-4-yloxy)-2H-isoquinolin-1-one-hydrochloride (12) were dissolved in 5 mL of concentrated sulphuric acid. At 0° C. 28.6 mg (0.21 mmol) of N-chloro succinimide were added and the mixture was stirred at 50° C. After 2 h the solution was poured on ice and the pH was brought to about 12 by adding solid NaOH. The aqueous solution was extracted twice with dichloromethane. The organic layers were dried with MgSO4 and evaporated. The crude product was purified by preparative HPLC. The obtained trifluoroacetate was dissolved in 2 N HCl and the solvent was removed i. vac. Dissolving the residue in water, followed by lyophilization gave the desired product as HCl-salt. $R_t$=0.86 min (Method A). Detected mass: 279.1/281.1 (M+H$^+$).

7-Bromo-6-fluoro-isoquinoline 2-oxide (310)

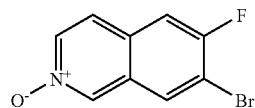

Starting from 7-bromo-6-fluoro-isoquinoline (15), the title compound was prepared following the method described for 7-chloro-6-fluoro-isoquinoline 2-oxide (5). $R_t$=0.93 min (Method C). Detected mass: 242.2/244.2 (M+H$^+$).

7-Bromo-1-chloro-6-fluoro-isoquinoline (311)

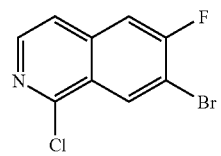

Starting from 7-bromo-6-fluoro-isoquinoline 2-oxide (310) the desired product was synthesized according to the protocol described for 1,7-di-chloro-6-fluoro-isoquinoline (6). $R_t$=1.70 min (Method C). Detected mass: 260.0/262.0 (M+H$^+$).

7-Bromo-6-fluoro-2H-isoquinolin-1-one (312)

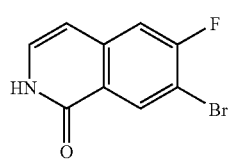

12.9 g (49.5 mmol) 7-bromo-1-chloro-6-fluoro-isoquinoline (311) were dissolved in 250 mL of acetic acid. After adding 38.7 g (0.5 mol) ammonium acetate, the solution was stirred at 100° C. After 3 h, the solvent was removed i. vac. and the residue was poured on water. The precipitate was filtered and dried to yield 9.91 g (83%) of the title compound. $R_t$=1.15 min (Method C). Detected mass: 242.2/244.1 (M+H$^+$).

7-Bromo-6-fluoro-2-(4-methoxy-benzyl)-2H-isoquinolin-1-one (313)

9.66 g (39.9 mmol) of 7-bromo-6-fluoro-2H-isoquinolin-1-one (312) were dissolved in 180 mL of dimethyl acetamide and 1.92 g (48.0 mmol) of sodium hydride (60%) were added. After 1 h at room temperature a solution of 7.50 g (48.0 mmol) of 4-methoxy benzylchloride in 25 mL of dimethyl acetamide was added. The mixture was stirred at room temperature until complete conversion is achieved. For the isolation procedure, the solvent is removed i. vac., the residue was taken up in saturated sodium bicarbonate solution and extracted three times with dichloromethane. The organic layers are dried with MgSO4 and evaporated to yield 16.8 g of a dark oil as crude product, which was stirred in methanol. Filtration of the precipitate gave 6.56 g of the title compound as a yellow solid. The mother liquor was evaporated and the residue purified by preparative HPLC, which gave additional 2.62 g of the desired product. $R_t$=1.71 min (Method C). Detected mass: 362.3/364.3 (M+H⁺).

4-[7-Bromo-2-(4-methoxy-benzyl)-1-oxo-1,2-dihydro-isoquinolin-6-yloxy]-piperidine-1-carboxylic acid tert-butyl ester (314)

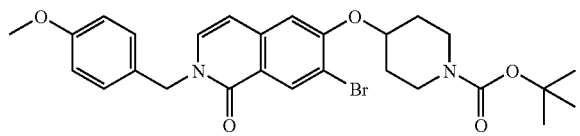

126 mg (0.625 mmol) of 4-hydroxy-piperidine-1-carboxylic acid tert-butyl ester were dissolved in 2.5 mL of dimethylacteamide and 30 mg (0.75 mmol) of NaH (60% purity) were added at room temperature. After 15 minutes 181 mg (0.5 mmol) of 7-bromo-6-fluoro-2-(4-methoxy-benzyl)-2H-isoquinolin-1-one (313) were added and stirring was continued at room temperature. After 5.5 h the solvent was removed i. vac. After adding saturated sodium bicarbonatesodium bicarbonate solution, the mixture was extracted twice with dichloromethane. The organic layers were dried with MgSO4 and evaporated. After final purification by preparative HPLC, 182 mg of the product could be isolated. $R_t$=1.93 min (Method C). Detected mass: 543.5/545.5 (M+H⁺).

7-Bromo-6-(piperidin-4-yloxy)-2H-isoquinolin-1-one (17)

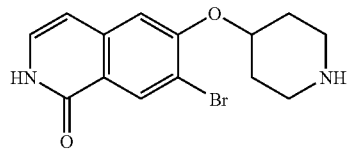

182 mg 4-[7-bromo-2-(4-methoxy-benzyl)-1-oxo-1,2-dihydro-isoquinolin-6-yloxy]-piperidine-1-carboxylic acid tert-butyl ester (314) were dissolved in 5 mL of trifluoroacetic acid. After 2 h at room temperature, the mixture was heated at 140° C. in a microwave for 2 h. The solvent was removed i. vac. and the residue was dissolved 2 N HCl. The aqueous solution was washed twice with dichloromethane and the organic layers were extracted with 2 N HCl. The combined aqueous solutions were evaporated i. vac. and the residue was dissolved in water. After lyophilization the title compound was isolated as HCl-salt. $R_t$=0.80 min (Method B). Detected mass: 323.1/325.1 (M+H⁺).

6-Fluoro-2-(4-methoxy-benzyl)-7-phenyl-2H-isoquinolin-1-one (315)

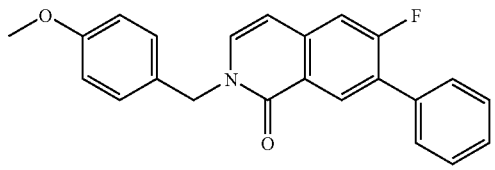

453 mg (1.25 mmol) 7-bromo-6-fluoro-2-(4-methoxy-benzyl)-2H-isoquinolin-1-one (313), 432 mg (3.125 mmol) K2CO3 and 190.5 mg (1.56 mmol) phenylboronic acid were dissolved in 12.5 mL toluene. Under Argon, 72 mg (0.062 mmol) Pd(Ph3)4 were added and the solution was stirred at 100° C. After complete conversion, the solvent is removed i. vac. and saturated sodium bicarbonate solution is added. The aqueous solution is extracted three times with dichloromethane and the organic layers are dried with MgSO4. After evaporation, the crude product is purified by preparative HPLC. $R_t$=1.80 min (Method C). Detected mass: 360.4 (M+H⁺).

4-[2-(4-Methoxy-benzyl)-1-oxo-7-phenyl-1,2-dihydro-isoquinolin-6-yloxy]-piperidine-1-carboxylic acid tert-butyl ester (316)

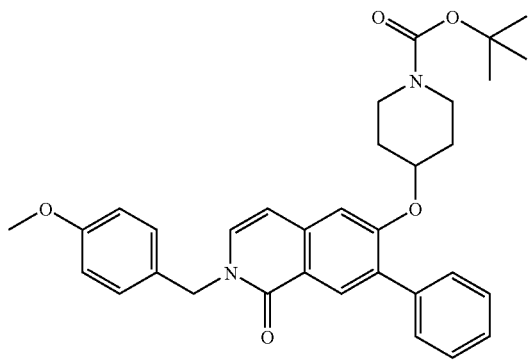

168 mg (0.83 mmol) 4-hydroxy-piperidine-1-carboxylic acid tert-butyl ester were dissolved in 5 mL of dimethylacetamide and 20 mg (0.83 mmol) of sodium hydride (60%) were added. The mixture was stirred at room temperature. After 30 minutes a solution of 240 mg (0.67 mmol) 6-fluoro-2-(4-methoxy-benzyl)-7-phenyl-2H-iso-quinolin-1-one (315) in 5 mL of dimethylacetamide was added and stirring was continued at room temperature. After standing overnight, 20 mg (0.83 mmol) of sodium hydride (60%) were added and the solution was stirred at 100° C. After 1 h, the solvent was removed i. vac. and saturated sodium bicarbonate solution was added. The aqueous phase was extracted three times with dichloromethane. The organic layers were dried with MgSO4 and evaporated. The crude product was purified by preparative HPLC. $R_t$=1.98 min (Method C). Detected mass: 541.7 (M+H⁺).

7-Phenyl-6-(piperidin-4-yloxy)-2H-isoquinolin-1-one (317)

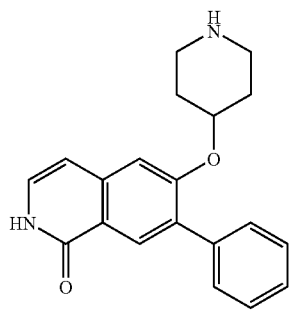

4-[2-(4-Methoxy-benzyl)-1-oxo-7-phenyl-1,2-dihydro-isoquinolin-6-yloxy]-piperidine-1-carboxylic acid tert-butyl ester (316) was deprotected following the method described for 7-bromo-6-(piperidin-4-yloxy)-2H-isoquinolin-1-one (17). Similar work up delivers the title compound as HCl-salt. $R_t$=1.05 min (Method B). Detected mass: 321.1 (M+H$^+$).

7-Ethyl-6-fluoro-2-(4-methoxy-benzyl)-2H-iso-quinolin-1-one (318)

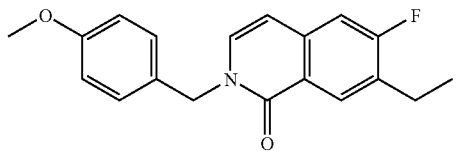

The title compound was synthesized following the method described for 6-fluoro-2-(4-methoxy-benzyl)-7-phenyl-2H-isoquinolin-1-one (315) starting from 7-bromo-6-fluoro-2-(4-methoxy-benzyl)-2H-isoquinolin-1-one (313) and ethyl-boronic acid. $R_t$=1.69 min (Method C). Detected mass: 312.4 (M+H$^+$).

4-[7-Ethyl-2-(4-methoxy-benzyl)-1-oxo-1,2-dihydro-isoquinolin-6-yloxy]-piperidine-1-carboxylic acid tert-butyl ester (319)

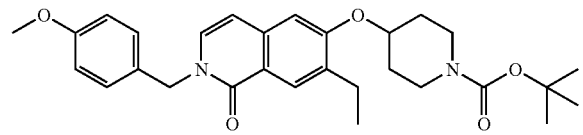

The title compound was synthesized following the method described for 4-[2-(4-methoxy-benzyl)-1-oxo-7-phenyl-1,2-dihydro-isoquinolin-6-yloxy]-piperidine-1-carboxylic acid tert-butyl ester (316), starting from 7-ethyl-6-fluoro-2-(4-methoxy-benzyl)-2H-isoquinolin-1-one (318) and 4-hydroxy-piperidine-1-carboxylic acid tert-butyl ester. $R_t$=1.91 min (Method C). Detected mass: 493.6 (M+H$^+$).

7-Ethyl-6-(piperidin-4-yloxy)-2H-isoquinolin-1-one (320)

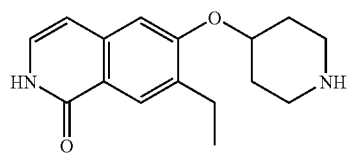

4-[7-Ethyl-2-(4-methoxy-benzyl)-1-oxo-1,2-dihydro-isoquinolin-6-yloxy]-piperidine-1-carboxylic acid tert-butyl ester (319) is deprotected following the method described for 7-bromo-6-(piperidin-4-yloxy)-2H-isoquinolin-1-one (17). Final purification by preparative HPLC delivers the title compound as trifluoroacetate. $R_t$=0.92 min (Method A). Detected mass: 273.2 (M+H$^+$).

| Method A: | |
|---|---|
| Stationary phase: | Col YMC Jsphere 33 × 2 |
| Gradient: | ACN + 0.05% TFA:H$_2$O + 0.05% TFA |
| | 5:95(0 min) to 95:5(3.4 min) to 95:5(4.4 min) |
| Flow | 1 mL/min |

| Method B: | |
|---|---|
| Stationary phase: | Col YMC Jsphere 33 × 2 |
| Gradient: | ACN + 0.05% TFA:H$_2$O + 0.05% TFA |
| | 5:95(0 min) to 95:5(2.5 min) to 95:5(3.0 min) |
| Flow | 1 mL/min |

| Method C: | |
|---|---|
| Stationary phase: | Col YMC Jsphere ODS H80 20 × 2 |
| Gradient: | ACN:H$_2$O + 0.05% TFA |
| | 4:96(0 min) to 95:5(2.0 min) to 95:5(2.4 min) |
| Flow | 1 mL/min |

| Method D: | |
|---|---|
| Stationary phase: | Col YMC Jsphere 33 × 2.1 |
| Gradient: | Grad ACN + 0.08% FA:H$_2$O + 0.1% FA (Formic acid) |
| | 5:95 (0 min) to 95:5 (2.5 min) to 95:5 (3 min) |
| Flow | 1.3 mL/min |

Determination of Rho Kinase Inhibition

To measure Rho-kinase inhibition, IC$_{50}$ values were determined according to the following protocol:

Buffer: 25 mM Tris pH7.5; 0.02% BSA; 5% Glycerol; 0.008% Triton X100; 2% DMSO, 1 mM DTT; 1 mM MgCl$_2$; 0.5 µCi/well γ$^{33}$P ATP Enzyme: ROCKII or ROKα) (Upstate, Catalog #14-451 Lot #24880U) 0.1 ng/µl Final concentration of ATP in reaction mixture 40 µM Biotinylated substrate, diluted to 0.25 µM with buffer described above (without ATP)

1. 10 µl Tris buffer (±Inhibitor)
2. Add 30 µL of enzyme solution
3. Start the reaction with 30 µL of mix substrate/ATP/ATP33
4. Incubate for 20 min at room temperature
5. Stop reaction with 30 µL of 50 mM EDTA
6. Transfer 50 µL of stopped solution to Streptavidin Flash Plate plus, Perkin Elmer, SMP 103A
7. Incubate for 30 min at RT
8. Wash 4 times with 300 µl of PBS/0.1% Tween 20
9. Radioactivity in the well was determined The following products/compounds were tested in said assay by using the respective form (salt or free base) obtained as in the examples described above and the following activities were measured.

| No. | pIC$_{50}$ |
|---|---|
| 12 | +++++ |
| 17 | +++++ |
| 21 | +++++ |
| 23 | +++++ |
| 25 | ++++ |
| 28 | +++++ |
| 31 | +++++ |
| 32 | ++++ |
| 40 | +++++ |
| 45 | +++++ |
| 49 | ++++ |
| 52 | +++++ |
| 54 | +++++ |

-continued

| No. | pIC$_{50}$ |
|---|---|
| 55 | +++++ |
| 58 | +++++ |
| 101 | +++++ |
| 265 | +++++ |
| 266 | +++++ |
| 275 | +++++ |
| 276 | +++++ |
| 309 | +++++ |

The given activity is denoted as the negative decadal logarithm of the IC$_{50}$ (pIC$_{50}$) as follows:

| | |
|---|---|
| +: | pIC50 ≦ 3.0 |
| ++: | 3.0 ≦ pIC$_{50}$ < 4.0 |
| +++: | 4.0 ≦ pIC$_{50}$ < 5.0 |
| ++++: | 5.0 ≦ pIC$_{50}$ < 6.0 |
| +++++: | 6.0 ≦ pIC$_{50}$ |

The invention claimed is:

1. A compound of the formula (I)

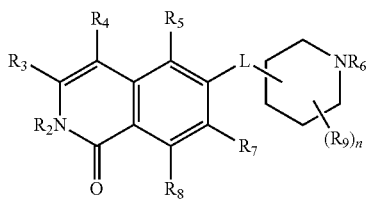

or of the formula (I')

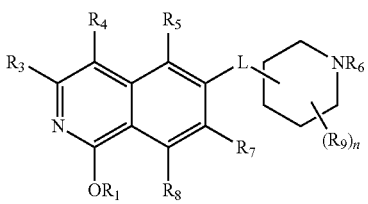

wherein

R1 is H, (C1-C6)alkyl, (C2-C6)alkenyl, (C2-C6)alkynyl, [(C1-C6)alkylene]0-1-(C3-C8)cycloalkyl, [(C1-C6)alkylene]0-1-(C5-C10)heterocyclyl, [(C1-C6)alkylene]0-1-(C6-C10)aryl, C(O)—(C1-C6)alkyl, C(O)(C2-C6)alkenyl, C(O)—(C2-C6)alkynyl, C(O)—[(C1-C6)alkylene]0-1-(C3-C8)cycloalkyl, C(O)—[(C1-C6)alkylene]0-1-(C5-C10)heterocyclyl, or C(O)—[(C1-C6)alkylene]0-1-(C6-C10)aryl;

R2 is H, (C1-C6)alkyl, [(C1-C6)alkylene]0-1-R', [(1-C6)alkylene]0-1-O—(C1-C6)alkyl, [(C1-C6)alkylene]0-1-O—R', [(C1-C6)alkylene]0-1-NH2, [(C1-C6)alkylene]0-1-NH(C1-C6)alkyl, [(C1-C6)alkylene]0-1-N[(C1-C6)alkyl]2, [(C1-C6)alkylene]0-1-CH[R']2, [(C1-C6)alkylene]0-1-C(O)—R', [(C1-C6)alkylene]0-1-C(O)NH2, [(C1-C6)alkylene]0-1-C(O)NH—R', or [(C1-C6)alkylene]0-1-C(O)N[R']2 ;

R3 is H, halogen, CN, (C1-C6)alkyl, (C1-C6)alkylene-R', OH, O—R", NH2, NHR", NR"R" or NH—C(O)—R";

R4 is H, halogen, OH, CN, (C1-C6)alkyl, (C3-C8)cycloalkyl, (C1-C6)alkylene-R' or NH—(C6-C10)aryl;

R5 is H, halogen, CN, NO2, (C1-C6)alkyl, (C2-C6)alkenyl, R', (C1-C6)alkylene-R', (C1-C6)alkylene-(C6-C10)aryl, (C2-C6)alkenylene-(C6-C10)aryl, (C1-C6)alkylene-(C5-C10)heterocyclyl, NH2, NH—R', NH—SO2H, NH—SO2-(C1-C6)alkyl, NH—SO2-R', NH—C(O)—(C1-C6)alkyl, NH—C(O)—R', C(O)N[(C1-C6)alkyl]2, C(O)OH or C(O)O—(C1-C6)alkyl;

R6 is H, R', (C1-C8)alkyl, (C1-C6)alkylene-R', (C1-C6)alkylene-O—(C1-C6)alkyl, (C1-C6)alkylene-O—R', (C1-C6)alkylene-CH[R']2, (C1-C6)alkylene-C(O)—R', (C1-C6)alkylene-C(O)NH2, (C1-C6)alkylene-C(O)NH—R', or (C1-C6)alkylene-C(O)N[R']2;

R7 and R8 are independently of each other H, halogen, CN, NO2, (C1-C6)alkyl, O—(C1-C6)alkyl, O—[(C1-C6)alkylene]0-1-R', (C2-C6)alkenyl, R', (C2-C6)alkenylene-(C6-C10)aryl, (C1-C6)alkylene-R', NH2, NH—R', NH—SO2H, NH—SO2-(C1-C6)alkyl, NH—SO2-R', SO2-NH2, SO2-NHR', NH—C(O)—(C1-C6)alkyl, NH—C(O)—R', C(O)N[(C1-C6)alkyl]2, C(O)OH or C(O)O—(C1-C6)alkyl;

R9 is halogen or (C1-C6)alkyl;

R' is (C3-C8)cycloalkyl, (C5-C10)heterocyclyl or (C6-C10)aryl;

R" is (C3-C8)cycloalkyl, (C5-C10)heterocyclyl, (C6-C10)aryl, (C1-C6)alkyl, (C1-C6)alkylene-R', (C1-C6)alkylene-O—(C1-C6)alkyl, (C1-C6)alkylene-O—R', or (C1-C6)alkylene-NRxRy;

Rx and Ry are independently of each other (C1-C6)alkyl, (C5-C10)heterocyclyl, (C6-C10)aryl, (C1-C4)alkylene-(C5-C10)heterocyclyl, (C1-C4)alkylene-(C6-C10)aryl, (C1-C4)alkylene-NH(C1-C6)alkyl, (C1-C4)alkylene-N[(C1-C6)alkyl]2, (C1-C4)alkylene-N [(C6-C10)aryl]2, or (C1-C4)alkylene-N[(C5-C10)heterocyclyl]2;

n is 0, 1, 2, 3 or 4; and

L is O or O—(C1-C6)alkylene;

wherein in residues R4, R5, R7 and R8 one alkyl or alkylene hydrogen atom can optionally be substituted by OH, OCH3, COOH, COOCH3, NH2, NHCH3, N(CH3)2, CONH2, CONHCH3 or CON(CH3)2, or an alkyl or alkylene may be halogenated once or more;

or a pharmaceutically acceptable salt thereof, stereoisomeric form thereof or physiologically functional derivative thereof, pharmaceutically acceptable salt of a stereoisomeric form thereof or physiologically functional derivative thereof, or stereoisomeric form of a physiologically functional derivative thereof.

2. The compound according to claim 1 wherein

R4 is H, halogen, OH, CN, (C1-C6)alkyl, (C3-C8)cycloalkyl, or (C1-C6)alkylene-R';

R5 is H, halogen, CN, NO2, (C1-C6)alkyl, (C2-C6)alkenyl, R', (C1-C6)alkylene-(C6-C10)aryl, (C2-C6)alkenylene-(C6-C10)aryl, (C1-C6)alkylene-(C5-C10)heterocyclyl, NH2, NH—R', NH—SO2H, NH—SO2-(C1-C6)alkyl, NH—SO2-R', NH—C(O)—(C1-C6)alkyl, NH—C(O)—R', C(O)N[(C1-C6)alkyl]2, C(O)OH or C(O)O—(C1-C6)alkyl;

or a pharmaceutically acceptable salt thereof, stereoisomeric form thereof or physiologically functional derivative thereof, pharmaceutically acceptable salt of a stereoisomeric form thereof or physiologically functional derivative thereof, or stereoisomeric form of a physiologically functional derivative thereof.

3. The compound according to claim 1 wherein
R4 is H, halogen, OH, CN, (C1-C6)alkyl, (C3-C8)cycloalkyl, or (Cl-C6)alkylene-R';
R5 is H, halogen, CN, NO2, (C1-C6)alkyl, (C2-C6)alkenyl, R',
(C1-C6)alkylene-(C6-C10)aryl, (C2-C6)alkenylene-(C6-C10)aryl,
(C1-C6)alkylene-(C5-C10)heterocyclyl, NH2, NH—R', NH—SO2H, NH—SO2-(C1-C6)alkyl,
NH—SO2-R', NH—C(O)—(C1-C6)alkyl, NH—C(O)—R', C(O)N[(C1-C6)alkyl]2, C(O)OH or
C(O)O—(C1-C6)alkyl;
wherein in
residues R4, R5, R7 and R8 one alkyl or alkylene hydrogen atom can optionally be substituted by OH, F, OCH3, COOH, COOCH3, NH2, NHCH3, N(CH3)2, CONH2, CONHCH3 or CON(CH3)2,
or a pharmaceutically acceptable salt thereof, stereoisomeric form thereof or physiologically functional derivative thereof, pharmaceutically acceptable salt of a stereoisomeric form thereof or physiologically functional derivative thereof, or stereoisomeric form of a physiologically functional derivative thereof.

4. The compound according to claim 1 of the formula (I).
5. The compound according to claim 1 of the formula (I') wherein R1 is hydrogen.
6. The compound according to claim 1, wherein R6 is H, (C1-C6)alkyl, R',
(C1-C4)alkylene-(C3-C8)cycloalkyl, (C1-C4)alkylene-(C5-C10)heterocyclyl,
(C1-C4)alkylene-C(O)—(C5-C10)heterocyclyl, (C1-C4)alkylene-C(O)—(C6-C10)aryl or
(C1-C6)alkylene-(C6-C10)aryl.
7. The compound according to claim 1, wherein R6 is H, (C1-C6)alkyl, (C5-C10)heterocyclyl, (C3-C8)cycloalkyl, (C1-C4)alkylene-(C3-C8)cycloalkyl,
(C1-C4)alkylene-(C5-C10)heterocyclyl or (C1-C6)alkylene-(C6-C10)aryl.
8. The compound according to claim 1, wherein R6 is H, (C1-C6)alkyl,
(C3-C8)cycloalkyl,
(C1-C4)alkylene-(C3-C8)cycloalkyl,
(C1-C4)alkylene-(C5-C10)heterocyclyl in which heterocyclyl is unsubstituted or substituted by (C1-C4)alkyl, or
(C1-C4)alkylene-(C6-C10)aryl in which aryl is unsubstituted or substituted by halogen, (C1-C4)alkyl, O—(C1-C4)alkyl, SO2-(C1-C4)alkyl, or N[(C1-C4)alkyl]2.
9. The compound according to claim 1, wherein R6 is H, (C1-C6)alkyl, (C3-C6)cycloalkyl or (C1-C4)alkylene-(C3-C6)cycloalkyl.
10. The compound according to claim 1, wherein R6 is H or (C1-C6)alkyl.
11. The compound according to claim 1, wherein R6 is H.
12. The compound according to claim 1, wherein R5 is H, halogen, CN, (C1-C6)alkyl, R', NH—(C6-C10)aryl, (C1-C6)alkylene-(C6-C10)aryl, or (C1-C6)alkylene-(C5-C10)heterocyclyl.
13. The compound according to claim 1, wherein R5 is H, halogen, (C1-C6)alkyl, R', NH—(C6-C10)aryl or (C1-C6)alkylene-(C6-C10)aryl, or (C1-C6)alkylene-(C5-C10)heterocyclyl.

14. The compound according to claim 1, wherein R5 is H, halogen, (C1-C6)alkyl, (C6-C10)aryl, (C5-C10)heteroaryl, NH—(C6-C10)aryl or (C1-C2)alkylene-(C6-C10)aryl.
15. The compound according to claim 1, wherein R5 is H, halogen, (C1-C6)alkyl, phenyl or (C5-C6)heteroaryl.
16. The compound according to claim 1, wherein R5 is H, halogen or (C1-C6)alkyl.
17. The compound according to claim 1, wherein R5 is H or halogen.
18. The compound according to claim 1, wherein R5 is H.
19. The compound according to claim 1, wherein R4 is H, halogen, CN, (C1-C6)alkyl, or (C1-C6)alkylene-R'.
20. The compound according to claim 1, wherein R4 is H, halogen, (C1-C6)alkyl, or (C1-C6)alkylene-R'.
21. The compound according to claim 1, wherein R4 is H, halogen, (C1-C6)alkyl, or (C1-C2)alkylene-(C6-C10)aryl.
22. The compound according to claim 1, wherein R4 is H, halogen, or (C1-C6)alkyl.
23. The compound according to claim 1, wherein R4 is H.
24. The compound according to claim 1, wherein R7 and R8 are independently of each other H, halogen, CN, (C1-C6)alkyl, O—(C1-C6)alkyl, (C2-C6)alkenyl, R' or (C1-C6)alkylene-(C3-C8)cycloalkyl.
25. The compound according to claim 1, wherein R7 and R8 are independently of each other H, halogen, CN, (C1-C4)alkyl, O—(C1-C4)alkyl, (C2-C4)alkenyl, phenyl, (C5-C6)heteroaryl, (C3-C6)cycloalkyl or (C1-C4)alkylene-(C3-C6)cycloalkyl.
26. The compound according to claim 1, wherein R7 and R8 are independently of each other H, halogen, (C1-C4)alkyl, O—(C1-C4)alkyl or phenyl.
27. The compound according to claim 1, wherein R7 and R8 are H.
28. The compound according to claim 1, wherein R9 is halogen or (C1-C4)alkyl.
29. The compound according to claim 1, wherein R9 is Cl, F, methyl or ethyl.
30. The compound according to claim 1, wherein R9 is methyl.
31. The compound according to claim 1, wherein n is 0, 1, 2 or 3.
32. The compound according to claim 1, wherein n is 0 or 1.
33. The compound according to claim 1, wherein n is 0.
34. The compound according to claim 1, wherein R3 is H, halogen, (C1-C6)alkyl, (C1-C4)alkylene-R', O—R" or NHR".
35. The compound according to claim 1, wherein R3 is H, (C1-C6)alkyl or NHR".
36. The compound according to claim 1, wherein R3 is H, (C1-C4)alkyl, NH—(C5-C6)heterocyclyl or NH-phenyl.
37. The compound according to claim 1, wherein R3 is H, (C1-C4)alkyl, NH—(C5-C6)heteroaryl containing one or more N atoms or NH-phenyl.
38. The compound according to claim 1, wherein R3 is H.
39. The compound according to claim 1, wherein L is attached to the 4-position of the piperdinyl ring as follows

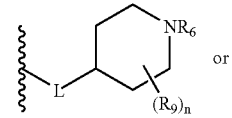

L is attached to the 3-position of the piperdinyl ring as follows

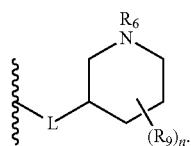

40. The compound according to claim 1, wherein L is attached to the 4-position of the piperdinyl ring.

41. The compound according to claim 1, wherein L is O-methylene, O-ethylene or O.

42. The compound according to claim 1, wherein L is O-methylene, O-ethylene or O attached to the 4-position of the piperdinyl ring.

43. The compound according to claim 1, wherein L is O.

44. The compound according to claim 1, wherein

R3 is H, halogen, CN, (C1-C6)alkyl, (C1-C6)alkylene-R', OH, O—R", NH2, or NHR";

R6 is H, (C3-C8)cycloalkyl, (C1-C8)alkyl, (C1-C6)alkylene-R', (C1-C6)alkylene-O—(C1-C6)alkyl, (C1-C6)alkylene-O—R', (C1-C6)alkylene-CH[R']2, (C1-C6)alkylene-C(O)NH2, (C1-C6)alkylene-C(O)NH—R', or (C1-C6)alkylene-C(O)N[R']2;

R7 and R8 are independently of each other H, halogen, CN, NO2, (C1-C6)alkyl, (C2-C6)alkenyl, R', (C2-C6)alkenylene-(C6-C10)aryl, (C1-C6)alkylene-R', NH2, NH—R', NH—SO2-(C1-C6)alkyl, NH—SO2-R', SO2-NH2, SO2-NHR', NH—C(O)—(C1-C6)alkyl, NH—C(O)—R', C(O)N[(C1-C6)alkyl]2, C(O)OH or C(O)O—(C1-C6)alkyl;

n is 0, 1, 2; and

L is O or O—(C1-C3)alkylene; or or a pharmaceutically acceptable salt thereof, stereoisomeric form thereof or physiologically functional derivative thereof, pharmaceutically acceptable salt of a stereoisomeric form thereof or physiologically functional derivative thereof, or stereoisomeric form of a physiologically functional derivative thereof.

45. The compound according to claim 1, wherein

R3 is H, halogen, CN, (C1-C6)alkyl, (C1-C2)alkylene-R' or NHR";

R4 is H, halogen, CN, (C1-C6)alkyl, (C3-C8)cycloalkyl, (C1-C2)alkylene-R';

R5 is H, halogen, CN, NO2, (C1-C6)alkyl, (C2-C6)alkenyl, R', (C1-C6)alkylene-(C6-C10)aryl, (C2-C6)alkenylene-(C6-C10)aryl, (C1-C6)alkylene-(C5-C10)heterocyclyl, NH2, NH—R', NH—C(O)—(C1-C6)alkyl, or C(O)N[(C1-C6)alkyl]2;

R6 is H, (C3-C8)cycloalkyl, (C1-C8)alkyl, or (C1-C3)alkylene-R';

R7 and R8 are independently of each other H, halogen, CN, NO2, (C1-C6)alkyl, (C2-C6)alkenyl, R', (C2-C3)alkenylene-(C6-C10)aryl, (C1-C3)alkylene-R', NH—R', NH—SO2-(C1-C6)alkyl, or SO2-NH2;

n is 0 or 1; and

L is O or O-methylene;

or a pharmaceutically acceptable salt thereof, stereoisomeric form thereof or physiologically functional derivative thereof, pharmaceutically acceptable salt of a stereoisomeric form thereof or physiologically functional derivative thereof, or stereoisomeric form of a physiologically functional derivative thereof.

46. The compound according to claim 1, wherein

R3 is H, halogen, CN, (C1-C6)alkyl, (C1-C2)alkylene-R' or NHR";

R4 is H, halogen, CN, (C1-C4)alkyl, (C3-C6)cycloalkyl, or (C1-C2)alkylene-R';

R5 is H, halogen, CN, NO2, (C1-C6)alkyl, (C2-C6)alkenyl, R', (C1-C6)alkylene-(C6-C10)aryl, (C2-C6)alkenylene-(C6-C10)aryl, (C1-C6)alkylene-(C5-C10)heterocyclyl, or NH—R';

R6 is H, (C3-C6)cycloalkyl or (C1-C4)alkyl;

R7 and R8 are independently of each other H, halogen, CN, NO2, (C1-C6)alkyl, (C2-C6)alkenyl, R', (C2-C3)alkenylene-(C6-C10)aryl, (C1-C3)alkylene-R', NH—SO2-(C1-C6)alkyl, or SO2-NH2;

R9 is halogen or (C1-C4)alkyl;

n is 0 or 1; and

L is O;

or a pharmaceutically acceptable salt thereof, stereoisomeric form thereof or physiologically functional derivative thereof, pharmaceutically acceptable salt of a stereoisomeric form thereof or physiologically functional derivative thereof, or stereoisomeric form of a physiologically functional derivative thereof.

47. The compound of claim 1 wherein R1, R3, R4, R5, and R9 are H; R7 is H, methyl or halogen; R6 is H, (C1-C4)alkyl, phenyl or (C5-C10)heteroaryl, which phenyl or (C5-C10)heteroaryl are unsubstituted or substituted by one or more (C1-C4)alkyl, O—(C1-C6)alkyl, and halogen.

48. The compound according to claim 1 selected from the group consisting of

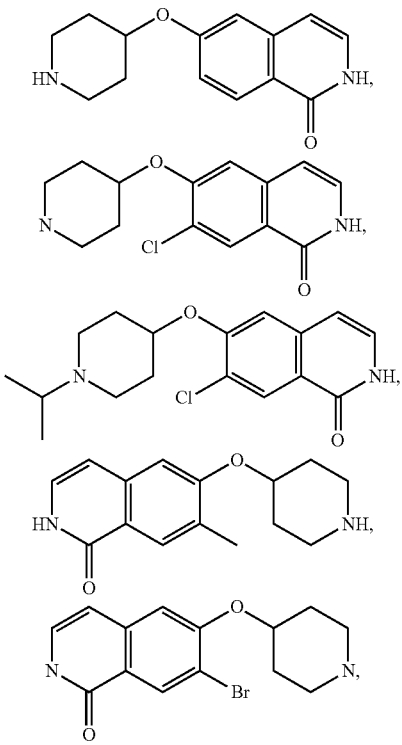

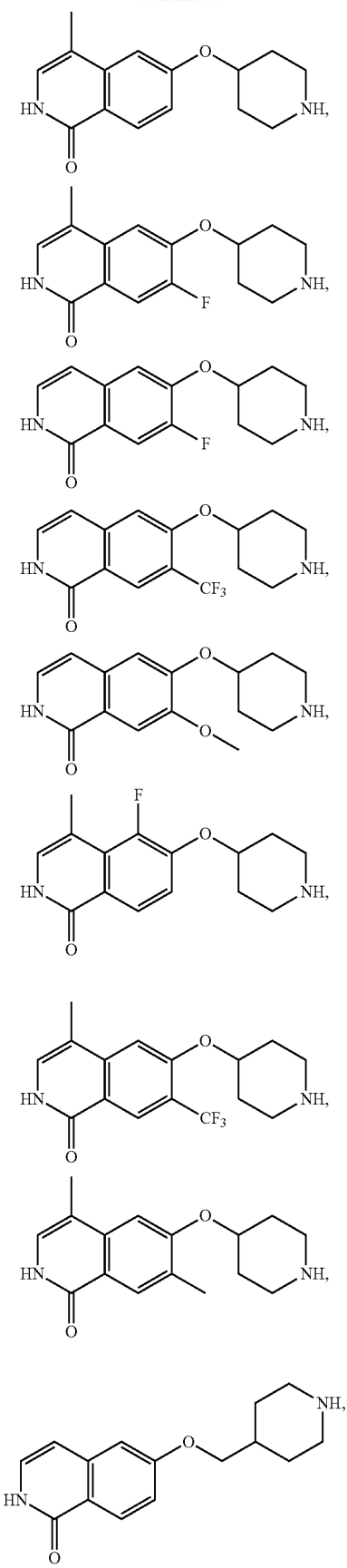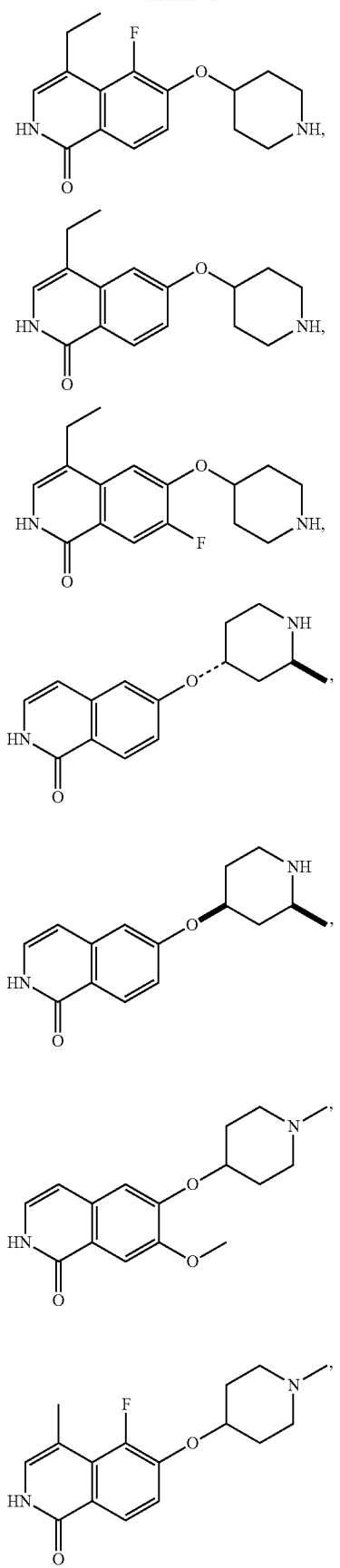

125
-continued
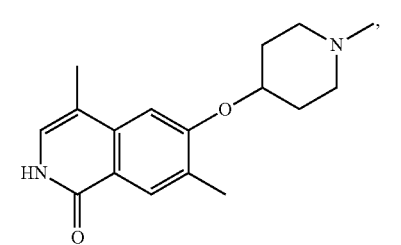
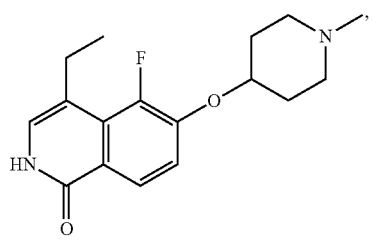
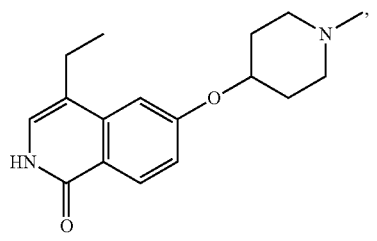
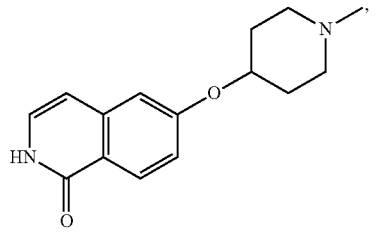
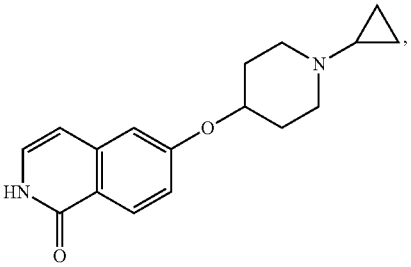
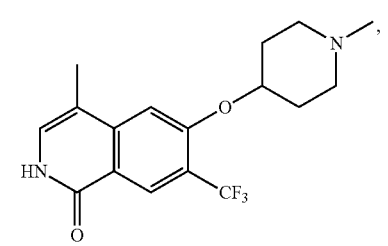
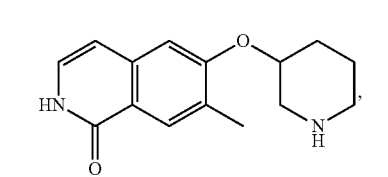
126
-continued
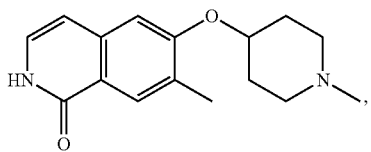
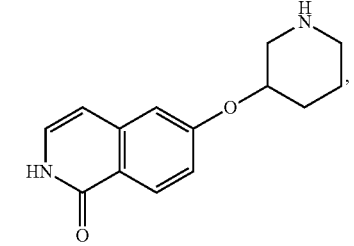
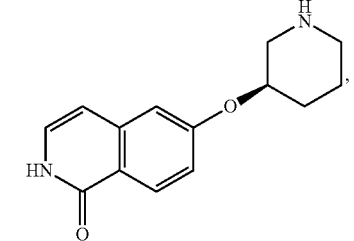
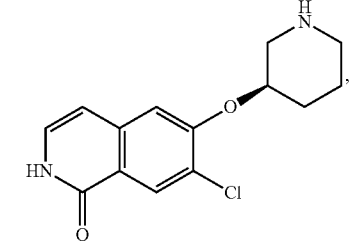
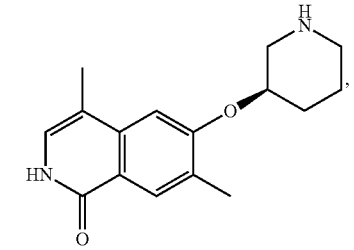
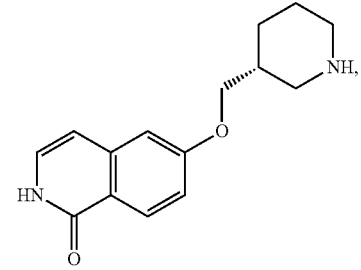
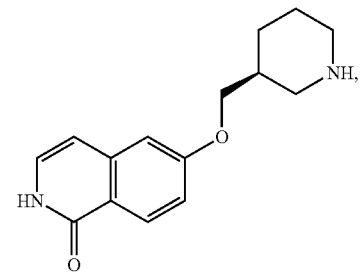

127
-continued
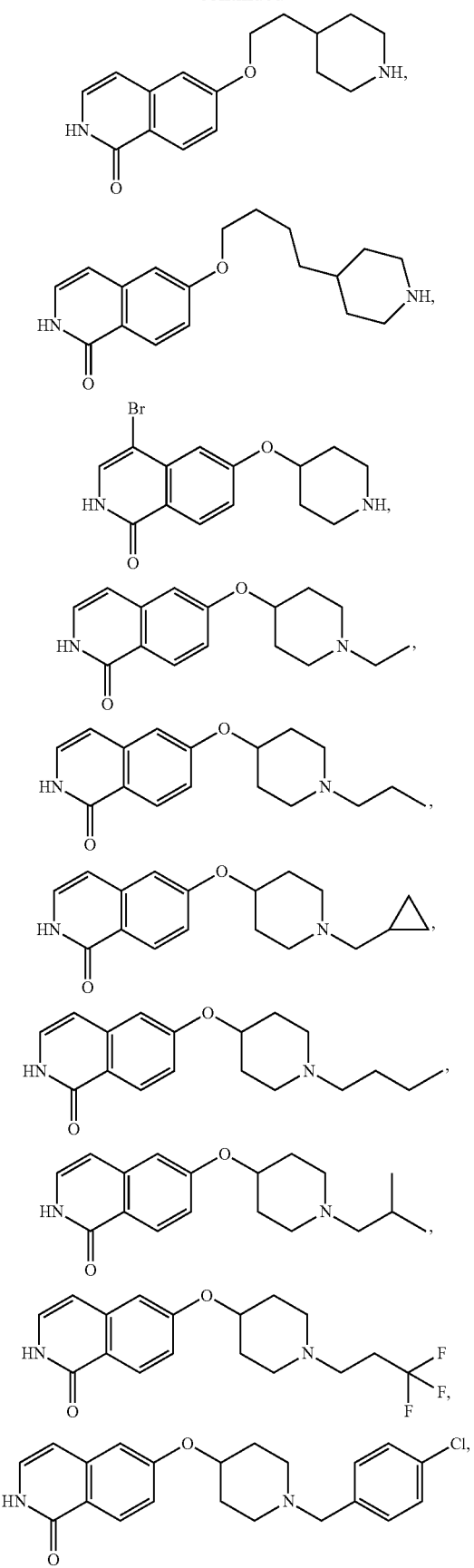
128
-continued
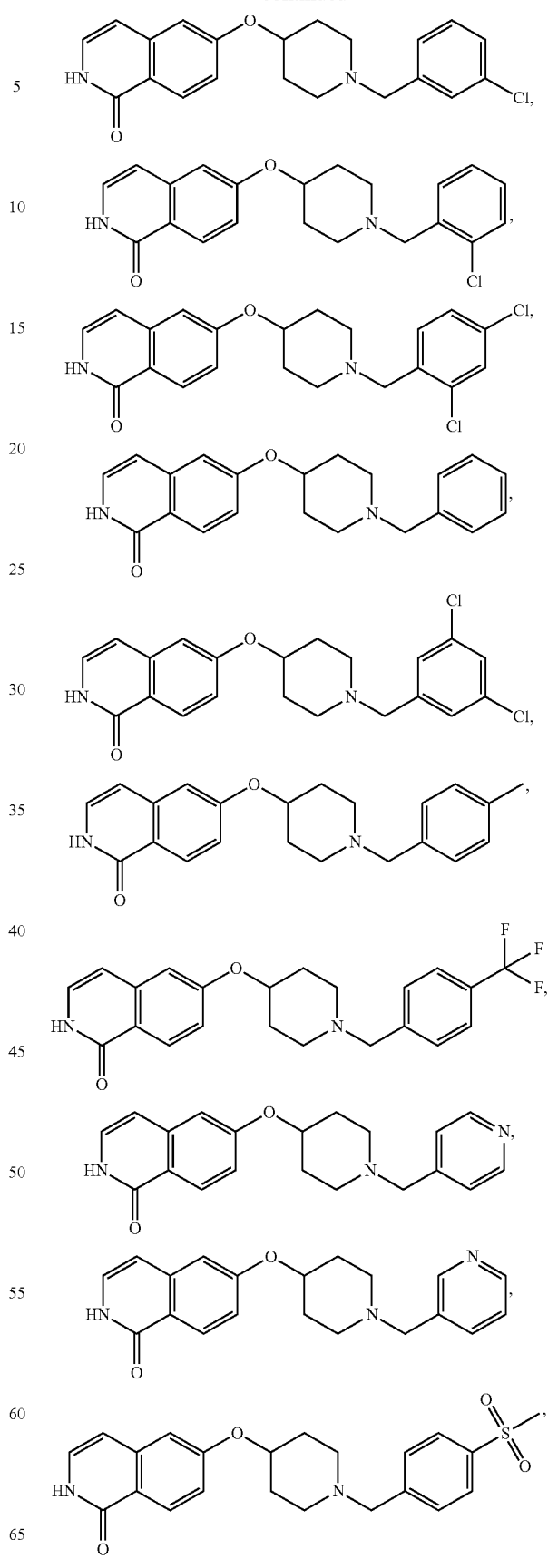

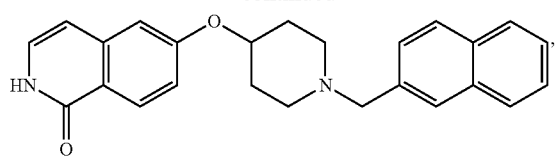
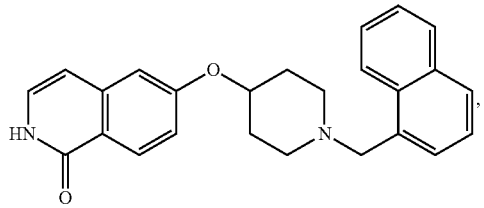
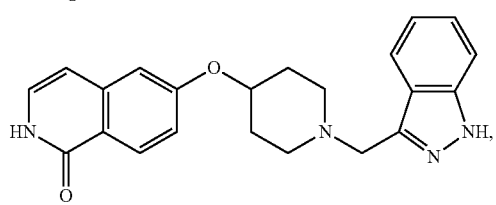
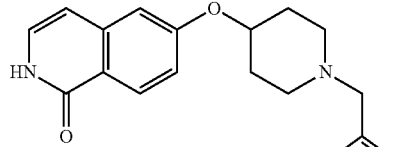
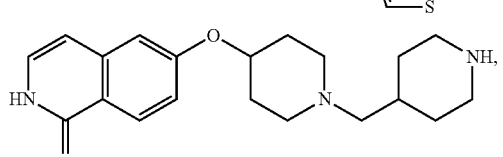
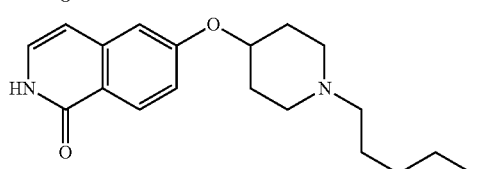
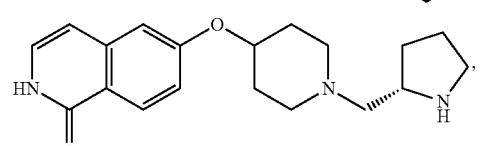
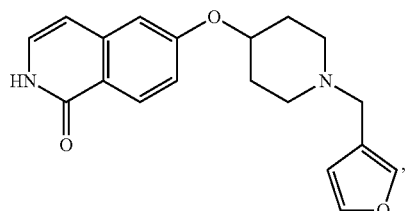
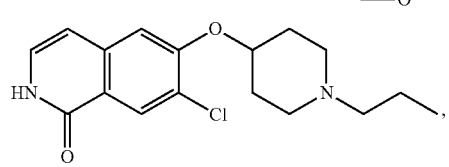
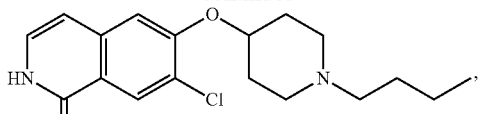
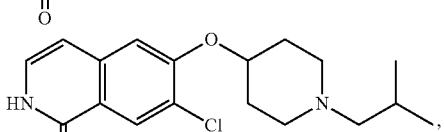
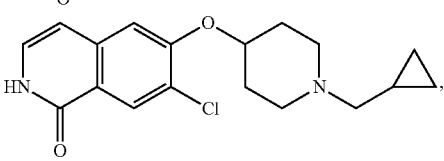
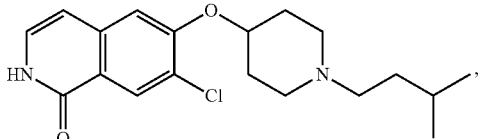
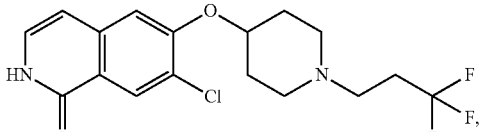
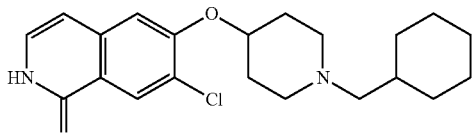
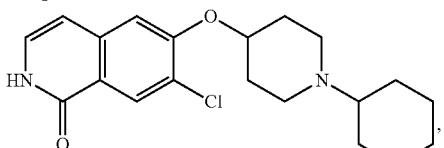
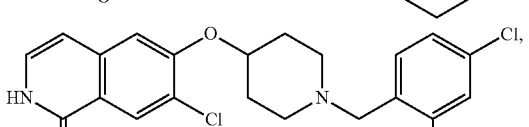
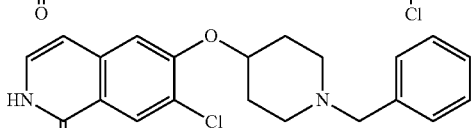
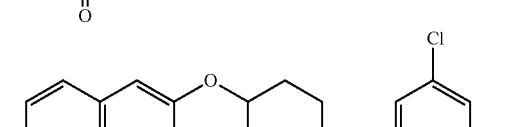
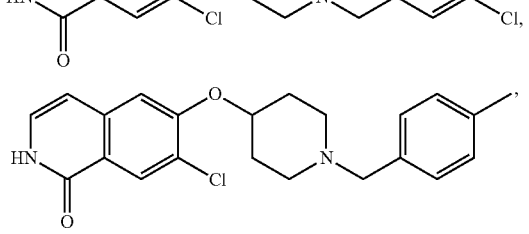

131
-continued
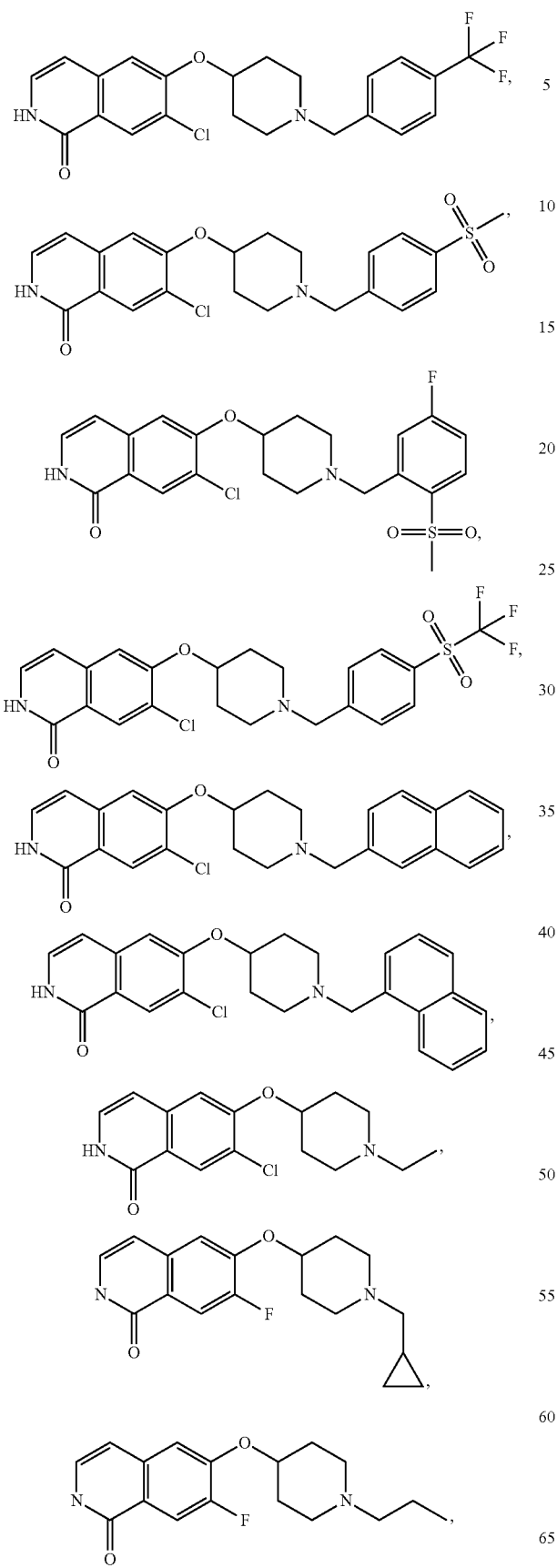
132
-continued
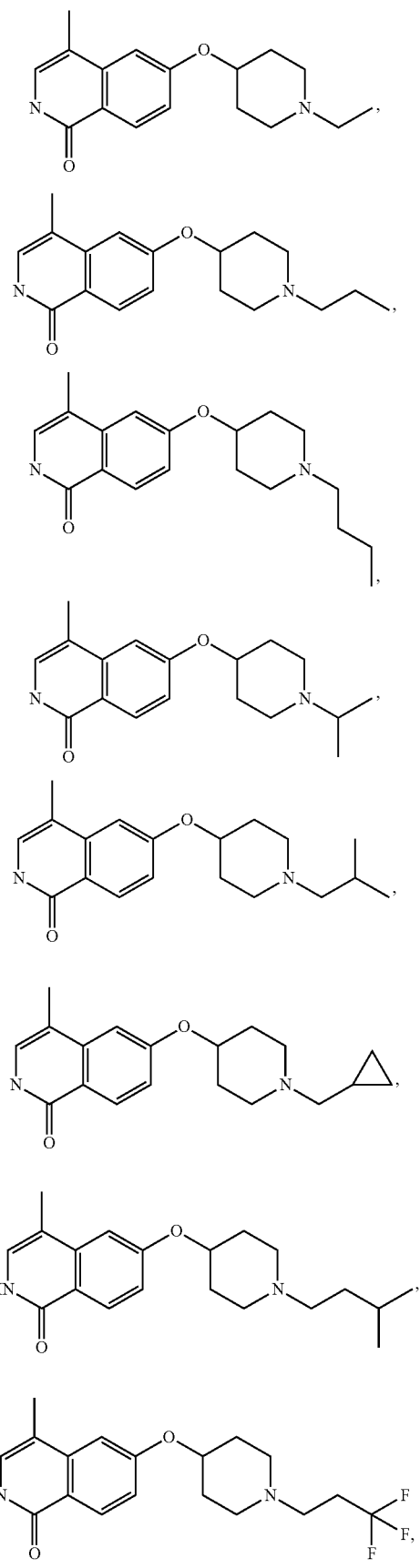

133
-continued
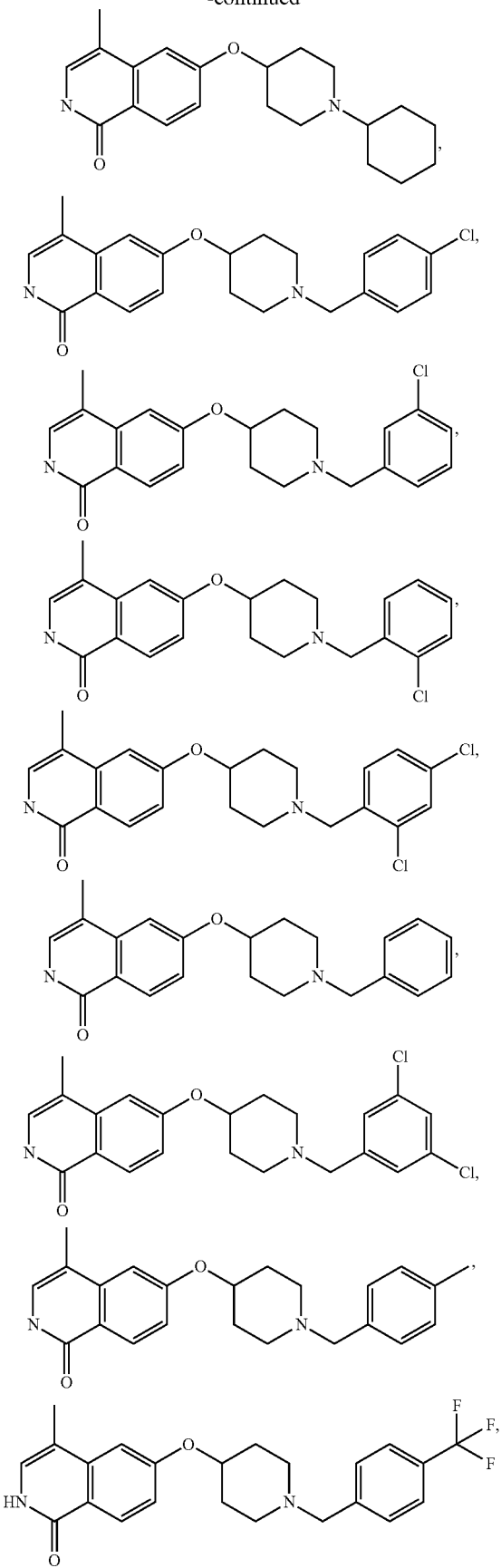
134
-continued
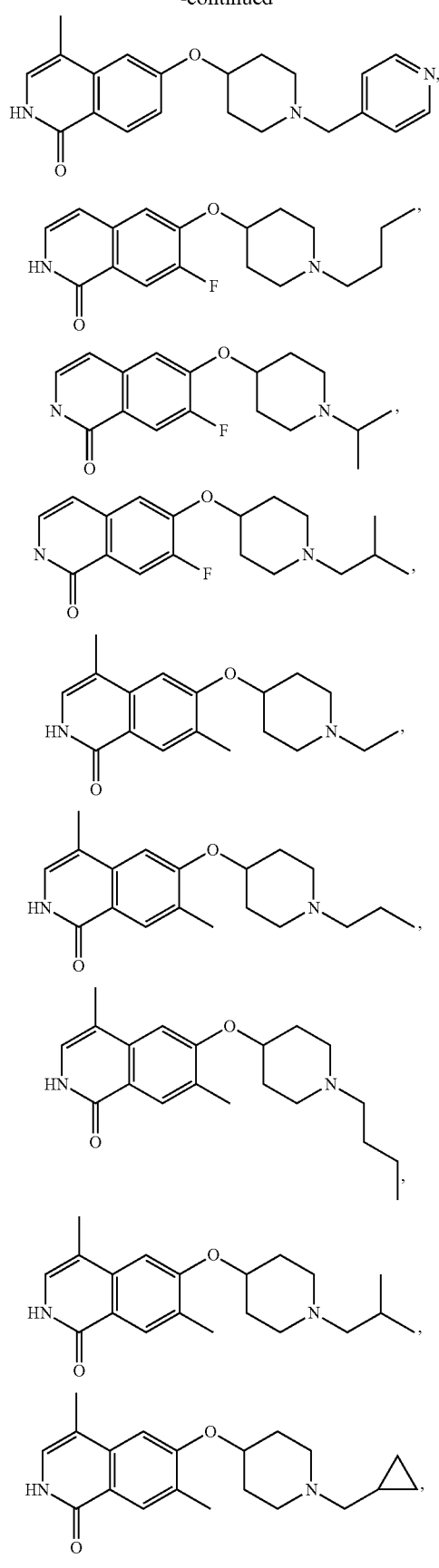

135
-continued
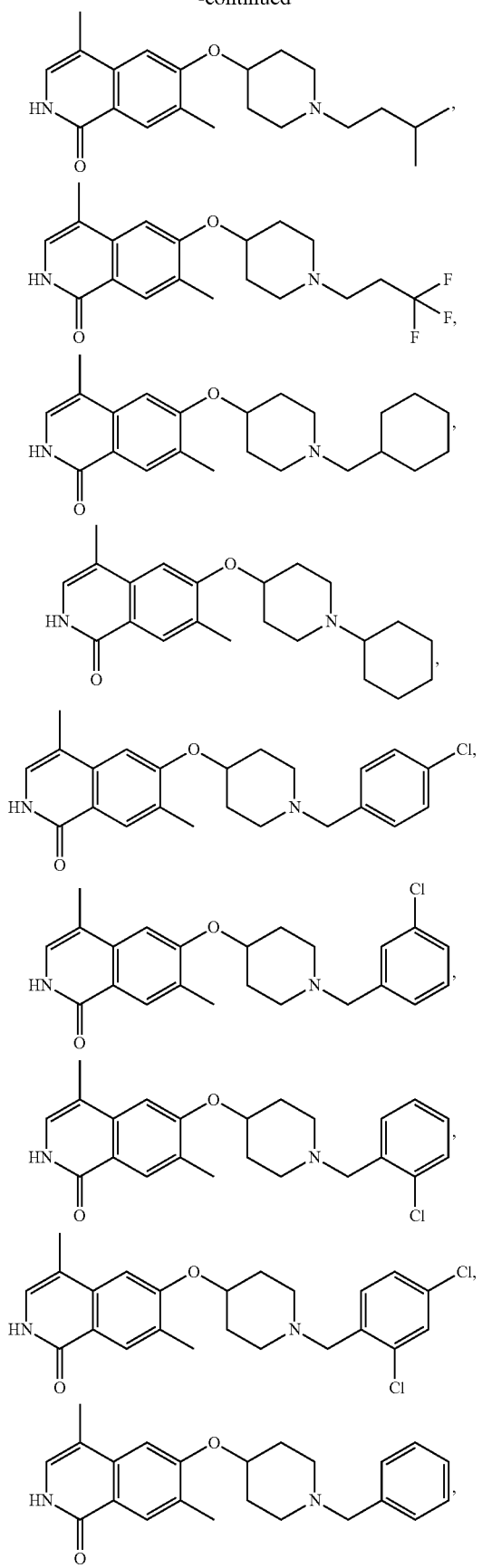
136
-continued
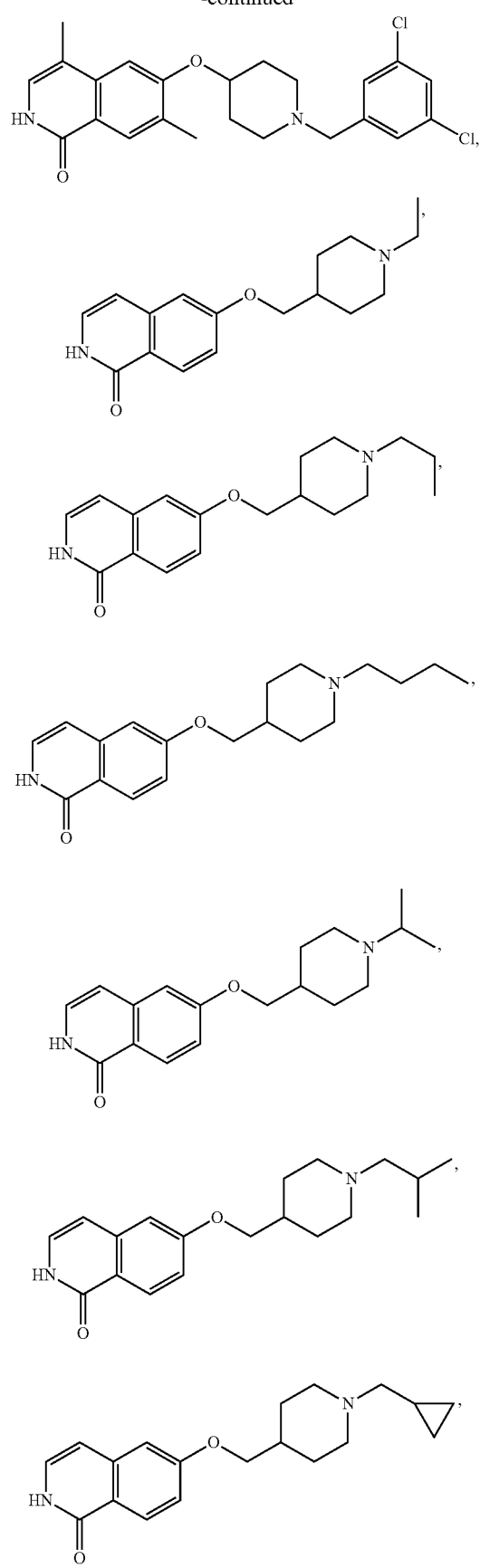

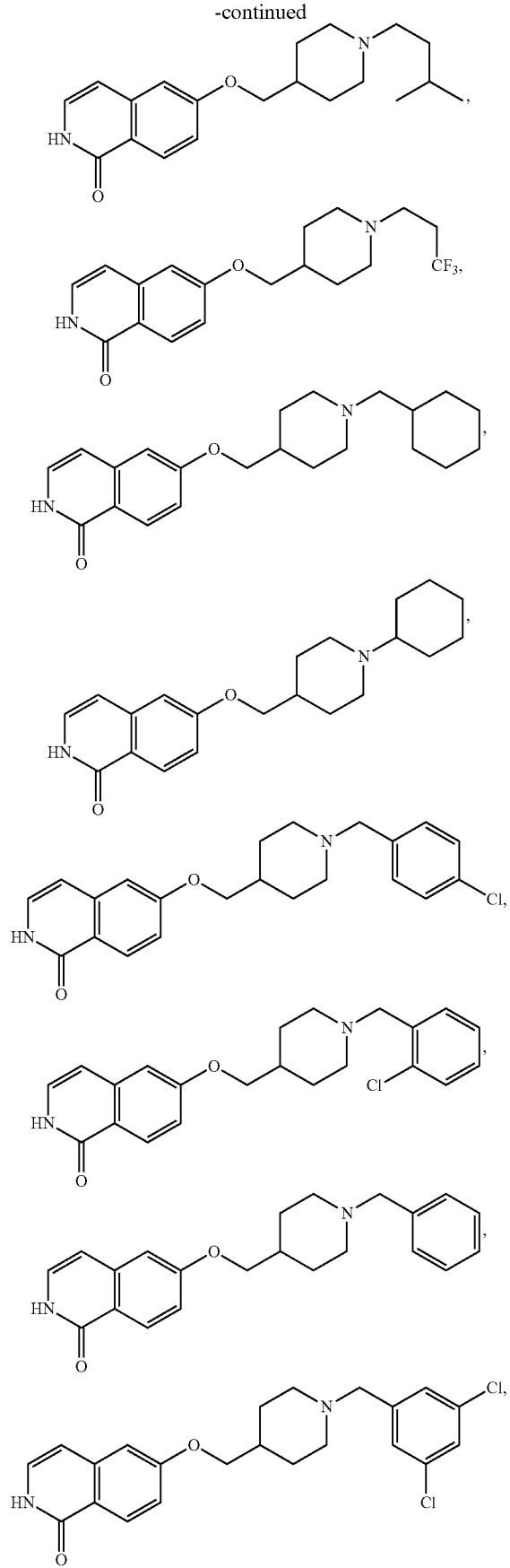
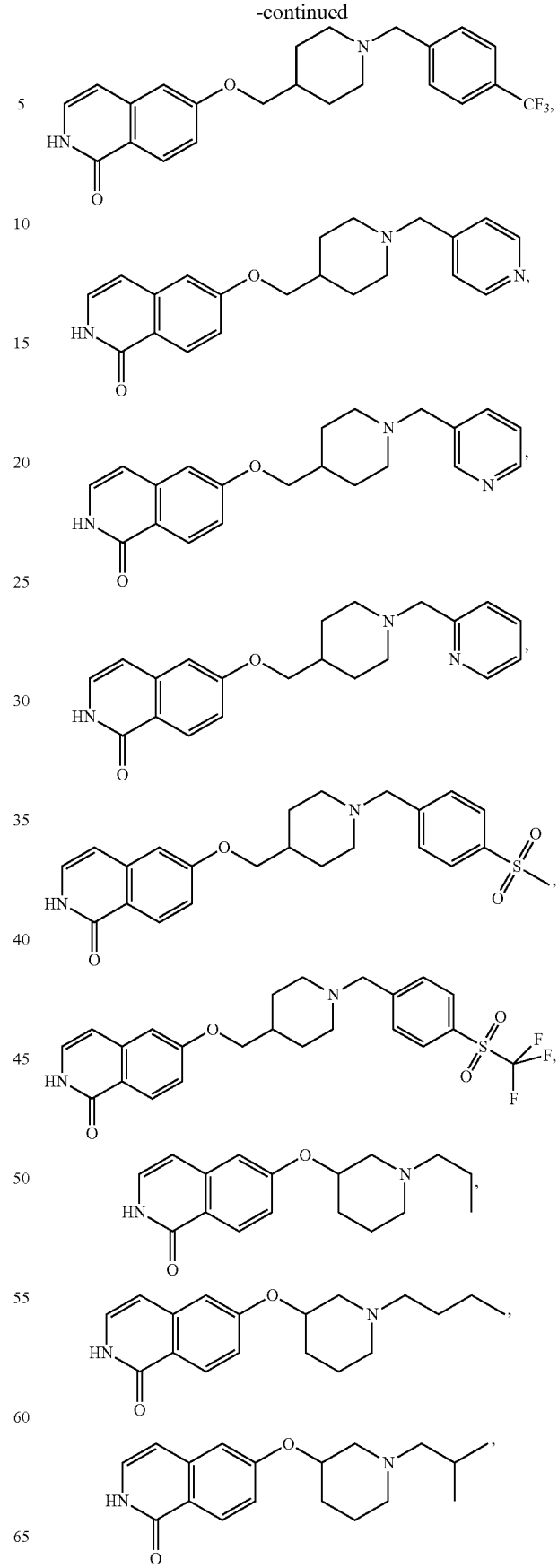

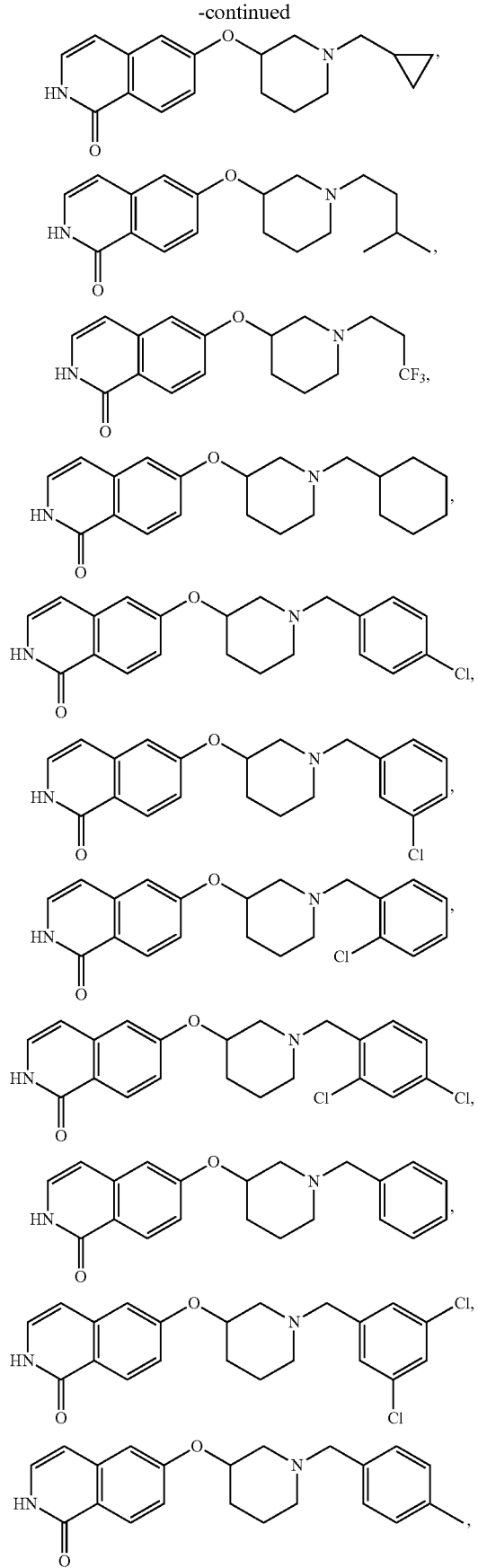
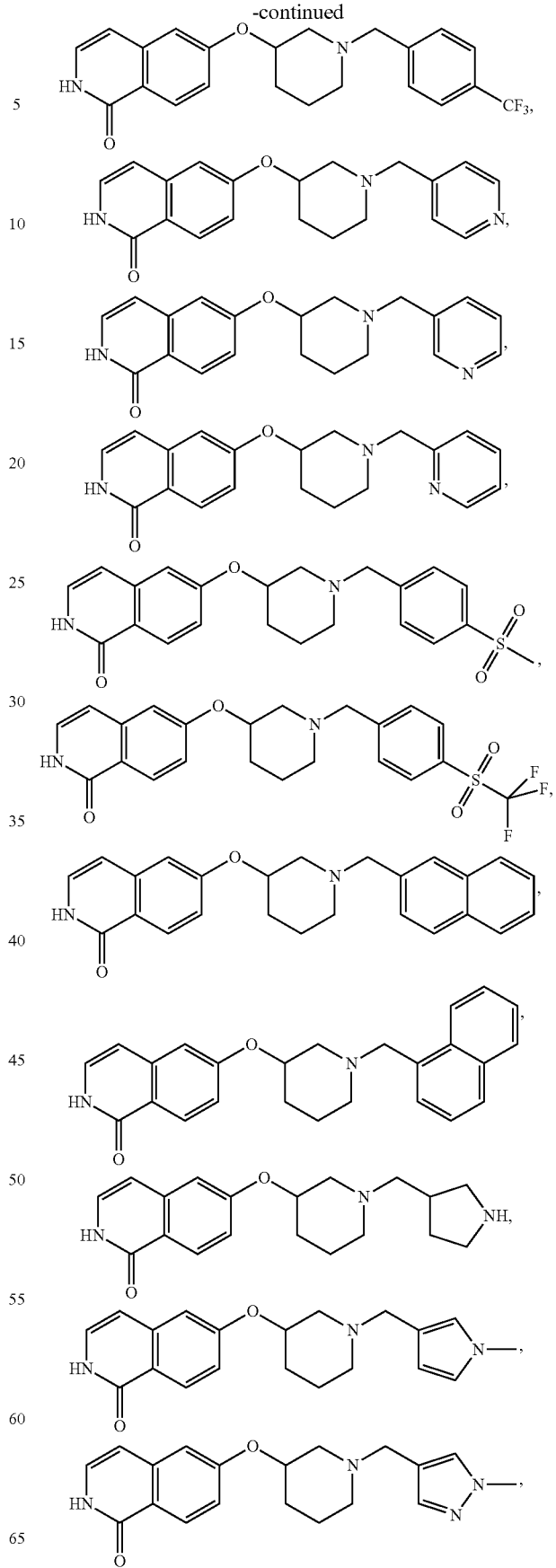

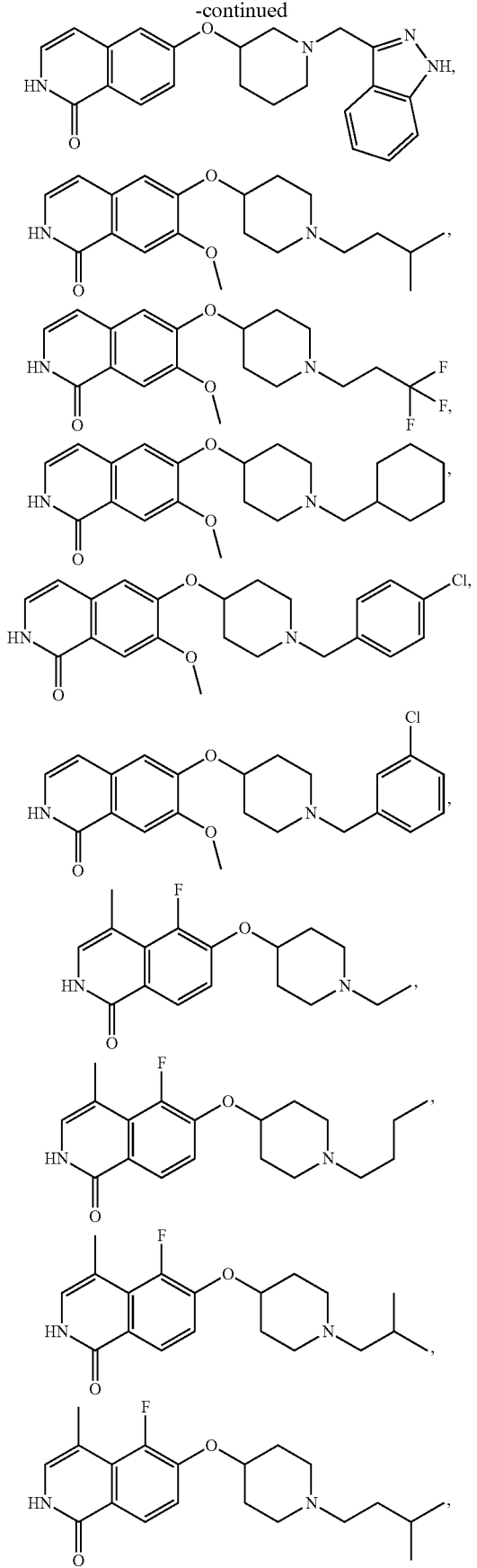
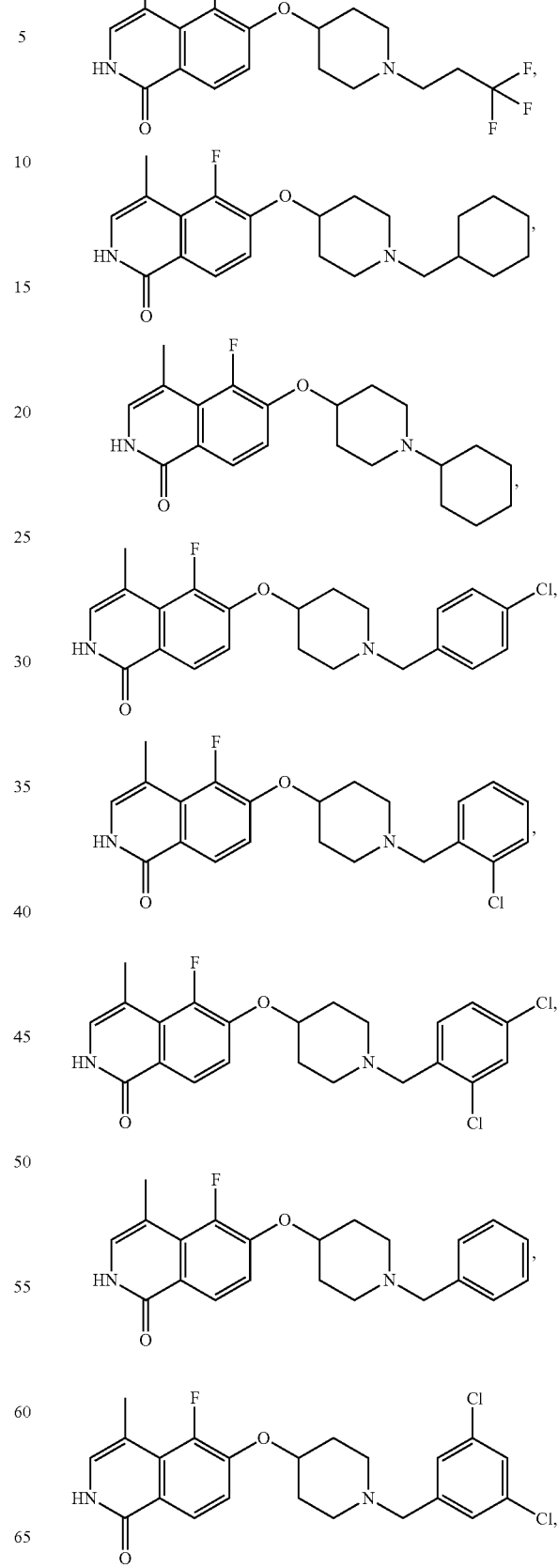

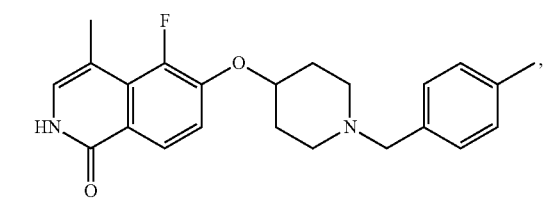
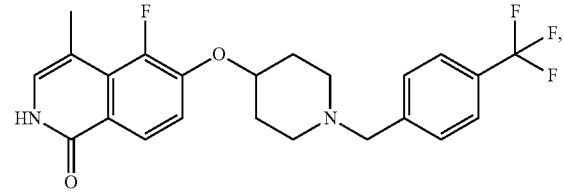
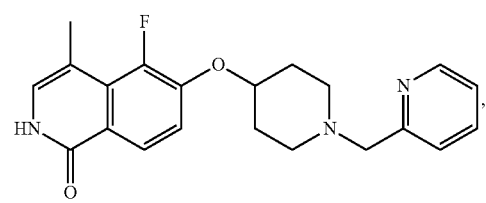
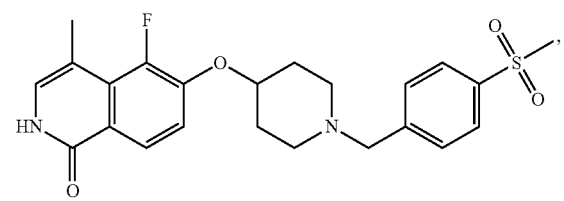
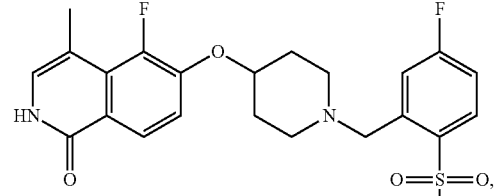
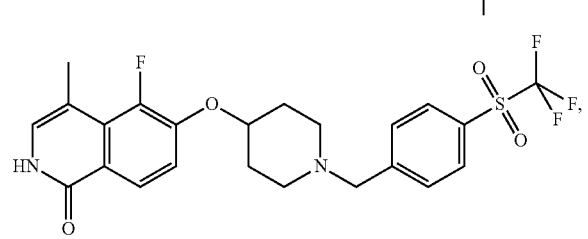
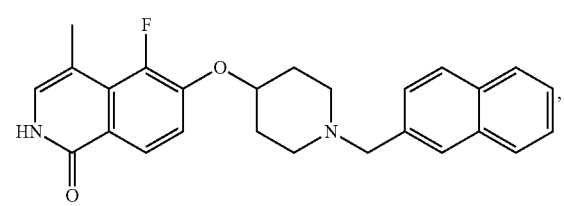
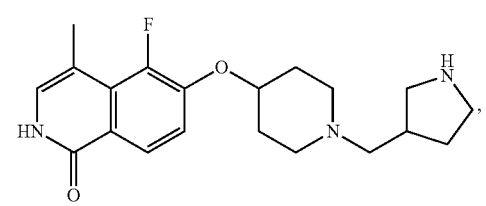
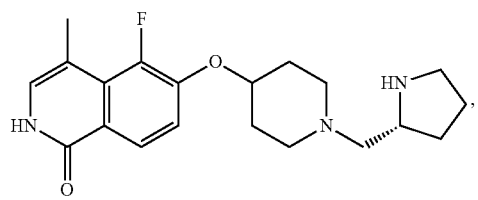
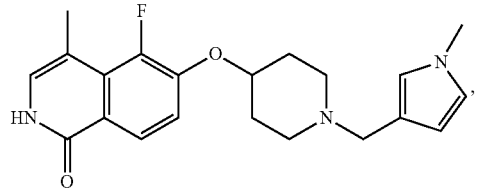
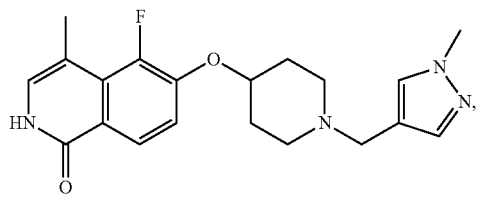
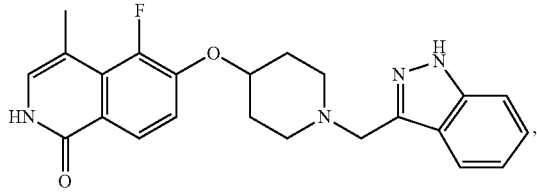
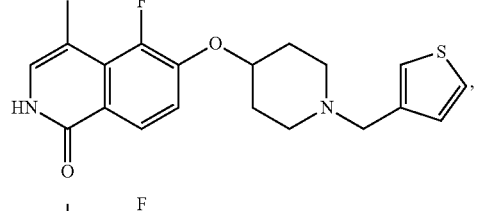
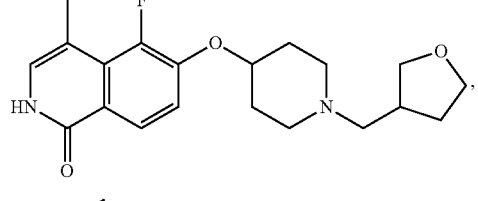
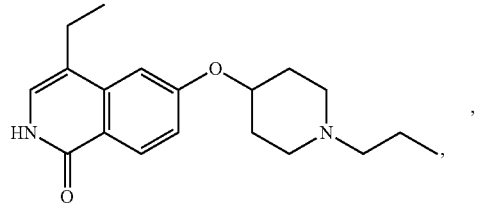
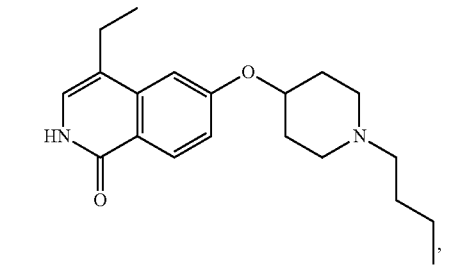

-continued
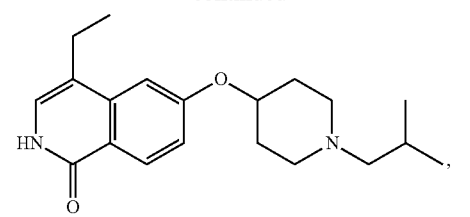
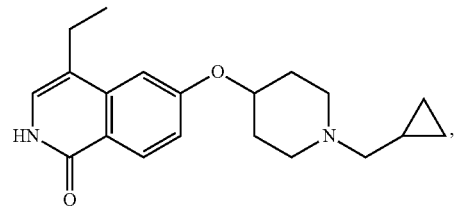
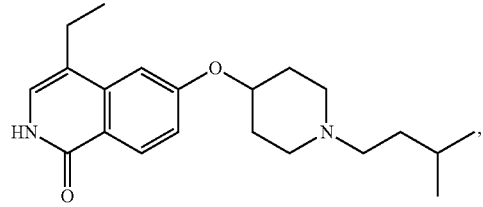
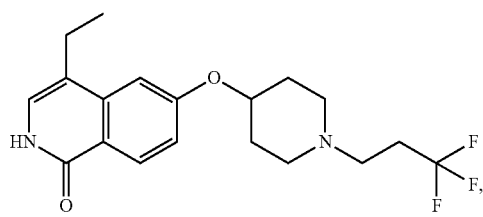
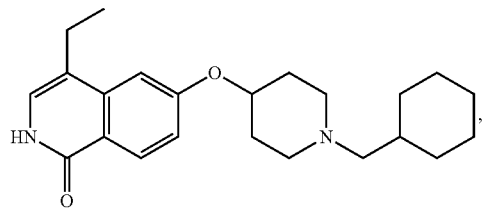
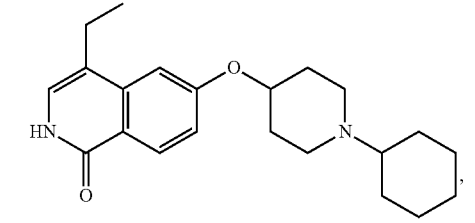
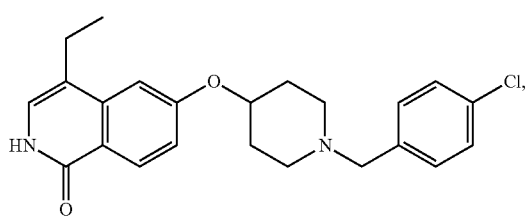
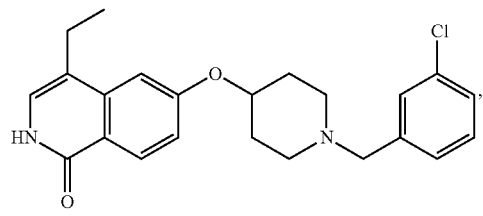
-continued
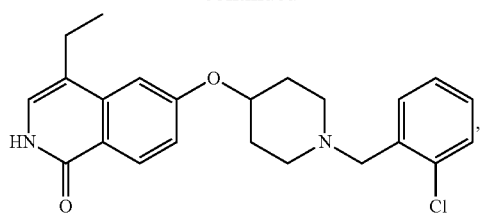
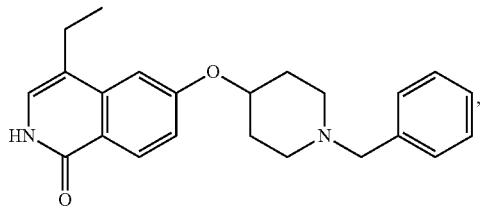
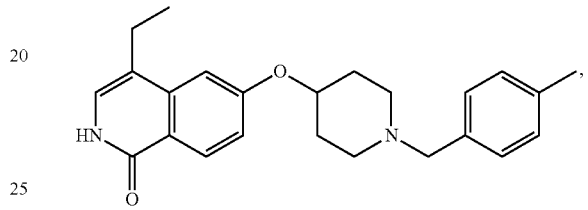
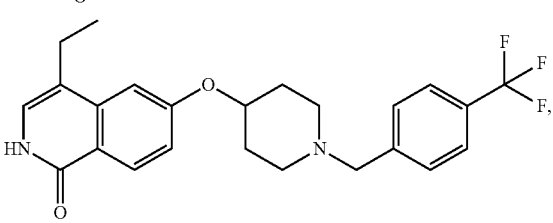
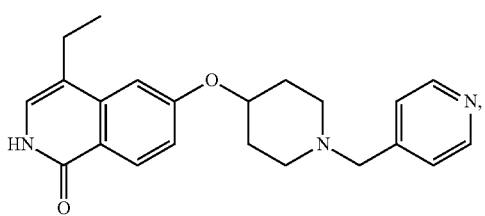
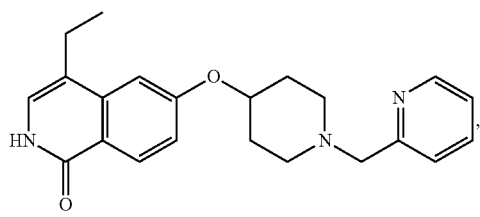
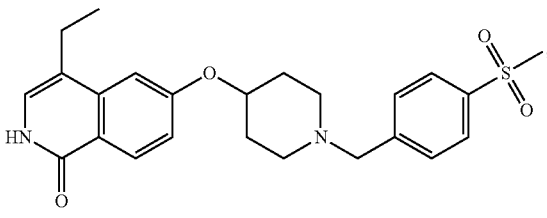
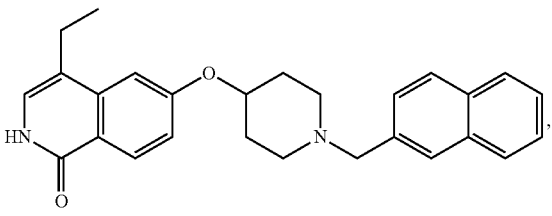

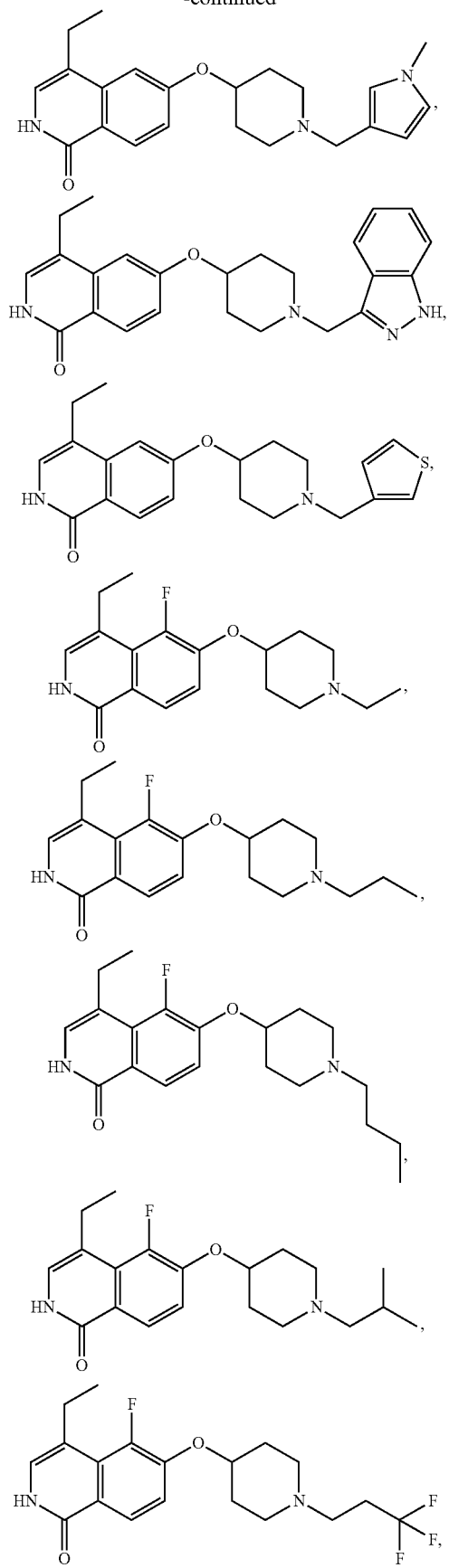
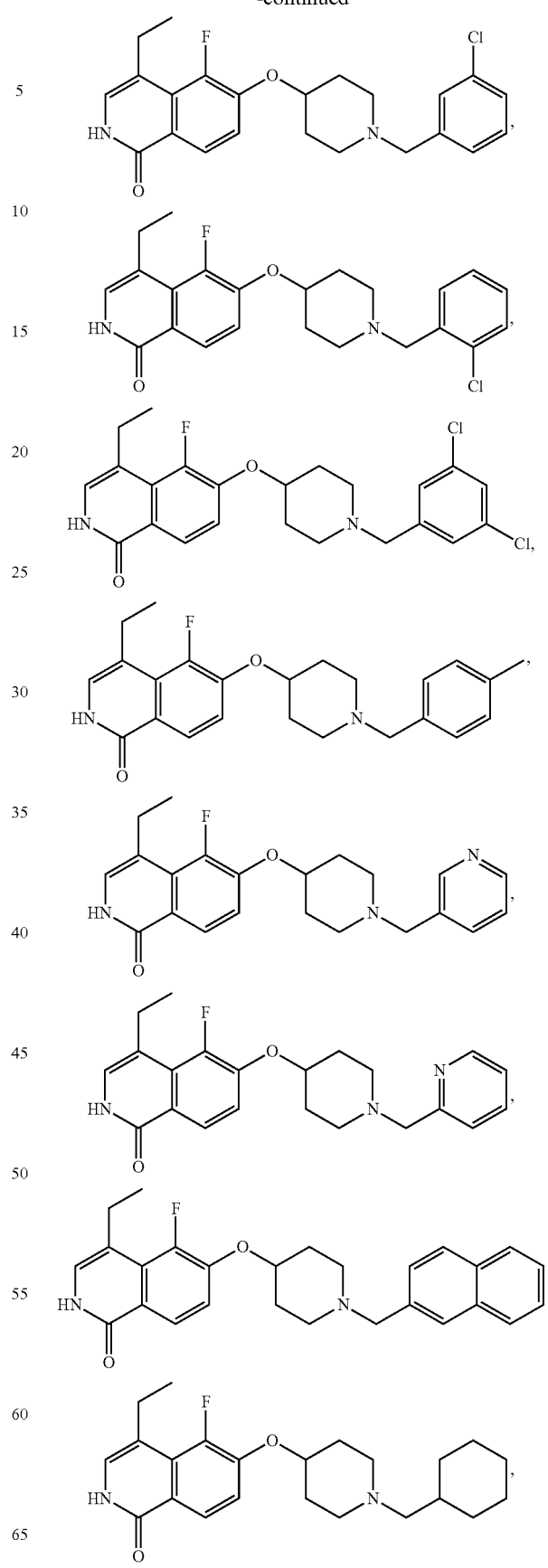

149
-continued
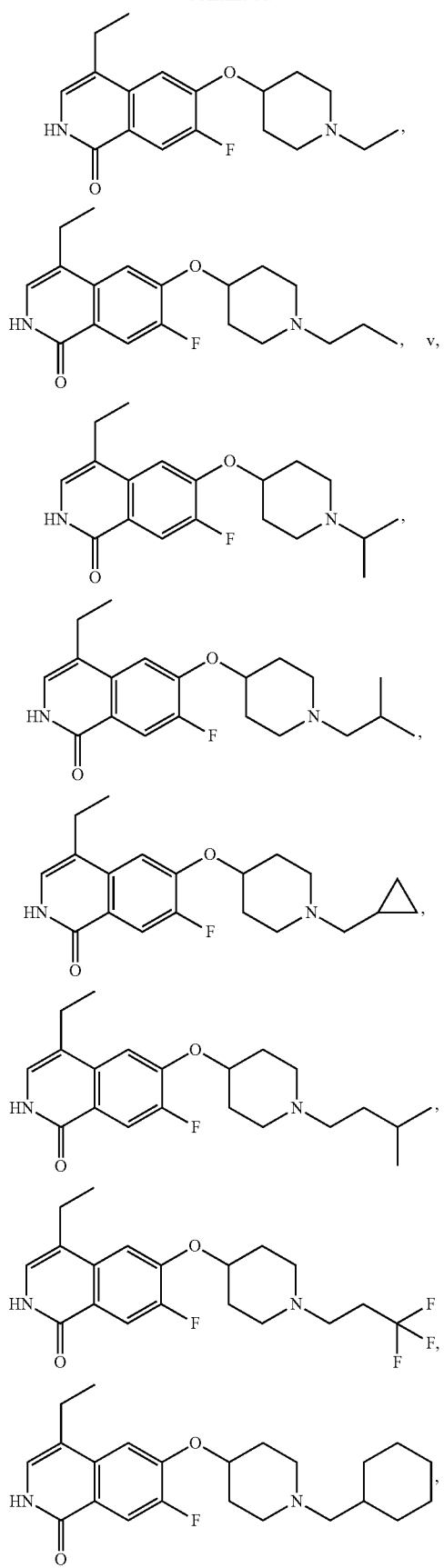
150
-continued
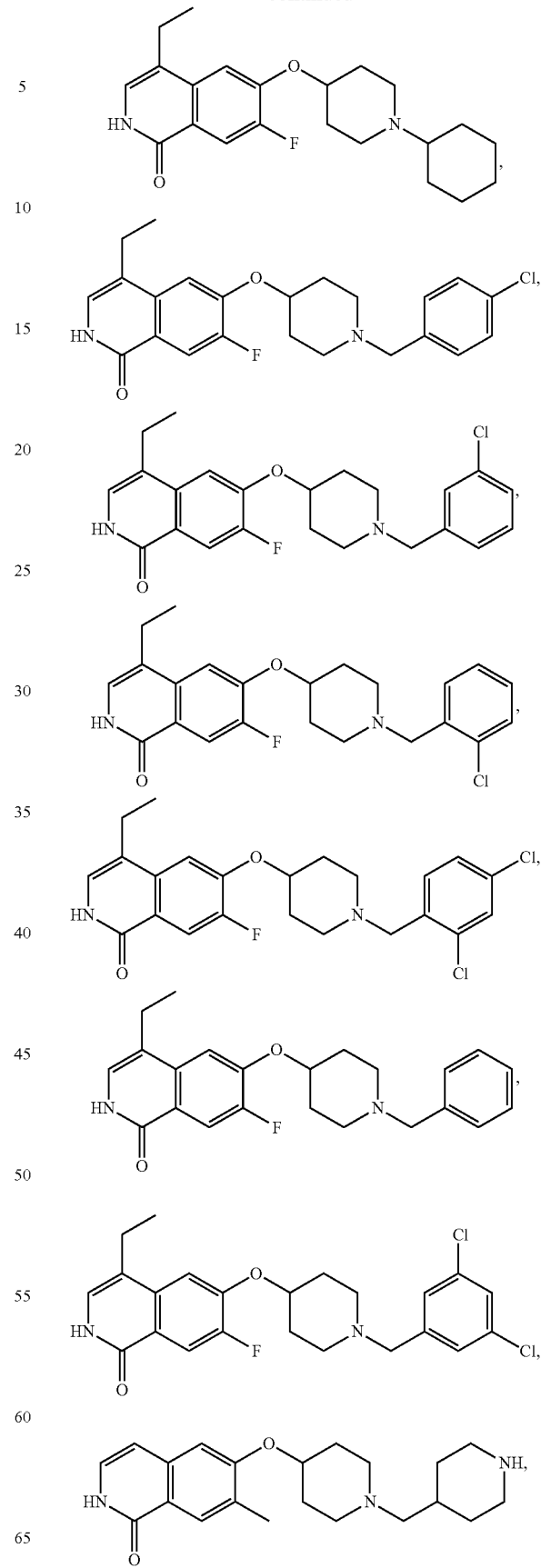

151
-continued
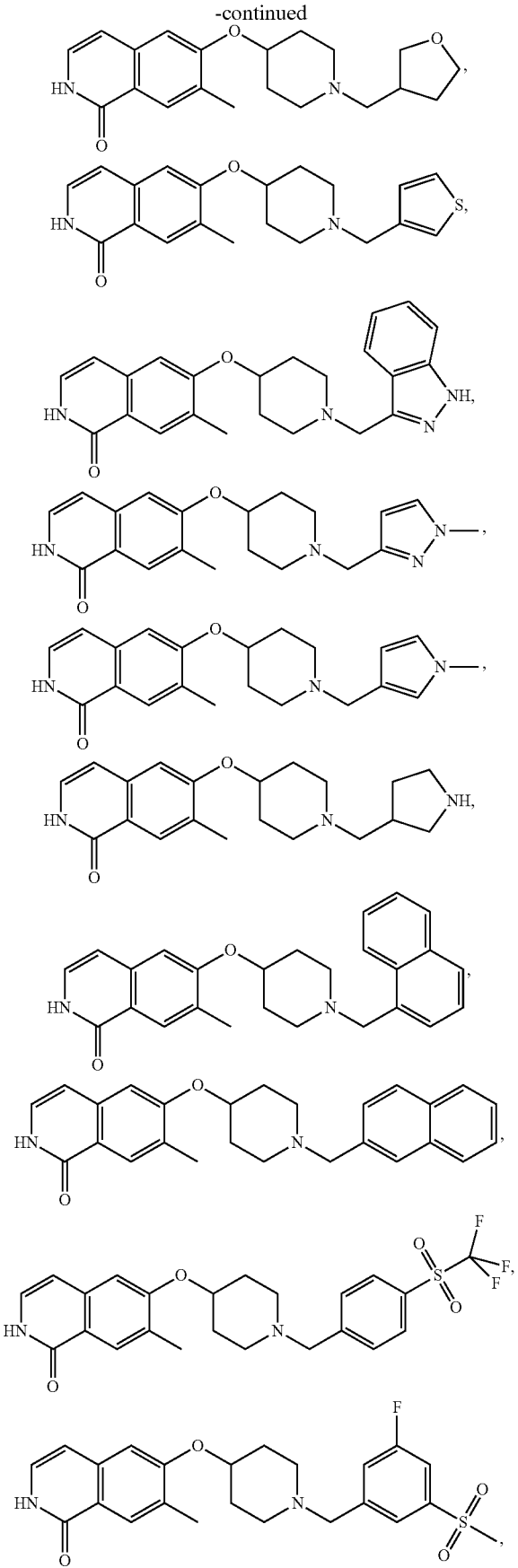
152
-continued
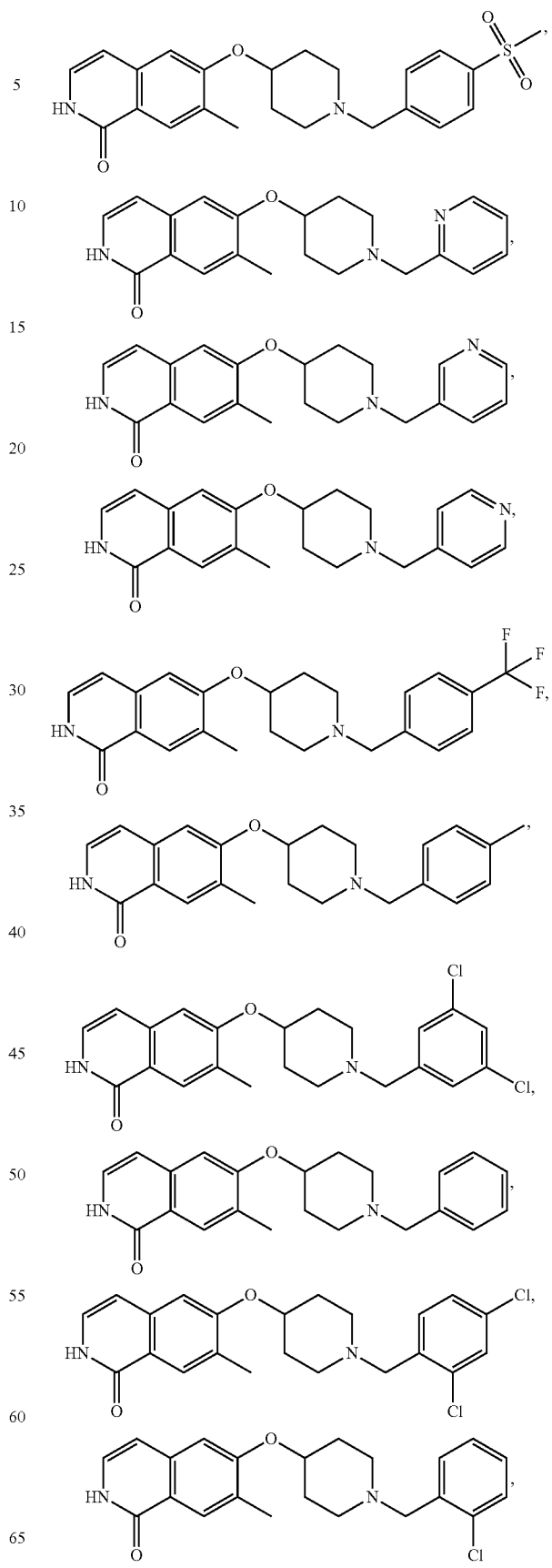

153
-continued
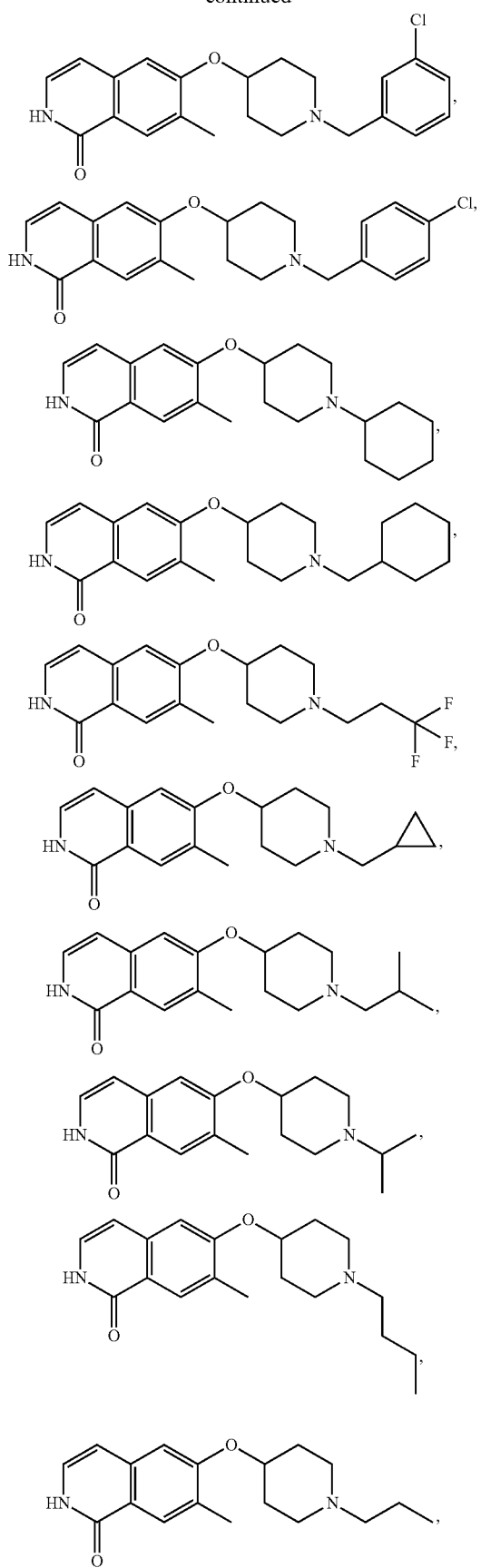
154
-continued
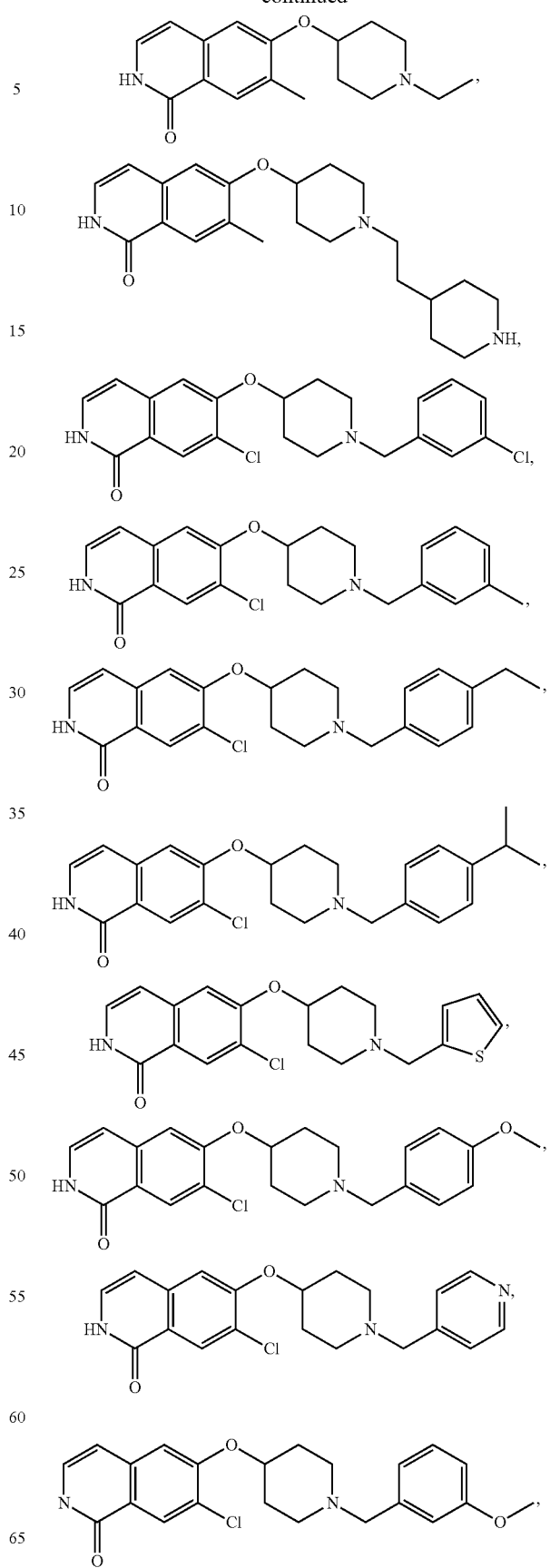

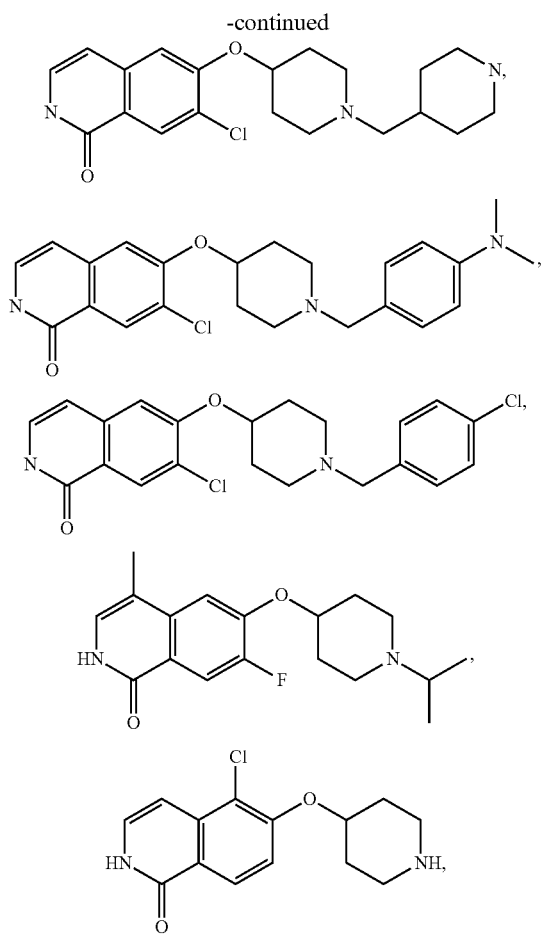

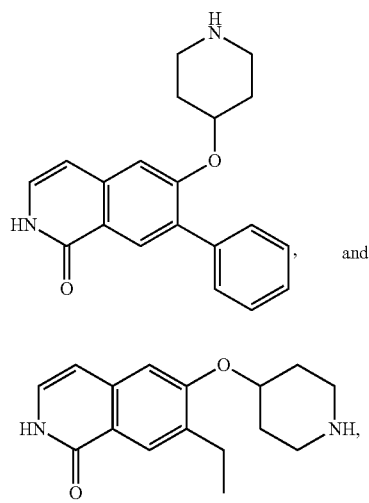

or tautomeric form thereof, or a pharmaceutically acceptable salt thereof, stereoisomeric form thereof or physiologically functional derivative thereof, pharmaceutically acceptable salt of a stereoisomeric form thereof or physiologically functional derivative thereof, or stereoisomeric form of a physiologically functional derivative thereof.

49. A compound of one of the following formula A1 or A2 or A3 or A4:

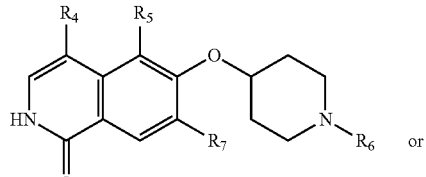

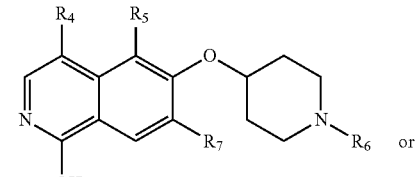

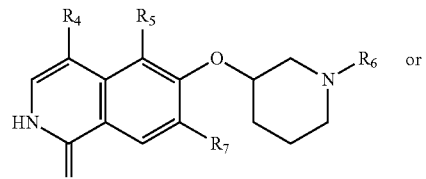

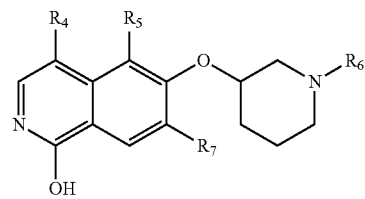

wherein $R_4$ is H, $(C_1\text{-}C_4)$alkyl, or halogen $R_5$ is H or halogen;

$R_7$ is H, $(C_1\text{-}C_4)$alkyl, or halogen;

$R_6$ is H, $(C_1\text{-}C_8)$alkyl, $(C_1\text{-}C_6)$alkylene-O—$(C_1\text{-}C_4)$alkyl, $(C_1\text{-}C_6)$alkylene-O—R' wherein R' is $(C_6\text{-}C_{10})$aryl, or $(C_1\text{-}C_6)$alkylene-R' wherein R' is $(C_3\text{-}C_8)$cycloalkyl, $(C_5\text{-}C_{10})$heterocyclyl, or $(C_6\text{-}C_{10})$aryl, wherein each $(C_6\text{-}C_{10})$aryl or $(C_5\text{-}C_{10})$heterocyclyl is optionally substituted with 1-3 substituents selected from ( $C_1\text{-}C_4$)alkyl, O—$(C_1\text{-}C_4)$alkyl, $SO_2$—$(C_1\text{-}C_4)$alkyl, and halogen;

or a pharmaceutically acceptable salt thereof.

50. The compound according to claim 49 wherein $R_6$ is H, $(C_1\text{-}C_6)$alkyl, or $(C_1\text{-}C_6)$alkylene-R' wherein R' is $(C_3\text{-}C_8)$cycloalkyl, $(C_5\text{-}C_{10})$heterocyclyl, or $(C_6\text{-}C_{10})$aryl, wherein each $(C_6\text{-}C_{10})$aryl or $(C_5\text{-}C_{10})$heterocyclyl is optionally substituted with 1-3 substituents selected from $(C_1\text{-}C_4)$alkyl, $SO_2$—$(C_1\text{-}C_4)$alkyl, and halogen;

or a pharmaceutically acceptable salt thereof.

51. A compound of one of the following formula A5 or A6 or A7 or A8:

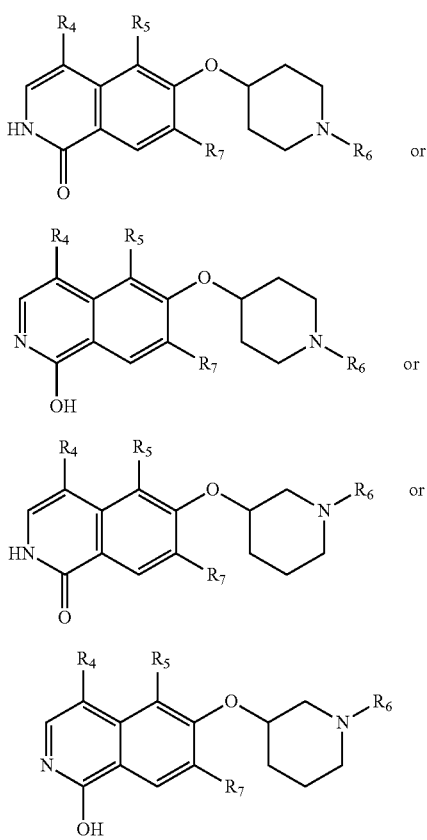

wherein
R$_4$ is H, (C$_1$-C$_4$)alkyl, or halogen;
R$_5$ is H or halogen;
R$_7$ is H, (C$_1$-C$_4$)alkyl, or halogen;
R$_6$ is H, (C$_1$-C$_6$)alkyl, or (C$_1$-C$_6$)alkylene-R'; and
R' is (C$_3$-C$_8$)cycloalkyl;
(C$_5$-C$_{10}$)heterocyclyl wherein the (C$_5$-C$_{10}$)heterocyclyl is furanyl, piperidinyl, pyrrolidinyl, pyrazolyl, pyridinyl, pyrrolyl, tetrahydrofuranyl, or thienyl wherein pyrazolyl or pyrrolyl is optionally substituted by (C$_1$-C$_4$)alkyl; or
(C$_6$-C$_{10}$)aryl wherein the (C$_6$-C$_{10}$)aryl is naphthyl or phenyl wherein the phenyl is optionally substituted with 1 or 2 substituents independently selected from halogen, (C$_1$-C$_4$)alkyl, O—(C$_1$-C$_4$)alkyl, and SO$_2$—(C$_1$-C$_4$)alkyl;
or a pharmaceutically acceptable salt thereof.

52. The compound according to claim 51 wherein
R$_4$ is H, methyl, ethyl, or Br;
R$_5$ is H or F; and
R$_7$ is H, methyl, Br, Cl, or F;
or a pharmaceutically acceptable salt thereof.

53. The compound according to claim 51 wherein
R$_6$ is H methyl, ethyl, propyl, isopropyl, butyl, isobutyl, 3-methylbutyl, cyclopropylmethyl, cyclohexylmethyl, benzyl, 2-chlorobenzyl, 3-chlorobenzyl, 4-chlorobenzyl, 2,4-dichlorobenzyl, 3,5-dichlorobenzyl, 4-methylbenzyl, 4-methylsulfonylbenzyl, 5-fluoro-2-methylsulfonylbenzyl, 5-fluoro-3-methylsulfonylbenzyl, naphth-1-ylmethyl, naphth-2-ylmethyl, pyridin-2-ylmethyl, pyridin-3-ylmethyl, pyridin-4-ylmethyl, thien-3-ylmethyl, piperidin-4-ylmethyl, 2-(piperidin-4-yl)ethyl, pyrrolidin-2-ylmethyl, pyrrolidin-3-ylmethyl, furan-3-ylmethyl, 1-methylpyrrol-3-ylmethyl, 1-methylpyrazol-3-ylmethyl, 1-methylpyrazol-4-ylmethyl, or tetrahydrofuran-3-ylmethyl;
or a pharmaceutically acceptable salt thereof.

54. A compound of the following formula B1 or B2

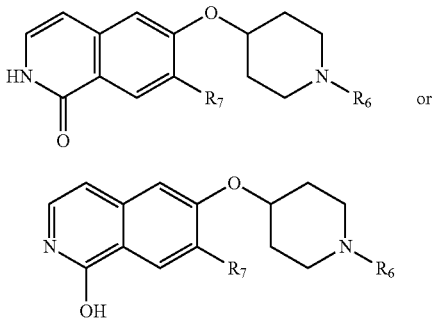

wherein
R$_6$ is H or (C$_1$-C$_6$)alkyl; and
R$_7$ is H or halogen,
or a pharmaceutically acceptable salt thereof.

55. The compound according to claim 54 wherein
R$_6$ is H or isopropyl; and
R$_7$ is H or Cl
or a pharmaceutically acceptable salt thereof.

56. A compound of formula

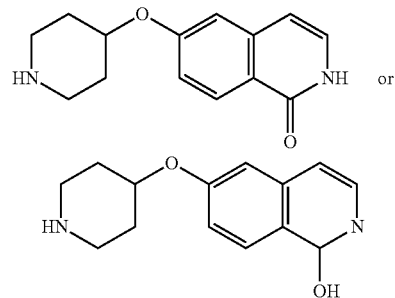

or a pharmaceutically acceptable salt thereof.

57. A compound of formula

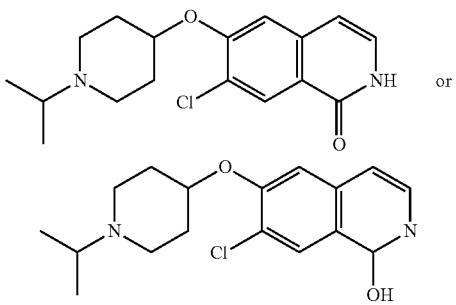

or a pharmaceutically acceptable salt thereof.

58. A compound of formula

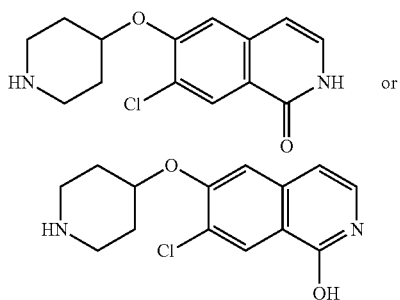

or a pharmaceutically acceptable salt thereof.

59. A compound of formula (I)

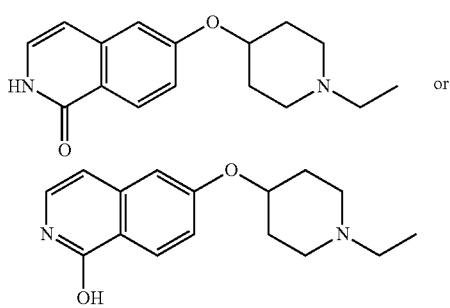

or a pharmaceutically acceptable salt thereof.

60. A compound of formula

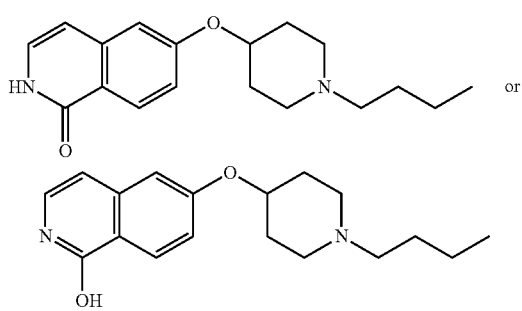

or a pharmaceutically acceptable salt thereof.

61. A compound of formula (I)

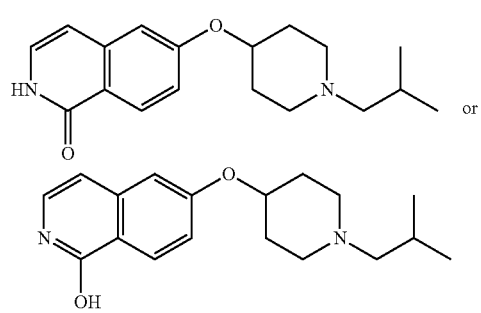

or a pharmaceutically acceptable salt thereof.

62. A compound of formula

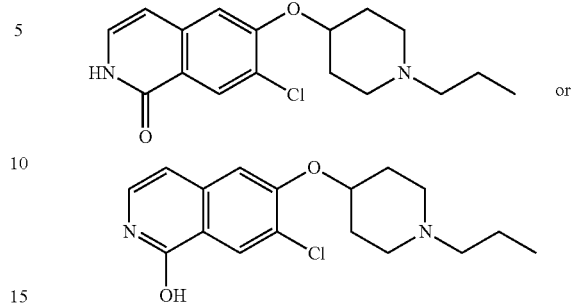

or a pharmaceutically acceptable salt thereof.

63. A compound of formula

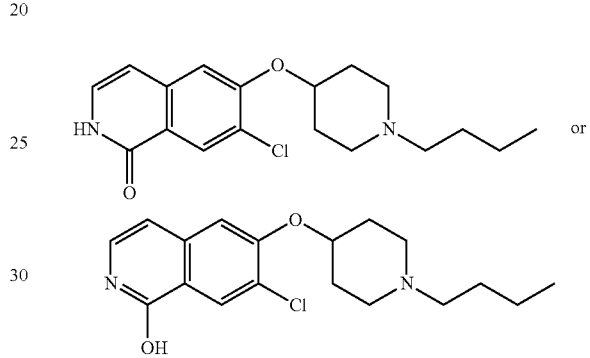

or a pharmaceutically acceptable salt thereof.

64. A compound of formula

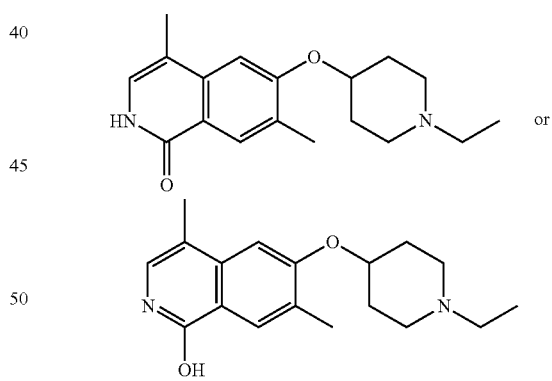

or a pharmaceutically acceptable salt thereof.

65. A compound of formula

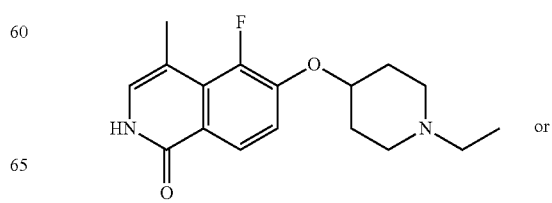

-continued

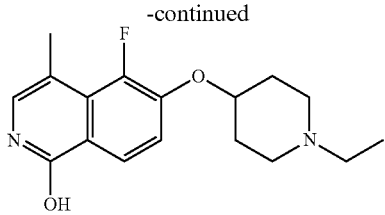

or a pharmaceutically acceptable salt thereof.

66. A pharmaceutical composition comprising an effective amount of at least one compound of the formulae (I) and (I'), or a pharmaceutically acceptable salt thereof, or stereoisomeric form thereof, or pharmaceutically acceptable salt of a stereoisomeric form as claimed in claim 1, and a physiologically tolerated excipient or carrier, or excipient and carrier and, where appropriate, a further additive or other active ingredient, or and additive and other active ingredient.

67. A method of treating or preventing in a patient a disease associated with Rho-kinase and/or Rho-kinase mediated phosphorylation of myosin light chain phosphatase comprising administering an effective amount of at least one compound of the formulae (I) and (I'),

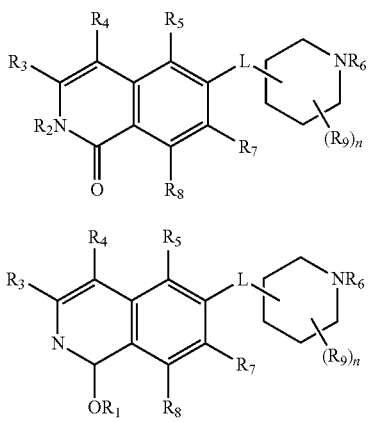

wherein

R1 is H, (C1-C6)alkyl, (C2-C6)alkenyl, (C2-C6)alkynyl, [(C1-C6)alkylene]0-1-(C3-C8)cycloalkyl, [(C1-C6)alkylene]0-1-(C5-C10)heterocyclyl, [(C1-C6)alkylene]0-1-(C6-C10)aryl, C(O)—(C1-C6)alkyl, C(O)(C2-C6)alkenyl, C(O)—(C2-C6)alkynyl, C(O)-[(C1-C6)alkylene]0-1-(C3-C8)cycloalkyl, C(O)-[(C1-C6)alkylene]0-1-(C5-C10)heterocyclyl, or C(O)-[(C1-C6)alkylene]0-1-(C6-C10)aryl;

R2 is H, (C1-C6)alkyl, [(C1-C6)alkylene]0-1-R', [(C1-C6)alkylene]0-1-O—(C1-C6)alkyl, [(C1-C6)alkylene]0-1-O—R', [(C1-C6)alkylene]0-1-NH2, [(C1-C6)alkylene]0-1-NH(C1-C6)alkyl, [(C1-C6)alkylene]0-1-N[(C1-C6)alkyl]2,
[(C1-C6)alkylene]0-1-CH[R']2,
[(C1-C6)alkylene]0-1-C(O)—R', [(C1-C6)alkylene]0-1-C(O)NH2,
[(C1-C6)alkylene]0-1-C(O)NH—R', or [(C1-C6)alkylene]0-1-C(O)N[R']2 ;

R3 is H, halogen, CN, (C1-C6)alkyl, (C1-C6)alkylene-R', OH, O—R", NH2, NHR", NR"R" or NH—C(O)—R";

R4 is H, halogen, OH, CN, (C1-C6)alkyl, (C3-C8)cycloalkyl, (C1-C6)alkylene-R' or NH—(C6-C10)aryl;

R5 is H, halogen, CN, NO2, (C1-C6)alkyl, (C2-C6)alkenyl, R', (C1-C6)alkylene-R',
(C1-C6)alkylene-(C6-C10)aryl, (C2-C6)alkenylene-(C6-C10)aryl,
(C1-C6)alkylene-(C5-C10)heterocyclyl, NH2, NH—R', NH—SO2H, NH—SO2-(C1-C6)alkyl,
NH—SO2-R', NH—C(O)—(C1-C6)alkyl, NH—C(O)—R', C(O)N[(C1-C6)alkyl]2, C(O)OH or
C(O)O—(C1-C6)alkyl;

R6 is H, R', (C1-C8)alkyl, (C1-C6)alkylene-R', (C1-C6)alkylene-O—(C1-C6)alkyl, (C1-C6)alkylene-O—R', (C1-C6)alkylene-CH[R']2, (C1-C6)alkylene-C(O)—R',
(C1-C6)alkylene-C(O)NH2, (C1-C6)alkylene-C(O)NH—R', or (C1-C6)alkylene-C(O)N[R']2;

R7 and R8 are independently of each other H, halogen, CN, NO2, (C1-C6)alkyl, O—(C1C6)alkyl, O—[(C1-C6)alkylene]0-1-R', (C2-C6)alkenyl, R', (C2-C6)alkenylene-(C6-C10)aryl, (C1-C6)alkylene-R', NH2, NH—R', NH—SO2H, NH—SO2-(C1-C6)alkyl, NH—SO2-R', SO2-NH2, SO2-NHR', NH—C(O)—(C1-C6)alkyl, NH—C(O)—R', C(O)N[(C1-C6)alkyl]2, C(O)OH or C(O)O—(C1-C6)alkyl;

R9 is halogen or (C1-C6)alkyl;

R' is (C3-C8)cycloalkyl, (C5-C10)heterocyclyl or (C6-C10)aryl;

R" is (C3-C8)cycloalkyl, (C5-C10)heterocyclyl, (C6-C10)aryl, (C1-C6)alkyl,
(C1-C6)alkylene-R', (C1-C6)alkylene-O—(C1-C6)alkyl, (C1-C6)alkylene-O—R', or (C1-C6)alkylene-NRxRy;

Rx and Ry are independently of each other (C1-C6)alkyl, (C5-C10)heterocyclyl, (C6-C10)aryl, (C1-C4)alkylene-(C5-C10)heterocyclyl,
(C1-C4)alkylene-(C6-C10)aryl, (C1-C4)alkylene-NH(C1-C6)alkyl,
(C1-C4)alkylene-N[(C1-C6)alkyl]2, (C1-C4)alkylene-N[(C6-C10)aryl]2, or
(C1-C4)alkylene-N[(C5-C10)heterocyclyl]2;

n is 0, 1, 2, 3 or 4; and

L is O or O—(C1-C6)alkylene;

wherein in residues R4, R5, R7 and R8 one alkyl or alkylene hydrogen atom can optionally be substituted by OH, OCH3, COOH, COOCH3, NH2, NHCH3, N(CH3)2, CONH2, CONHCH3 or CON(CH3)2, or an alkyl or alkylene may be halogenated once or more;

or its physiologically acceptable salt thereof, stereoisomeric form thereof or physiologically functional derivative thereof, pharmaceutically acceptable salt of a stereoisomeric form thereof or physiologically functional derivative thereof, or stereoisomeric form of a physiologically functional derivative thereof wherein the disease is hypertension, glaucoma, nephropathy, renal failure, and atherosclerosis.

68. A method of treating Rho-kinase associated disorders consisting of hypertension, atherosclerosis and glaucoma comprising administering an effective amount of a compound of claim 49, 51, or 54 to a patient in need thereof.

69. A method of treating Rho-kinase associated disorders consisting of hypertension, atherosclerosis and glaucoma comprising administering an effective amount of a compound as in any one of claims 56-65 to a patient in need thereof.

* * * * *